(12) United States Patent
Coruzzi et al.

(10) Patent No.: US 11,535,855 B2
(45) Date of Patent: Dec. 27, 2022

(54) NITROGEN RESPONSIVE TRANSCRIPTION FACTORS IN PLANTS

(71) Applicant: New York University, New York, NY (US)

(72) Inventors: Gloria M. Coruzzi, New York, NY (US); Matthew Brooks, White Plains, NY (US); Kranthi Varala, West Lafayette, IN (US)

(73) Assignee: New York University, New York, NY (US)

( * ) Notice: Subject to any disclaimer, the term of this patent is extended or adjusted under 35 U.S.C. 154(b) by 67 days.

(21) Appl. No.: 16/625,286

(22) PCT Filed: Jun. 22, 2018

(86) PCT No.: PCT/US2018/039073
§ 371 (c)(1),
(2) Date: Dec. 20, 2019

(87) PCT Pub. No.: WO2018/237308
PCT Pub. Date: Dec. 27, 2018

(65) Prior Publication Data
US 2021/0310016 A1    Oct. 7, 2021

Related U.S. Application Data

(60) Provisional application No. 62/587,167, filed on Nov. 16, 2017, provisional application No. 62/523,505, filed on Jun. 22, 2017.

(51) Int. Cl.
| | | |
|---|---|---|
| C12N 15/82 | (2006.01) | |
| C07K 14/415 | (2006.01) | |
| C12N 15/11 | (2006.01) | |
| C12N 15/113 | (2010.01) | |

(52) U.S. Cl.
CPC ........ C12N 15/8241 (2013.01); C07K 14/415 (2013.01); C12N 15/111 (2013.01); C12N 15/113 (2013.01); C12N 2310/141 (2013.01); C12N 2310/20 (2017.05); C12N 2320/50 (2013.01)

(58) Field of Classification Search
None
See application file for complete search history.

(56) References Cited

U.S. PATENT DOCUMENTS

2015/0067923 A1    3/2015   Coruzzi et al.

OTHER PUBLICATIONS

Kawai-Yamada, Maki, et al. "A novel *Arabidopsis* gene causes Bax-like lethality in *Saccharomyces cerevisiae*." Journal of Biological Chemistry 280.47 (2005): 39468-39473. (Year: 2005).*
Hallmark, et al. (Plant Science 289 (2019): 110251). (Year: 2019).*
Zwack et al. (Plant cell reports 35.3 (2016): 573-584). (Year: 2016).*
Compton, M. A. "Cytokinin Response Factor4: a role in development during cold stress in *Arabidopsis thaliana*." (2012). (Year: 2012).*
Xu et al. (Scientific reports 6.1 (2016): 1-14) (Year: 2016).*
Zwack, P.J., et al., Cytokinin response factor 4 (CRF4) is induced by cold and involved in freezing tolerance, Plant Cell Reports, Dec. 9, 2015, vol. 35, No. 3, pp. 573-584.
Goel, P., et al., Abiotic Stresses Downregulate Key Genes Involved in Nitrogen Uptake and Assimilation in *Brassica iuncea* L., PLoS One, Nov. 25, 2015, vol. 11, No. 11, e0143645, 17 pages.
Shi, X, et al., Characterizatin of two tomato AP2/ERF genes, SlCRF1 and SlCRF2 in hormone and stress response, Plant Cell Reports, Jan. 2014, Oct. 1, 2013, vol. 22, No. 1, pp. 35-45.

\* cited by examiner

*Primary Examiner* — Charles Logsdon
(74) *Attorney, Agent, or Firm* — Hodgson Russ LLP

(57) ABSTRACT

Methods for increasing or decreasing Nitrogen (N) uptake/assimilation and/or usage in plants comprising over-expressing or repressing one or more transcription factors that have been identified by evaluating temoporal transcription of the TFs in response to N signaling and validated based on TF perturbation studies in plant cells and plants. Combinations of TFs may be used, where each TF may be independently induced or repressed to achieve a desired increase or decrease in N uptake/assimilation.

8 Claims, 36 Drawing Sheets

| GeneID | Name | Just in Time N-induction (min) | A. DAP-Seq Targets in NxTime response (2,172 genes) | B. DAP-Seq Targets in genome (28,714 genes) | TF Influence in N-response $p_n=(A/2172)$ | TF Influence in genome $p_g=(B/28714)$ | N-specificity index of TF (p-value) $H_0: p_n = p_g$ |
|---|---|---|---|---|---|---|---|
| AT4G27950 | CRF4 | 5 | 364 | 829 | 0.087986 | 0.025425 | 1.140E-29 |
| AT1G25550 | HHO3 | 10 | 427 | 1978 | 0.103215 | 0.060664 | 1.295E-93 |
| AT1G68670 | HHO2 | 10 | 880 | 4077 | 0.212715 | 0.125038 | 1.249E-71 |
| AT4G37180 | HHO5 | 10 | 449 | 2112 | 0.108533 | 0.064773 | 1.213E-102 |
| AT5G62020 | HSFB2A | 10 | 1656 | 8465 | 0.400290 | 0.259615 | 8.773E-09 |
| AT5G07680 | NAC4 | 10 | 1243 | 6440 | 0.300459 | 0.197510 | 9.068E-07 |
| AT2G33550 | ASR3 | 10 | 1429 | 7431 | 0.345419 | 0.227903 | 2.082E-17 |
| AT1G45249 | ABF2 | 15 | 1916 | 10041 | 0.463138 | 0.307949 | 1.600E-29 |
| AT5G15830 | bZIP3 | 15 | 209 | 1103 | 0.050520 | 0.033828 | 3.392E-61 |
| AT5G65210 | TGA1 | 15 | 1327 | 7098 | 0.320764 | 0.217690 | 3.615E-57 |
| AT5G46590 | ANAC096 | 15 | 1552 | 8374 | 0.375151 | 0.256824 | 1.311E-18 |
| AT4G24020 | NLP7 | 20 | 1788 | 9713 | 0.432197 | 0.297890 | 5.015E-143 |
| AT3G62420 | BZIP53 | 30 | 942 | 5126 | 0.227701 | 0.157210 | 5.029E-67 |
| AT5G10030 | TGA4 | 30 | 1110 | 6110 | 0.268310 | 0.187389 | 9.320E-40 |
| AT1G49560 | HHO6 | 45 | 2304 | 13331 | 0.556925 | 0.408851 | 1.327E-78 |
| AT5G66730 | IDD1 | 45 | 2012 | 12035 | 0.486343 | 0.369104 | 8.139E-35 |
| AT5G58900 |  | 45 | 416 | 2581 | 0.100556 | 0.079157 | 1.273E-82 |
| AT5G29000 | PHL1 | 60 | 1135 | 7131 | 0.274353 | 0.218702 | 3.022E-64 |
| AT5G47390 | MYBH | 90 | 1322 | 8428 | 0.319555 | 0.258480 | 3.770E-54 |

Figure 7

| Time in minutes | "Just-in-time" geneset | Representative GO terms |
|---|---|---|
| 5 | 57 | Response to nitrate, Nitrate transport, Biological regulation |
| 10 | 181 | Regulation of transcription, Response to hormone stimulus, Regulation of nitrogen compound metabolic process |
| 15 | 84 | Response to nitrate, Nitrate transport, Response to water, Transcription factor activity |
| 20 | 68 | Glycolysis, Hexose metabolism, Response to salt/osmotic stress, Transmembrane transport |
| 30 | 78 | Cellular carbohydrate metabolic process, Oxoacid metabolic process |
| 45 | 366 | RNA modification, RNA methylation, Protein localization, Ribosome biogenesis, ncRNA processing, protein targeting, RNA processing, mitochondrial transport, histone methylation Chromatin organization, Photomorphogenesis |
| 60 | 233 | Protein localization, Nucleotide biosynthetic process, RNA methylation, Nuclear transport, RNA modification, Mitochondrial organization, Ribosome biogenesis, Photomorphogenesis |
| 90 | 455 | RNA methylation, RNA modification, Methylation, Nucleotide biosynthetic process, Ribosome biogenesis, Response to red or far red light, RNA splicing |
| 120 | 73 | Nucleotide biosynthetic process, protein deneddylation, tRNA metabolic process, Response to light stimulus |

Figure 14

Common genes targeted by 50% of 23 TFs relate to N-use

| # of TFs | # of target genes |
|---|---|
| 1 | 3620 |
| 2 | 1952 |
| 3 | 1288 |
| 4 | 935 |
| 5 | 722 |
| 6 | 532 |
| 7 | 408 |
| 8 | 338 |
| 9 | 295 |
| 10 | 238 |
| 11 | 187 |
| 12 | 158 |
| 13 | 115 |
| 14 | 112 |
| 15 | 65 |
| 16 | 47 |
| 17 | 58 |
| 18 | 29 |
| 19 | 16 |
| 20 | 13 |
| 21 | 6 |
| 22 | 3 |
| Total | 12,094 |

Common TF-TARGET genes (1,047)

| GO-Term | p-value |
|---|---|
| nucleosome organization | 1.87e-11 |
| cellular amino acid metabolic process | 1.44e-10 |
| cellular nitrogen compound biosynthetic process | 6.91e-9 |
| regulation of hormone levels | 4.03e-6 |
| response to jasmonic acid | 1.49e-5 |
| auxin metabolic process | 1.63e-5 |
| response to abscisic acid stimulus | 4.73e-5 |
| root development | 8.21e-5 |

Figure 22

TF-regulation (*TARGET*) + TF-binding (DAP-Seq)
uncovers cis-motifs involved in gene induction OR repression

| TF | Overlap *TARGET* (regulation) & DAP-Seq (TF-binding) | Enrichment of DAP-Seq Cis-Motif | | |
|---|---|---|---|---|
| | | DAP-Seq bound Promoters (Top 1500 peaks) | *TARGET* Induced Genes (All) | *TARGET* Repressed Genes (All) |
| HB6 | 910 | 3.5E-203 | 4.4E-206 | 2.2E-18 |
| CRF4 | 11 | 3.8E-18 | 4.4E-02 | 2.0E-02 |
| HSFB2A | 239 | 1.2E-87 | n.s. | 1.0E-05 |
| HHO2 | 567 | 1.8E-119 | n.s. | 3.3E-19 |
| NAC4 | 136 | 3.6E-25 | n.s. | 4.6E-02 |
| TGA1 | 1347 | 2.7E-42 | 1.2E-06 | n.s. |
| TGA4 | 216 | 1.8E-157 | 3.4E-06 | n.s. |
| bZIP3 | 723 | 2.1E-216 | 4.4E-04 | n.s. |
| HHO3 | 388 | 1.1E-160 | 7.9E-03 | n.s. |
| ASR3 | 249 | 7.9E-103 | 4.3E-08 | n.s. |

Overlap p-value: 0.05 — 1e-100 — 1e-200

Figure 23

| N Assimilation Step | Target Gene Full Name | Target GeneID | Target Gene Name | Target Hit Count (Root) | HHO3 (Root) Induced-4 Repressed-6 | ZFP4 (Root) Induced-8 Repressed-15 | HHO2 (Root) Induced-9 Repressed-11 | ERF036 (Root) Induced-2 Repressed-21 | HB6 (Root) Induced-10 Repressed-10 |
|---|---|---|---|---|---|---|---|---|---|
| Ammonia Transporters | Ammonium Transporter 1.1 | AT4G13510 | AMT1.1 | 8 | | 1.43E-02 | 2.84E-04 | | |
| | Ammonium Transporter 1.2 | AT1G64780 | AMT1.2 | 1 | | | | | |
| | Ammonium Transporter 1.3 | AT3G24300 | AMT1.3 | 6 | | | 3.37E-02 | | 1.84E-03 |
| | Ammonium Transporter 1.4 | AT4G28700 | AMT1.4 | 0 | | | | | |
| | Ammonium Transporter 1.5 | AT3G24290 | AMT1.5 | 0 | | | | | |
| | Ammonium Transporter 2 | AT2G38290 | AMT2 | 5 | | 7.12E-03 | | | 8.80E-03 3.38E-02 |
| Nitrate Transporters | Nitrate Transporter 1.1 | AT1G12110 | NRT1.1 | 5 | | | | | |
| | Nitrate Transporter 1.2 | AT1G69850 | NRT1.2 | 11 | 2.89E-02 | 2.60E-06 | 1.25E-03 | | |
| | Nitrate Transporter 2.1 | AT1G08090 | NRT2.1 | 2 | | | | | |
| | Nitrate Transporter 2.2 | AT1G08100 | NRT2.2 | 1 | | | | | |
| | Nitrate Transporter 2.3 | AT5G60780 | NRT2.3 | 0 | | | | | |
| | Nitrate Transporter 2.4 | AT5G60770 | NRT2.4 | 0 | | | | | 1.56E-02 |
| | Nitrate Transporter 2.5 | AT1G12940 | NRT2.5 | 0 | | | | | |
| | Nitrate Transporter 2.6 | AT3G45060 | NRT2.6 | 3 | | 1.32E-02 | | | |
| | Nitrate Transporter 2.7 | AT5G14570 | NRT2.7 | 2 | | | | | |
| | NRT1/PTR Family 4.1 | AT3G25260 | NPF4.1 | 0 | | | | | |
| | NRT1/PTR Family 4.2 | AT3G25280 | NPF4.2 | 0 | | | | | |
| | NRT1/PTR Family 4.4 | AT1G33440 | NPF4.4 | 3 | | 1.56E-03 | | 4.31E-02 | |
| | NRT1/PTR Family 4.5 | AT1G27040 | NPF4.5 | 0 | | | | | |
| | NRT1/PTR Family 4.7 | AT5G62730 | NPF4.7 | 0 | | | | | |
| | NRT1/PTR Family 6.2 | AT2G26690 | NPF6.2 | 2 | | | | | 2.05E-02 |
| | NRT1/PTR Family 6.4 | AT3G21670 | NPF6.4 | 1 | | | | | |
| Nitrate Reductase | Nitrate Reductase 1 | AT1G77760 | NIA1 | 10 | | 1.68E-18 | 2.09E-16 | 2.80E-09 4.89E-32 | 3.77E-02 1.35E-06 |
| | Nitrate Reductase 2 | AT1G37130 | NIA2 | 19 | 8.20E-34 | | 7.38E-04 | 4.62E-03 | |
| Nitrite Reductase | Nitrite Reductase 1 | AT2G15620 | NIR1 | 9 | | | | 5.46E-13 | |
| Glutamine Synthetase | Glutamine Synthetase 1.1 | AT5G37600 | GLN1.1 | 6 | | | 4.73E-02 | 3.10E-11 | |
| | Glutamine Synthetase 1.2 | AT1G66200 | GLN1.2 | 10 | | 5.25E-10 | 1.32E-11 | 1.68E-15 | 3.53E-04 |
| | Glutamine Synthetase 1.3 | AT3G17820 | GLN1.3 | 18 | 5.95E-09 | 1.09E-02 | 1.03E-02 | 1.26E-05 2.72E-02 | |
| | Glutamine Synthetase 1.4 | AT5G16570 | GLN1.4 | 9 | | | | | |
| | Glutamine Synthetase 1.5 | AT1G48470 | GLN1.5 | 1 | | | | | |
| | Glutamine Synthetase 2 | AT5G35630 | GLN2 | 6 | | 7.56E-05 | 1.51E-04 | | 5.18E-04 |
| | Nodulin/Glutamine Synthetase-Like Protein | AT3G53180 | NODGS | 5 | | | | 4.05E-03 | |

Figure 27

| N Assimilation Step | Target Gene Full Name | Target GeneID | Target Gene Name | Target Hit Count (Root) | HHO3 (Root) Induced - 4 Repressed - 6 | ZFP4 (Root) Induced - 8 Repressed - 15 | HHO2 (Root) Induced - 9 Repressed - 11 | ERF056 (Root) Induced - 2 Repressed - 21 | HB6 (Root) Induced - 10 Repressed - 10 |
|---|---|---|---|---|---|---|---|---|---|
| Asparagine Synthetase | Asparagine Synthetase 1 | AT3G47340 | ASN1 | 13 | 1.03E-08 | 8.88E-16 | 4.75E-18 | | 1.58E-12 |
| | Asparagine Synthetase 2 | AT5G65010 | ASN2 | 1 | | | | | |
| | Asparagine Synthetase 3 | AT5G10240 | ASN3 | 1 | | | | | |
| Glutamate Synthase | Glutamate Synthase 1 | AT5G04140 | GLU1 | 2 | | | | | |
| | Glutamate Synthase 2 | AT2G41220 | GLU2 | 13 | | | | 2.94E-09 | 3.23E-04 |
| | NADH-Dependent Glutamate Synthase 1 | AT5G53460 | GLT1 | 9 | | 1.62E-02 | | 2.62E-04 | |
| Aspartate Aminotransferase | Aspartate Aminotransferase 1 | AT3G30970 | ASP1 | 9 | | 1.05E-03 | | | |
| | Aspartate Aminotransferase 2 | AT5G19550 | ASP2 | 13 | | 1.09E-02 | | 9.01E-09 | 8.76E-03 |
| | Aspartate Aminotransferase 3 | AT5G11520 | ASP3 | 8 | | 4.27E-02 | | 7.97E-12 | |
| | Aspartate Aminotransferase 4 | AT1G62800 | ASP4 | 2 | | | | 4.01E-02 | |
| | Aspartate Aminotransferase 5 | AT4G31990 | ASP5 | 16 | 3.95E-02 | 8.62E-04 | 1.24E-04 | 7.77E-11 | |
| | Aberrant Growth And Death 2 | AT2G22250 | AAT | 19 | 1.21E-04 | 3.12E-08 | 1.89E-06 | 6.60E-15 | 4.83E-08 |
| | AGD2-like Defense Response Protein | AT4G33680 | AGD2 | 6 | 1.68E-02 | 2.57E-04 | 2.84E-03 | | 3.31E-02 |
| | | AT3G13810 | ALD1 | 0 | | | | | |
| Glutamate Decarboxylase | Glutamate Decarboxylase 1 | AT5G17330 | GAD | 8 | | | | 3.08E-12 | |
| | Glutamate Decarboxylase 2 | AT1G65960 | GAD2 | 16 | | 2.42E-03 | 9.61E-05 | 4.51E-09 | |
| | Glutamate Decarboxylase 3 | AT2G02000 | GAD3 | 10 | | | | 2.71E-02 | 3.37E-02 |
| | Glutamate Decarboxylase 4 | AT2G02010 | GAD4 | 13 | | 2.57E-02 | 9.09E-03 | 2.47E-04 | 4.63E-03 |
| | Glutamate Decarboxylase 5 | AT3G17760 | GAD5 | 0 | | | | | |
| Glutamate Dehydrogenase | Glutamate Dehydrogenase 1 | AT5G18170 | GDH1 | 2 | | | | | |
| | Glutamate Dehydrogenase 2 | AT5G07440 | GDH2 | 10 | | 5.52E-09 | 1.05E-05 | | 3.49E-03 |
| | Glutamate Dehydrogenase 3 | AT3G03910 | GDH3 | 0 | | | | | |
| | Putative Glutamate Dehydrogenase | AT1G51720 | | 3 | | | | | |
| Nitrilase | Nitrilase 1 | AT3G44310 | NIT1 | 10 | 2.13E-02 | 8.42E-06 | 4.88E-03 | 6.73E-03 | 3.07E-02 |
| | Nitrilase 2 | AT3G44300 | NIT2 | 10 | 1.21E-04 | 1.03E-06 | 1.03E-06 | | 5.27E-11 |
| | Nitrilase 3 | AT3G44320 | NIT3 | 11 | | 3.85E-02 | 1.58E-04 | 4.66E-05 | 2.80E-02 |
| | Nitrilase 4 | AT5G22300 | NIT4 | 1 | | | | | |
| | Putative Nitrilase | AT4G08780 | | 0 | | | | | |
| Asparaginase | Asparaginase A1 | AT5G08100 | ASPGA1 | 0 | | | | | |
| | Putative Asparaginase | AT4G00590 | | 5 | 4.13E-02 | 8.74E-03 | 1.72E-04 | | |
| Glycolate Oxidase | 2-Hydroxy Acid Oxidase 1 | AT3G14130 | HAOX1 | 2 | | | | | |
| | 2-Hydroxy Acid Oxidase 2 | AT3G14150 | HAOX2 | 0 | | | | | |

Figure 27 (cont.)

| N Assimilation Step | Target Gene Full Name | Target Gene Name | Target GeneID | Target Gene Name | Target Hit Count (Root) | ASR3 (Root) Induced-0 Repressed-10 | SNZ (Root) Induced-7 Repressed-4 | GATA17 (Root) Induced-1 Repressed-19 | HYH (Root) Induced-3 Repressed-9 | LBD38 (Root) Induced-0 Repressed-16 | GATA17L (Root) Induced-5 Repressed-6 |
|---|---|---|---|---|---|---|---|---|---|---|---|
| Ammonia Transporters | Ammonium Transporter 1.1 | AT4G13510 | AMT1.1 | 8 | | | 1.95E-03 | 1.25E-02 | | |
| | Ammonium Transporter 1.2 | AT1G64780 | AMT1.2 | 1 | | | | | | |
| | Ammonium Transporter 1.3 | AT3G24300 | AMT1.3 | 0 | | 2.65E-02 | | | | 1.20E-02 |
| | Ammonium Transporter 1.4 | AT4G28700 | AMT1.4 | 0 | | | | | | |
| | Ammonium Transporter 1.5 | AT3G24290 | AMT1.5 | 0 | | | | | | |
| | Ammonium Transporter 2 | AT2G38280 | AMT2 | 5 | | | | | | |
| Nitrate Transporters | Nitrate Transporter 1.1 | AT1G12110 | NRT1.1 | 5 | | | 3.96E-03 | | | |
| | Nitrate Transporter 1.2 | AT1G69850 | NRT1.2 | 11 | | | 2.16E-02 | | | 4.87E-02 |
| | Nitrate Transporter 2.1 | AT1G08090 | NRT2.1 | 2 | | | | | | |
| | Nitrate Transporter 2.2 | AT1G08100 | NRT2.2 | 1 | | | | | | |
| | Nitrate Transporter 2.3 | AT5G60780 | NRT2.3 | 0 | | | | | | |
| | Nitrate Transporter 2.4 | AT5G60770 | NRT2.4 | 0 | | | | | | |
| | Nitrate Transporter 2.5 | AT1G12940 | NRT2.5 | 0 | | | | | | |
| | Nitrate Transporter 2.6 | AT3G45060 | NRT2.6 | 3 | | | | | | |
| | Nitrate Transporter 2.7 | AT5G14570 | NRT2.7 | 2 | | | | | | |
| | NRT1/PTR Family 4.1 | AT3G25260 | NPF4.1 | 0 | | | | | | |
| | NRT1/PTR Family 4.2 | AT3G25280 | NPF4.2 | 0 | | | | | | |
| | NRT1/PTR Family 4.4 | AT1G33440 | NPF4.4 | 3 | | | 3.06E-02 | | | |
| | NRT1/PTR Family 4.5 | AT1G27040 | NPF4.5 | 0 | | | | | | |
| | NRT1/PTR Family 4.7 | AT5G62730 | NPF4.7 | 0 | | | | | | |
| | NRT1/PTR Family 6.2 | AT2G26690 | NPF6.2 | 0 | | | | | | |
| | NRT1/PTR Family 6.4 | AT3G21670 | NPF6.4 | 1 | | | | | | |
| Nitrate Reductase | Nitrate Reductase 1 | AT1G77760 | NIA1 | 10 | 5.67E-04 | | 3.15E-06 | 3.32E-03 | 5.02E-05 | |
| | Nitrate Reductase 2 | AT1G37130 | NIA2 | 18 | 1.11E-05 | | 4.30E-14 | | 7.62E-06 | 1.54E-06 |
| Nitrite Reductase | Nitrite Reductase 1 | AT2G15620 | NIR1 | 9 | | | 4.64E-02 | | 3.55E-02 | |
| Glutamine Synthetase | Glutamine Synthetase 1.1 | AT5G37600 | GLN1.1 | 6 | | | 3.27E-02 | | | |
| | Glutamine Synthetase 1.2 | AT1G66200 | GLN1.2 | 10 | | | 6.64E-04 | | | |
| | Glutamine Synthetase 1.3 | AT3G17820 | GLN1.3 | 19 | 1.48E-02 | 9.68E-06 | 8.50E-13 | 4.90E-02 | 3.15E-03 | 1.48E-06 |
| | Glutamine Synthetase 1.4 | AT5G16570 | GLN1.4 | 9 | | 4.86E-02 | | | | |
| | Glutamine Synthetase 1.5 | AT1G48470 | GLN1.5 | 1 | | | | | | |
| | Glutamine Synthetase 2 | AT5G35630 | GLN2 | 6 | | | | | | |
| | Nodulin/Glutamine Synthetase Like Protein | AT3G53180 | NODGS | 5 | | | | | | |

Figure 27 (cont.)

| N Assimilation Step | Target Gene Full Name | Target GeneID | Target Gene Name | Target Hit Count (Root) | ASR3 (Root) Induced-0 Repressed-10 | SNZ (Root) Induced-7 Repressed-4 | GATA17 (Root) Induced-1 Repressed-19 | HYH (Root) Induced-3 Repressed-9 | LBD38 (Root) Induced-0 Repressed-16 | GATA17L (Root) Induced-5 Repressed-6 |
|---|---|---|---|---|---|---|---|---|---|---|
| Asparagine Synthetase | Asparagine Synthetase 1 | AT3G47340 | ASN1 | 13 | | | | | | 2.20E-08 |
| | Asparagine Synthetase 2 | AT5G65010 | ASN2 | 1 | | | | | 3.60E-02 | |
| | Asparagine Synthetase 3 | AT5G10240 | ASN3 | 1 | | | | | | |
| Glutamate Synthase | Glutamate Synthase 1 | AT5G04140 | GLU1 | 2 | | | | | 3.04E-02 | |
| | Glutamate Synthase 2 | AT2G41220 | GLU2 | 13 | | 2.34E-03 | 1.36E-08 | | 1.87E-05 | |
| | NADH-Dependent Glutamate Synthase 1 | AT5G53460 | GLT1 | 9 | 5.31E-05 | 5.93E-03 | | | 1.66E-03 | |
| Aspartate Aminotransferase | Aspartate Aminotransferase 1 | AT2G30970 | ASP1 | 9 | 8.89E-05 | | 2.97E-04 | | 8.43E-03 | |
| | Aspartate Aminotransferase 2 | AT5G19550 | ASP2 | 13 | 1.02E-02 | | 3.69E-09 | 3.80E-05 | | 5.29E-03 |
| | Aspartate Aminotransferase 3 | AT5G11520 | ASP3 | 8 | 6.35E-03 | | 3.70E-09 | | 1.03E-05 | |
| | Aspartate Aminotransferase 4 | AT1G62800 | ASP4 | 2 | | | 8.86E-06 | | | |
| | Aspartate Aminotransferase 5 | AT4G31990 | ASP5 | 16 | 1.98E-05 | | 5.88E-11 | 9.65E-04 | 1.86E-04 | |
| | Aspartate Aminotransferase | AT2G22250 | AAT | 19 | 2.15E-03 | 2.14E-04 | 2.90E-08 | 9.73E-04 | 1.80E-02 | 4.22E-07 |
| | Aberrant Growth And Death 2 | AT4G33680 | AGD2 | 6 | | 7.43E-03 | | | | |
| | AGD2-like Defense Response Protein | AT2G13810 | ALD1 | 0 | | | | | | |
| Glutamate Decarboxylase | Glutamate Decarboxylase 1 | AT5G17330 | GAD | 9 | 3.36E-04 | | 2.60E-08 | | 1.28E-02 | 1.58E-02 |
| | Glutamate Decarboxylase 2 | AT1G65960 | GAD2 | 16 | | | 1.34E-13 | 1.33E-02 | 5.02E-05 | |
| | Glutamate Decarboxylase 3 | AT2G02200 | GAD3 | 10 | | | | 2.39E-02 | | |
| | Glutamate Decarboxylase 4 | AT2G02010 | GAD4 | 13 | | | 4.04E-03 | 1.65E-02 | 3.79E-02 | |
| | Glutamate Decarboxylase 5 | AT3G17760 | GAD5 | 0 | | | | | | |
| Glutamate Dehydrogenase | Glutamate Dehydrogenase 1 | AT5G18170 | GDH1 | 2 | | | | | | |
| | Glutamate Dehydrogenase 2 | AT5G07440 | GDH2 | 10 | | | | 1.50E-02 | | |
| | Glutamate Dehydrogenase 3 | AT3G03910 | GDH3 | 0 | | | | | | |
| | Putative Glutamate Dehydrogenase | AT1G51720 | - | 3 | | | | | | |
| Nitrilase | Nitrilase 1 | AT3G44310 | NIT1 | 10 | | 2.87E-04 | | | | 1.70E-04 |
| | Nitrilase 2 | AT3G44300 | NIT2 | 10 | | 5.55E-06 | | | | 2.57E-05 |
| | Nitrilase 3 | AT3G44320 | NIT3 | 11 | | | | | | 4.74E-05 |
| | Nitrilase 4 | AT5G22300 | NIT4 | 1 | | | | | 1.72E-02 | |
| | Putative Nitrilase | AT4G08790 | - | 0 | | | | | | |
| Asparaginase | Asparaginase A1 | AT5G08100 | ASPGA1 | 5 | | 2.43E-02 | | | | |
| | Putative Asparaginase | AT4G00590 | - | 2 | | | | 4.88E-02 | | |
| Glycolate Oxidase | 2-Hydroxy Acid Oxidase 1 | AT3G14130 | HAOX1 | 2 | | | | | | |
| | 2-Hydroxy Acid Oxidase 2 | AT3G14150 | HAOX2 | 0 | | | | | | |

Figure 27 (cont.)

| N Assimilation Step | Target Gene Full Name | Target GeneID | Target Gene Name | Target Hit Count (Root) | CRF4 (Root) Induced - 3 | CRF4 (Root) Repressed - 16 | BEE2 (Root) Induced - 0 | BEE2 (Root) Repressed - 4 | ERF060 (Root) Induced - 2 | ERF060 (Root) Repressed - 13 | NAC4/NAC080 (Root) Induced - 3 | NAC4/NAC080 (Root) Repressed - 6 | TGA4 (Root) Induced - 2 | TGA4 (Root) Repressed - 8 |
|---|---|---|---|---|---|---|---|---|---|---|---|---|---|---|
| Ammonia Transporters | Ammonium Transporter 1.1 | AT4G13510 | AMT1.1 | 8 | | | | 1.43E-02 | | | | | | |
| | Ammonium Transporter 1.2 | AT1G64780 | AMT1.2 | 1 | | 2.76E-03 | | | | | | | | |
| | Ammonium Transporter 1.3 | AT3G24300 | AMT1.3 | 0 | | | | | | | | | | |
| | Ammonium Transporter 1.4 | AT4G28700 | AMT1.4 | 0 | | | | | | | | | | |
| | Ammonium Transporter 1.5 | AT3G24290 | AMT1.5 | 0 | | | | | | | | | | |
| | Ammonium Transporter 2 | AT2G38290 | AMT2 | 5 | | | | | | | | | | |
| Nitrate Transporters | Nitrate Transporter 1.1 | AT1G12110 | NRT1.1 | 5 | 7.06E-09 | | | | | | | | | |
| | Nitrate Transporter 1.2 | AT1G69850 | NRT1.2 | 11 | | | | | | | 3.45E-05 | | 3.08E-04 | |
| | Nitrate Transporter 2.1 | AT1G08090 | NRT2.1 | 2 | 7.97E-04 | | | | | | | | | |
| | Nitrate Transporter 2.2 | AT1G08100 | NRT2.2 | 1 | 1.85E-02 | | | | | | | | | |
| | Nitrate Transporter 2.3 | AT5G60780 | NRT2.3 | 0 | | | | | | | | | | |
| | Nitrate Transporter 2.4 | AT5G60770 | NRT2.4 | 0 | | | | | | | | | | |
| | Nitrate Transporter 2.5 | AT1G12940 | NRT2.5 | 0 | | | | | | | | | | |
| | Nitrate Transporter 2.6 | AT3G45060 | NRT2.6 | 3 | 7.94E-07 | | | | | | | | | |
| | Nitrate Transporter 2.7 | AT5G14570 | NRT2.7 | 2 | | | | | | | | | | |
| | NRT1/PTR Family 4.1 | AT3G25260 | NPF4.1 | 0 | | | | | | | | | | |
| | NRT1/PTR Family 4.2 | AT3G25280 | NPF4.2 | 0 | | | | | | | | | | |
| | NRT1/PTR Family 4.4 | AT1G33440 | NPF4.4 | 3 | | | | | | | | | | |
| | NRT1/PTR Family 4.5 | AT1G27040 | NPF4.5 | 0 | | | | | | | | | | |
| | NRT1/PTR Family 4.7 | AT5G63790 | NPF4.7 | 0 | | | | | | | | | | |
| | NRT1/PTR Family 6.2 | AT2G26690 | NPF6.2 | 2 | | | | | | | | | | |
| | NRT1/PTR Family 6.4 | AT3G21670 | NPF6.4 | 1 | | | | | | | | | | |
| Nitrate Reductase | Nitrate Reductase 1 | AT1G77760 | NIA1 | 10 | 8.48E-09 | | | | 1.06E-12 | | | | | |
| | Nitrate Reductase 2 | AT1G37130 | NIA2 | 18 | 2.23E-03 | | | | 6.78E-09 | | | 2.98E-02 | | |
| Nitrite Reductase | Nitrite Reductase 1 | AT2G15620 | NIR1 | 9 | 2.00E-04 | | | | 4.21E-03 | | | | | |
| Glutamine Synthetase | Glutamine Synthetase 1.1 | AT5G37600 | GLN1.1 | 6 | 3.04E-03 | | | | | | | | 2.86E-02 | |
| | Glutamine Synthetase 1.2 | AT1G66200 | GLN1.2 | 10 | 4.87E-02 | | | | 5.58E-03 | | | 2.08E-02 | 1.93E-02 | |
| | Glutamine Synthetase 1.3 | AT3G17820 | GLN1.3 | 18 | | | | | | | | | 1.39E-05 | |
| | Glutamine Synthetase 1.4 | AT5G16570 | GLN1.4 | 9 | | | | | | | | | | |
| | Glutamine Synthetase 1.5 | AT1G48470 | GLN1.5 | 1 | | | | | | | | | | |
| | Glutamine Synthetase 2 | AT5G35630 | GLN2 | 6 | | | | | | | | | | |
| | Nodulin/Glutamine Synthetase-Like Protein | AT3G53180 | NODGS | 5 | 2.32E-17 | | | | | | 7.44E-06 | | | |

Figure 27 (cont.)

| N Assimilation Step | Target Gene Full Name | Target GeneID | Target Gene Name | Target Hit Count (Root) | CRF4 (Root) Induced-3 Repressed-16 | BEE2 (Root) Induced-0 Repressed-4 | ERF060 (Root) Induced-2 Repressed-13 | NAC4/NAC080 (Root) Induced-3 Repressed-6 | TGA4 (Root) Induced-2 Repressed-8 |
|---|---|---|---|---|---|---|---|---|---|
| Asparagine Synthetase | Asparagine Synthetase 1 | AT3G47340 | ASN1 | 13 | | | | | |
| | Asparagine Synthetase 2 | AT5G65010 | ASN2 | 1 | 4.81E-02 | | | | |
| | Asparagine Synthetase 3 | AT5G10240 | ASN3 | 1 | 7.15E-06 | | | | |
| Glutamate Synthase | Glutamate Synthase 1 | AT5G04140 | GLU1 | 2 | 4.71E-02 | | 1.65E-05 | 2.55E-02 | |
| | Glutamate Synthase 2 | AT2G41220 | GLU2 | 13 | 9.95E-05 | | 6.46E-04 | | |
| | NADH-Dependent Glutamate Synthase 1 | AT5G53460 | GLT1 | 9 | | | 2.85E-02 | | |
| Aspartate Aminotransferase | Aspartate Aminotransferase 1 | AT2G30970 | ASP1 | 9 | | | | | |
| | Aspartate Aminotransferase 2 | AT5G19550 | ASP2 | 13 | | 2.55E-02 | | | 9.78E-05 |
| | Aspartate Aminotransferase 3 | AT5G11520 | ASP3 | 8 | | | 2.48E-04 | | |
| | Aspartate Aminotransferase 4 | AT1G62800 | ASP4 | 2 | 3.91E-03 | | | | |
| | Aspartate Aminotransferase 5 | AT4G31990 | ASP5 | 16 | 3.46E-02 | | 4.74E-03 | 9.18E-04 | 6.90E-07 |
| | Aspartate Aminotransferase | AT2G22250 | AAT | 19 | | 6.14E-03 | 4.39E-02 | | |
| | Aberrant Growth And Death 2 | AT4G33680 | AGD2 | 6 | | | | | |
| | AGD2-like Defense Response Protein | AT3G13810 | ALD1 | 0 | | | | | |
| Glutamate Decarboxylase | Glutamate Decarboxylase 1 | AT5G17330 | GAD | 8 | 9.85E-04 | | 1.41E-04 | | 1.05E-03 |
| | Glutamate Decarboxylase 2 | AT1G65960 | GAD2 | 18 | | | 6.33E-03 | 3.35E-02 | 9.35E-03 |
| | Glutamate Decarboxylase 3 | AT2G02000 | GAD3 | 10 | | 2.9TE-02 | 4.79E-02 | | 1.11E-02 |
| | Glutamate Decarboxylase 4 | AT2G02010 | GAD4 | 13 | | | | | |
| | Glutamate Decarboxylase 5 | AT3G17760 | GAD5 | 0 | | | | | |
| Glutamate Dehydrogenase | Glutamate Dehydrogenase 1 | AT5G18170 | GDH1 | 2 | | | | | |
| | Glutamate Dehydrogenase 2 | AT5G07440 | GDH2 | 10 | 2.37E-02 | | | | 8.95E-05 |
| | Glutamate Dehydrogenase 3 | AT3G03910 | GDH3 | 0 | | | | | |
| | Putative Glutamate Dehydrogenase | AT1G51720 | | 3 | | | 3.05E-02 | 1.33E-02 | |
| Nitrilase | Nitrilase 1 | AT3G44310 | NIT1 | 10 | | | | | |
| | Nitrilase 2 | AT3G44300 | NIT2 | 10 | | | | | |
| | Nitrilase 3 | AT3G44320 | NIT3 | 11 | 3.31E-02 | | | 5.15E-05 | |
| | Nitrilase 4 | AT5G22300 | NIT4 | 1 | | | | | |
| | Putative Nitrilase | AT4G09790 | | 0 | | | | | |
| Asparaginase | Asparaginase A1 | AT5G08100 | ASPGA1 | 0 | | | | | |
| | Putative Asparaginase | AT4G00580 | | 5 | | | | | |
| Glycolate Oxidase | 2-Hydroxy Acid Oxidase 1 | AT3G14130 | HAOX1 | 2 | | | | | |
| | 2-Hydroxy Acid Oxidase 2 | AT3G14150 | HAOX2 | 0 | | | | | |

Figure 27 (cont.)

| N Assimilation Step | Target Gene Full Name | Target GeneID | Target Gene Name | TargetHit Count (Root) | C2H2 (Root) Induced-7 Repressed-19 | bZIP3 (Root) Induced-5 Repressed-17 | bZIP1 (Root) Induced-2 Repressed-13 | COL5 (Root) Induced-8 Repressed-10 | HSFB2A (Root) Induced-4 Repressed-21 | CDF1 (Root) Induced-9 Repressed-8 |
|---|---|---|---|---|---|---|---|---|---|---|
| Ammonia Transporters | Ammonium Transporter 1.1 | AT4G13510 | AMT1.1 | 8 | 1.63E-13 | | | 2.85E-02 | 8.09E-12 | |
| | Ammonium Transporter 1.2 | AT1G64780 | AMT1.2 | 1 | | | | | | 5.08E-03 |
| | Ammonium Transporter 1.3 | AT3G24300 | AMT1.3 | 6 | | 1.34E-02 | | | | |
| | Ammonium Transporter 1.4 | AT4G28700 | AMT1.4 | 0 | | | | | | |
| | Ammonium Transporter 1.5 | AT3G24290 | AMT1.5 | 0 | | | | | | |
| | Ammonium Transporter 2 | AT2G38290 | AMT2 | 5 | 4.74E-03 | | | 1.04E-03 | 1.05E-03 | |
| Nitrate Transporters | Nitrate Transporter 1.1 | AT1G12110 | NRT1.1 | 5 | | | 2.23E-04 | 1.01E-02 | | |
| | Nitrate Transporter 1.2 | AT1G69850 | NRT1.2 | 11 | 1.07E-17 | 2.78E-04 | | 6.02E-03 | 1.17E-31 | |
| | Nitrate Transporter 2.1 | AT1G08090 | NRT2.1 | 2 | 1.37E-02 | | | | | |
| | Nitrate Transporter 2.2 | AT1G08100 | NRT2.2 | 1 | | | | | | |
| | Nitrate Transporter 2.3 | AT5G60780 | NRT2.3 | 0 | | | | | | |
| | Nitrate Transporter 2.4 | AT5G60770 | NRT2.4 | 0 | | | | | | |
| | Nitrate Transporter 2.5 | AT1G12940 | NRT2.5 | 0 | | | | | | |
| | Nitrate Transporter 2.6 | AT3G45060 | NRT2.6 | 3 | | | | | 7.41E-04 | |
| | Nitrate Transporter 2.7 | AT5G14570 | NRT2.7 | 2 | | | | | 2.05E-02 | |
| | NRT1/PTR Family 4.1 | AT3G25260 | NPF4.1 | 0 | | | | | | |
| | NRT1/PTR Family 4.2 | AT3G25280 | NPF4.2 | 0 | | | | | | |
| | NRT1/PTR Family 4.4 | AT1G33440 | NPF4.4 | 3 | | | | | | |
| | NRT1/PTR Family 4.6 | AT1G27040 | NPF4.6 | 0 | | | | | | |
| | NRT1/PTR Family 4.7 | AT5G62730 | NPF4.7 | 0 | | | | | | |
| | NRT1/PTR Family 6.2 | AT2G26690 | NPF6.2 | 2 | | | | 4.81E-02 | | |
| | NRT1/PTR Family 6.4 | AT3G21670 | NPF6.4 | 1 | | | | 1.02E-08 | | |
| Nitrate Reductase | Nitrate Reductase 1 | AT1G77760 | NIA1 | 10 | 4.60E-22 | 4.16E-05 | 5.55E-11 | 6.46E-09 | 2.97E-02 | |
| | Nitrate Reductase 2 | AT1G37130 | NIA2 | 16 | | 4.35E-31 | 3.07E-05 | | 7.46E-22 | 6.77E-14 |
| Nitrite Reductase | Nitrite Reductase 1 | AT2G15620 | NIR1 | 9 | | 1.96E-06 | 1.90E-06 | | 3.81E-03 | |
| Glutamine Synthetase | Glutamine Synthetase 1.1 | AT5G37600 | GLN1.1 | 6 | | | 4.11E-04 | | 8.76E-09 | |
| | Glutamine Synthetase 1.2 | AT1G66200 | GLN1.2 | 10 | | | 4.16E-07 | | 2.22E-02 | 2.09E-09 |
| | Glutamine Synthetase 1.3 | AT3G17820 | GLN1.3 | 16 | 1.87E-05 | 1.51E-12 | | 1.12E-06 | 1.25E-16 | 1.53E-07 |
| | Glutamine Synthetase 1.4 | AT5G16570 | GLN1.4 | 8 | 2.99E-04 | 3.13E-07 | 4.58E-03 | 6.72E-04 | 1.60E-02 | |
| | Glutamine Synthetase 1.5 | AT1G48470 | GLN1.5 | 1 | | | | | | |
| | Glutamine Synthetase 2 | AT5G35630 | GLN2 | 6 | 5.94E-06 | | | 2.10E-02 | | |
| | Nodulin/Glutamine Synthetase-Like Protein | AT3G53180 | NODGS | 5 | 2.14E-02 | 1.41E-03 | | | | 2.40E-08 |

Figure 27 (cont.)

| N Assimilation Step | Target Gene Full Name | Target GeneID | Target Gene Name | Target Hit Count (Root) | C2H2 (Root) Induced-7 Repressed-18 | bZIP3 (Root) Induced-5 Repressed-17 | bZIP1 (Root) Induced-2 Repressed-13 | COL5 (Root) Induced-8 Repressed-10 | HSFB2A (Root) Induced-4 Repressed-21 | CDF1 (Root) Induced-9 Repressed-8 |
|---|---|---|---|---|---|---|---|---|---|---|
| Asparagine Synthetase | Asparagine Synthetase 1 | AT3G47340 | ASN1 | 13 | 1.36E-13 | 4.30E-13 | 2.84E-13 | 2.45E-03 | 2.43E-03 | 4.19E-21 |
| | Asparagine Synthetase 2 | AT5G65010 | ASN2 | 1 | | | | | | |
| | Asparagine Synthetase 3 | AT5G10240 | ASN3 | 1 | | | | | | |
| Glutamate Synthase | Glutamate Synthase 1 | AT5G04140 | GLU1 | 2 | | | | | | |
| | Glutamate Synthase 2 | AT2G41220 | GLU2 | 13 | 4.65E-02 | 4.20E-02 | | 3.43E-02 | 1.61E-10 | |
| | NADH-Dependent Glutamate Synthase 1 | AT5G53460 | GLT1 | 8 | 1.85E-08 | | | | | |
| Aspartate Aminotransferase | Aspartate Aminotransferase 1 | AT2G30970 | ASP1 | 9 | 2.37E-05 | 1.80E-05 | 6.10E-04 | | 9.51E-03 | 2.70E-02 |
| | Aspartate Aminotransferase 2 | AT5G19550 | ASP2 | 13 | 3.08E-02 | 7.41E-03 | 6.07E-07 | | 1.96E-08 | |
| | Aspartate Aminotransferase 3 | AT5G11520 | ASP3 | 8 | 3.84E-02 | | | | 4.59E-08 | |
| | Aspartate Aminotransferase 4 | AT1G62800 | ASP4 | 2 | | | | | | |
| | Aspartate Aminotransferase 5 | AT4G31990 | ASP5 | 16 | 8.47E-05 | 5.34E-09 | 1.52E-06 | | 2.23E-13 | |
| | Aspartate Aminotransferase | AT2G22250 | AAT | 19 | 4.89E-13 | 3.09E-15 | 1.30E-08 | 7.72E-06 | 1.09E-15 | 2.64E-08 |
| | Aberrant Growth And Death 2 | AT4G33680 | AGD2 | 6 | | | | | | 4.18E-02 |
| | AGD2-like Defense Response Protein 1 | AT2G13810 | ALD1 | 0 | | | | | | |
| Glutamate Decarboxylase | Glutamate Decarboxylase 1 | AT5G17330 | GAD | 8 | 4.34E-02 | 1.69E-03 | | 1.95E-04 | | |
| | Glutamate Decarboxylase 2 | AT1G65960 | GAD2 | 16 | 2.58E-03 | 4.06E-05 | 3.77E-05 | | 1.66E-04 | 7.40E-04 |
| | Glutamate Decarboxylase 3 | AT2G02000 | GAD3 | 10 | | 8.09E-06 | 4.65E-02 | 2.80E-03 | 3.35E-07 | 7.54E-03 |
| | Glutamate Decarboxylase 4 | AT2G02010 | GAD4 | 13 | | 6.58E-11 | | 1.38E-03 | 1.40E-10 | 8.88E-04 |
| | Glutamate Decarboxylase 5 | AT3G17760 | GAD5 | 0 | | | | | | |
| Glutamate Dehydrogenase | Glutamate Dehydrogenase 1 | AT5G18170 | GDH1 | 2 | | | | | | |
| | Glutamate Dehydrogenase 2 | AT5G07440 | GDH2 | 10 | 8.29E-13 | 1.16E-15 | 7.87E-41 | | 2.08E-02 | 4.12E-02 |
| | Glutamate Dehydrogenase 3 | AT3G03910 | GDH3 | 0 | | | | | | 6.06E-08 |
| | Putative Glutamate Dehydrogenase | AT1G51720 | - | 3 | 6.87E-03 | | | | | |
| Nitrilase | Nitrilase 1 | AT3G44310 | NIT1 | 10 | 9.34E-03 | 4.45E-03 | | 1.80E-02 | 1.50E-02 | 2.30E-03 |
| | Nitrilase 2 | AT3G44300 | NIT2 | 10 | 3.77E-07 | 4.02E-02 | | 8.37E-04 | | 4.11E-12 |
| | Nitrilase 3 | AT3G44320 | NIT3 | 11 | 6.33E-03 | | | | 8.78E-06 | 2.75E-05 |
| | Nitrilase 4 | AT5G22300 | NIT4 | 1 | | | | | | |
| | Putative Nitrilase | AT4G08790 | - | 0 | | | | | | |
| Asparaginase | Asparaginase A1 | AT5G08100 | ASPGA1 | 0 | | | | | | |
| | Putative Asparaginase | AT4G00590 | - | 5 | | | | | | |
| Glycolate Oxidase | 2-Hydroxy Acid Oxidase 1 | AT3G14130 | HAOX1 | 2 | 7.22E-03 | 5.88E-03 | | | | |
| | 2-Hydroxy Acid Oxidase 2 | AT3G14150 | HAOX2 | 0 | | | | | | |

Figure 27 (cont.)

| N Assimilation Step | Target Gene Full Name | Target GeneID | Target Gene Name | Target Hit Count (Shoot) | TGA1 (Shoot) Induced-0 | TGA1 (Shoot) Repressed-27 | HHO5 (Shoot) Induced-4 | HHO5 (Shoot) Repressed-7 | HHO6 (Shoot) Induced-6 | HHO6 (Shoot) Repressed-4 | PHL1 (Shoot) Induced-15 | PHL1 (Shoot) Repressed-2 | CDF1 (Shoot) Induced-15 | CDF1 (Shoot) Repressed-6 | SNZ (Shoot) Induced-19 | SNZ (Shoot) Repressed-2 | CRF4 (Shoot) Induced-5 | CRF4 (Shoot) Repressed-17 |
|---|---|---|---|---|---|---|---|---|---|---|---|---|---|---|---|---|---|---|
| Ammonia Transporters | Ammonium Transporter 1.1 | AT4G13510 | AMT1.1 | 1 | | | | | | | | 5.50E-03 | | | | | | |
| | Ammonium Transporter 1.2 | AT1G64780 | AMT1.2 | 1 | | | | | | | | | | | | | | 3.50E-03 |
| | Ammonium Transporter 1.3 | AT3G24300 | AMT1.3 | 0 | | | | | | | | | | | | | | |
| | Ammonium Transporter 1.4 | AT4G28700 | AMT1.4 | 1 | | | | | | | | 1.87E-05 | | | | | | |
| | Ammonium Transporter 1.5 | AT3G24290 | AMT1.5 | 0 | | | | | | | | | | | | | | |
| | Ammonium Transporter 2 | AT2G38290 | AMT2 | 2 | | | | | | | | | | 3.34E-03 | | 8.18E-03 | | |
| Nitrate Transporters | Nitrate Transporter 1.1 | AT1G12110 | NRT1.1 | 3 | | 9.53E-04 | 1.51E-03 | | | | | | | | | | | 5.33E-03 |
| | Nitrate Transporter 1.2 | AT1G69850 | NRT1.2 | 3 | | 4.19E-09 | | | | | | | | 9.17E-03 | | 4.39E-20 | | 3.03E-03 |
| | Nitrate Transporter 2.1 | AT1G08090 | NRT2.1 | 6 | | 0.004523909 | | | | | | 6.95E-03 | | 7.64E-04 | | | | 1.95E-03 |
| | Nitrate Transporter 2.2 | AT1G08100 | NRT2.2 | 2 | | 8.17E-07 | | | | | | | | | | | | 6.37E-03 |
| | Nitrate Transporter 2.3 | AT5G60780 | NRT2.3 | 2 | | 2.18E-02 | | | | | | | | | | | | |
| | Nitrate Transporter 2.4 | AT5G60770 | NRT2.4 | 0 | | | | | | | | | | | | | | |
| | Nitrate Transporter 2.5 | AT1G12940 | NRT2.5 | 2 | | | | | | | | 8.17E-80 | | 3.46E-02 | | | | 1.83E-08 |
| | Nitrate Transporter 2.6 | AT3G45060 | NRT2.6 | 1 | | | | | | | | | | | | | | |
| | Nitrate Transporter 2.7 | AT5G14570 | NRT2.7 | 0 | | | | | | | | | | | | | | |
| | NRT1/PTR Family 4.1 | AT3G25260 | NPF4.1 | 0 | | | | | | | | | | | | | | |
| | NRT1/PTR Family 4.2 | AT3G25280 | NPF4.2 | 0 | | | | | | | | | | | | | | |
| | NRT1/PTR Family 4.4 | AT1G35440 | NPF4.4 | 0 | | | | | | | | | | | | | | |
| | NRT1/PTR Family 4.5 | AT1G27040 | NPF4.5 | 0 | | | | | | | | | | | | | | |
| | NRT1/PTR Family 4.7 | AT5G62730 | NPF4.7 | 1 | | | | | | | | 3.32E-05 | | | | | | |
| | NRT1/PTR Family 6.2 | AT2G26690 | NPF6.2 | 1 | | | | | | | | | | | | | | 3.46E-02 |
| | NRT1/PTR Family 6.4 | AT3G21670 | NPF6.4 | 1 | | | | | | | | | | | | | | 3.84E-03 |
| Nitrate Reductase | Nitrate Reductase 1 | AT1G77760 | NIA1 | 4 | | 3.92E-11 | | | | | | 8.83E-188 | | 8.88E-37 | | 1.75E-24 | | 6.10E-04 |
| | Nitrate Reductase 2 | AT1G37130 | NIA2 | 4 | | 2.04E-25 | | | | 8.10E-17 | | | | 4.21E-02 | | 1.40E-04 | | 2.80E-16 |
| Nitrite Reductase | Nitrite Reductase 1 | AT2G15620 | NiR1 | 6 | | 2.52E-14 | | | | 1.64E-16 | | 8.83E-188 | | 1.48E-39 | | 4.21E-11 | | 2.31E-02 |
| Glutamine Synthetase | Glutamine Synthetase 1.1 | AT5G37600 | GLN1.1 | 5 | | 9.68E-10 | | | | | | 8.83E-188 | | 6.32E-109 | | 3.81E-04 | | 2.31E-02 |
| | Glutamine Synthetase 1.2 | AT1G68500 | GLN1.2 | 3 | | 1.99E-06 | | | | | | | | | | 2.18E-04 | | 1.58E-02 |
| | Glutamine Synthetase 1.3 | AT3G17820 | GLN1.3 | 3 | | 2.02E-11 | 4.57E-03 | | | | | | | 3.01E-05 | | | | |
| | Glutamine Synthetase 1.4 | AT5G16570 | GLN1.4 | 2 | | 4.32E-04 | | | | | | 7.18E-07 | | | | | | |
| | Glutamine Synthetase 1.5 | AT1G48470 | GLN1.5 | 0 | | | | | | | | | | | | | | |
| | Glutamine Synthetase 2 | AT5G35630 | GLN2 | 1 | | | | | | | | | | | | 7.80E-02 | | |
| | Nodulin/Glutamine Synthetase-like Protein | AT3G53180 | NODGS | 3 | | | | | | | | 5.46E-26 | | 8.07E-06 | | 4.31E-03 | | 5.33E-44 |

NITROGEN RESPONSIVE TRANSCRIPTION FACTORS IN PLANTS

CROSS REFERENCE TO RELATED APPLICATIONS

This application claims priority to U.S. Provisional Applications Nos. 62/523,505, filed on Jun. 22, 2017, and 62/587,167, filed Nov. 16, 2017, the disclosures of which are incorporated herein by reference.

STATEMENT REGARDING FEDERALLY SPONSORED RESEARCH

This invention was made with government support under contract numbers GM032877 and GM095273 awarded by the National Institutes of Health, and 1339362 awarded by the National Science Foundation. The government has certain rights in the invention.

BACKGROUND OF THE DISCLOSURE

Nitrogen (N) is a key nutrient and signaling molecule and has been shown to mediate changes in dynamic processes in the plant life-style, including the regulation of the circadian clock and root nutrient foraging. Nitrogen supplied as fertilizer is a core component of modern agriculture. While a net positive in alleviating world-wide human hunger, the application of synthetic fertilizers comes at significant environmental cost, particularly through excess nitrogen run-off due to inefficient N-use efficiency by crops.

Therefore, a pressing goal for sustainable, yet high-yield agriculture, is the improvement of plant nitrogen (N) uptake, assimilation and utilization. With this goal in mind, previous studies have attempted to capture and model the regulatory networks controlling N-uptake/assimilation. Studies, have identified a relatively small number of Transcription Factors (TFs) as key regulators of N-signaling that mediates N-uptake/assimilation and root responses; these include NLP7 (Marchive et al., Nat Commun 4, 1713, (2013)), HRS1 (Medici et al., Nat Commun 6, 6274, (2015)), TGA1/4 (Alvarez, J. M. et al., Plant J 80, 1-13, (2014)), TCP20 (Guan et al., Proc Natl Acad Sci USA 114, 2419-2424, (2017)), etc. However, most prior studies of N-signaling in plants have been performed at only one or two time-points following N-treatment (Wang et al., Plant Physiol 132, 556-567, (2003); Wang et al., Plant Physiol 136, 2512-2522, (2004); Canales et al., Front Plant Sci 5, 22, (2014)). One fine-scale time-series study addressed the very early N-cascade (from 3-20 min), to identify the immediate nitrate-response genes in the roots, where the N-signal is initially perceived (Krouk et al., Genome Biol 11, R123 (2010)). Despite these insights about individual TFs, a comprehensive overview of the regulatory network and the hierarchy within which these TFs—and as yet unknown TFs—function alone and in combination in mediating N-signaling is lacking. The likely presence of regulatory loops (e.g., NLP7 regulates HRS1 and both regulate NRT1.1 (Medici et al., Nat Commun 6, 6274, (2015)), and protein interactions involving these TFs (e.g., TCP family interacts with NLP family (Guan et al., Proc Natl Acad Sci USA 114, 2419-2424, (2017)), confounds attempts to determine the linear transduction of the external N-signal into the N-uptake and assimilation processes.

SUMMARY OF THE DISCLOSURE

This disclosure provides a method for identifying regulatory network of transcription factors that are responsive to Nitrogen, and provides dynamic interactions between different transcription factors, and transcription factors and other target genes.

In one aspect, this disclosure provides a method for modulating Nitrogen (N) uptake/assimilation and/or usage in a plant cell or a plant comprising over-expressing or under-expressing one or more N-responsive transcription factors (TF) that are described herein. One or more TFs may be over-expressed or underexpressed, or a combination of overexpression of some TFs and underexpression (repression) of some TFs may be used to achieve increased or decreased Nitrogen uptake and assimilation as desired. For example, one or more target genes (as shown in FIG. 27) may be induced or repressed by inducing or repressing one or more TFs that directly, or indirectly, induce or repress the particular target gene. The under-expressing (also referred to herein as repression or repressing) of a TF may comprise disrupting a polynucleotide sequence (such as by editing (e.g., using CRISPR), or using RNAi) that encodes or controls expression of the TF, or inhibiting translation of an mRNA that encodes the TF. The over-expression of a TF may comprise introducing a recombinant polynucleotide sequence that encodes for the TF linked to a suitable promoter.

In one embodiment, the disclosure provides a method for modulating Nitrogen (N) uptake/assimilation and/or usage in plant cell or a plant comprising over-expressing or under-expressing TFs, such as, CRF4, SNZ, CDF1, HHO5, HHO6 and/or PHL1. For example, if it desired to increase N uptake or assimilation (such as under normal or low nitrogen environment), the TF CRF4 can be under-expressed, which can result in increased N uptake and/or assimilation. Additionally, or independently, the expression of SNZ and/or CDF1 may be induced, which will further increase N uptake and/or assimilation. In another example, if decrease in N-uptake and/or assimilation is desired (to conserve N resources, such as under low-N), the method may comprise overexpression of CRF4, and under-expression of SNZ and CDF1 (See FIG. 6A). In an embodiment, overexpression of one or more of HHO5, HHO6, PHL1, and TGA1 can be carried out, which will result in increased N uptake and/or assimilation (see FIG. 27). The logic for how the TF combinations will affect genes involved in N-uptake and assimilation can be derived from FIG. 27. This figure shows the effect of overexpression of each TF on the target genes in the N-uptake/assimilation pathway. For example, for each TF, the figure indicates if the gene is induced, repressed or has no effect. This information can be used to determine which TFs to use in combination to affect changes in the target genes in the N-uptake/assimilation pathway, and which direction to effect the change (e.g. TF overexpression or repression). For example if a target gene in the N-uptake/assimilation pathway is to be induced, one or more TFs that induce the gene can be over expressed, and/or one or more TFs that repress the gene can be underexpressed. Conversely, if a target gene in the N-uptake/assimilation pathway is to be repressed, one or more TFs that induce the gene can be under-expressed, and/or one or more TFs that repress the gene can be over-expressed.

The method is applicable to any plant. For example, the plant may be a species of woody, ornamental, decorative, crop, cereal, fruit, or vegetable plant.

In one aspect, this disclosure provides a transgenic plant or a plant cell comprising a polynucleotide encoding a TF described herein. The TF is operably linked to a promoter with activity in plants. The promoter can be a constitutive or inducible promoter, or may be associated with a constitutive or inducible regulatory element.

In one embodiment, this disclosure provides a transgenic plant or plant cell comprising a recombinant polynucleotide sequence encoding a TF CRF4, SNZ, CDF1, HHO5, HHO6 and/or PHL1 operably linked to a plant promoter. A transgenic plant or plant cell may comprise a plurality of recombinant polynucleotide sequences encoding a plurality of TFs selected from the group consisting of the TFs described in FIG. 6, FIG. 7, or FIG. 27, each recombinant polynucleotide operably linked to a plant promoter, which may be the same or different from the promoters for the other recombinant polynucleotides introduced into the transgenic plant or plant cell.

In one embodiment, the disclosure provides a transgenic plant or plant cell comprising a recombinant polynucleotide encoding a TF CRF4, and the TF is operably linked to a first promoter with activity in plants. The transgenic plant may further comprise a second recombinant polynucleotide encoding SNZ or CDF1 operatively linked to a second promoter. The first and the second promoters can be the same or different. In one embodiment, the transgenic plant may comprise recombinant polynucleotides encoding CRF4, SNZ and/or CDF1, each linked to a promoter, which promoter may be the same or different from the other promoters (if more than one of CRF4, SNZ and CDF1 are present).

In one embodiment, this disclosure provides a transgenic plant or plant cell comprising a polynucleotide or polynucleotides, each polynucleotide encoding HHO5, HHO6, and PHL1, and optionally additionally TGA1, each polynucleotide encoding a TF being operably linked to a promoter, which promoter may be the same or different from the other promoters for the other TFs.

In one aspect, this disclosure provides a product derived from the transgenic plant or plant cell into which has been introduced a polynucleotide encoding a TF described herein. The TF is operably linked to a promoter with activity in plants. The promoter can be a constitutive or inducible promoter, or may be associated with a constitutive or inducible regulatory element.

In one aspect, this disclosure provides an isolated nucleic acid molecule comprising a full length cDNA sequence that is identical to a sequence encoding a N-responsive TF of a plant cell described herein, or is at least 85% identical to such sequence.

In one aspect, this disclosure provides a recombinant nucleic acid construct comprising in the 5 to 3' direction a promoter operable in a plant cell, and nucleic acid molecule which encodes or is complementary to a molecule which encodes a transcription factor described herein such that the nucleic acid molecules is positioned downstream from the promoter and operably linked therewith.

In one aspect, this disclosure provides a vector comprising a recombinant nucleic acid construct as described herein.

In one aspect, this disclosure provides a seed or crop, or a progeny thereof of a transgenic plant described herein.

In one aspect, this disclosure provides a method for identifying transcription factors that are activated in response to a specific external stimulus comprising: exposing a biological material to the external stimulus; at predetermined times following exposure, generating transcriptome profiles; comparing transcriptome profiles to controls (which have not been exposed to the external stimulus), thereby identifying genes first expressed at each time and generating time bin sets representing first genes expressed at that time; generating "just-in-time" bins for each time, each just-in-time bin representing exclusive sets of genes first substantially regulated by the external stimulus; for each "just-in-time" bin gene set, evaluating all promoters for all genes in the gene set to identify cis-binding motifs that are over-represented and evaluating all genes for significant enrichment of Gene Ontology (GO) terms; and using machine learning algorithm and using time-series data, identifying stimulus-responsive transcription factors that regulate downstream TFs or target genes.

In one aspect, this disclosure provides a method of identifying cis-binding motifs that are activated in response to a specific external stimulus comprising: exposing a biological material to the external stimulus; at predetermined times following exposure, generating transcriptome profiles; comparing transcriptome profiles to controls (which have not been exposed to the external stimulus), thereby identifying genes first expressed at each time and generating time-bin sets representing first genes expressed at that time; generating "just-in-time" bins for each time, each just-in-time bin representing exclusive sets of genes first substantially regulated by the external stimulus; for each "just-in-time" bin gene set, evaluating all promoters for all genes in the gene set to identify cis-binding motifs that are over-represented, and optionally, obtaining a temporal activation pattern of all cis-binding motifs that are activated in response to the specific external stimulus.

BRIEF DESCRIPTION OF THE FIGURES

FIG. 7. Table showing TFs in the N-regulatory DFG network with genome-wide TF-DNA binding data display a significant "N-specificity" index. Of the 40 TFs in the DFG network supported by independent in vitro TF-DNA binding data (DAP-Seq), this list of 19 TFs listed have a high "N-specificity index". The "N-specificity index" of each TF was calculated by comparing the proportion of TF-bound targets in the N×Time gene set in shoots (2,172 genes) ($p_n$), to the proportion of the TF-bound targets in the whole genome ($p_g$) based on independent TF-target binding in vitro (DAP-Seq data). Those TFs with a significant over-representation of their bound targets in the N×Time response gene set (p-val <0.01) are shown here. This list of TFs with a significant N-specificity index includes four TFs (NLP7, TGA1/4 and NAC4) that were previously validated in N-signaling in plants. Our GRN for the dynamic N-regulatory network thus uncovered 15 novel N-specific TFs, including CRF4, which is validated herein by TF perturbation assays (FIG. 5) and in planta (FIG. 6).

FIG. 14. Functional category (GO term) enrichment at each "Just-in-time" point. Each N-signal response genes was assigned to a "just-in-time" bin which is the time-point at which that gene first shows a fold change (FC) greater that 1.5 between the gene expression level in the N-treated samples and the control samples. Next, each "just-in-time" geneset was analyzed by the BioMaps function in Virtual-Plant (Katari et al., Plant Physiol, 2010. 152(2): p. 500-15) (virtualplant.org) to identify over represented GO terms in each bin.

FIG. 1. Modifications to the TARGET system enable increased throughput of TF screening. Two major changes were made to the TARGET system which enable the screening of 8 TFs/Day. First, we now used an additional GFP reporter, which allows us to transfect two populations of protoplasts separately, one with the original RFP containing vector, and the other with the new GFP containing vector. Transfected cells are then pooled divided into 3 wells on a treatment plate where they receive Dex and/or nitrogen. Fluorescent Activated Cell Sorting (FACS) is used to efficiently separate the GFP and RFP expressing protoplasts, each of which contain a different GR-TF fusion. The second modification is the transfection of batches of protoplasts with multiple GR-TF fusions (up to 8 per day) and an Empty Vector (EV). This allows each individual TF to be compared pairwise to an EV control in order to determine differentially expressed genes.

FIG. 2. Selection process for the initial 23 TFs screened by the improved TARGET system. The first set of TFs we screened were chosen by selecting TFs that responded to nitrogen in both the shoot and root Nitrogen by Time network (Example 2). We also biased our selection of TFs towards those that respond early (5-10 min) and those with a high N-specificity index, highlighted as bolded and italicized as calculated in Example 2.

FIG. 22. Genes targeted by 10 or more of the 23 TFs are enriched in many N-related GO-terms. Binning of the 120, 094 TF-targets was done by how many TFs influence their expression (FDR <0.05). GO-Term analysis was done on the combined set of 1047 genes that are targeted by 10 or more TFs (bolded). Terms associated with nitrogen signaling and metabolism, such as amino acid metabolism, nitrogen compound biosynthesis and root development are enriched in this set of genes.

FIG. 23. Combining TF-regulation (TARGET) and TF-binding (DAP-Seq) uncovers cis-motifs involved in gene induction or repression. Of the 23 TFs for which targets were identified in our TARGET experiments, 10 are also found in the DAP-Seq dataset (O'Malley et al. 2016) and 9 of those (bolded) had a high N-specificity index (Example 2). The number of genes in the overlap between the TF-regulated (TARGET) and TF-bound (DAP-Seq) targets is shown and the p-value calculated for this overlap was used to shade the cells green. Elefinder was used to look for the enrichment of the DAP-Seq motif reported in O'Malley et al. in the 1 kb promoters of target genes found for the Top 1500 peaks from DAP-Seq, the induced target genes and repressed target genes for each TF. Cells shaded grey have a significant enrichment of the DAP-motif, compared to the background of all 1 kb promoters for genes.

FIG. 27. Table shows regulation of the N assimilation pathways by the 26 TARGET TFs. Genes involved in N assimilation are divided into the different steps of N uptake and conversion into the organic form. For each gene in the pathway (rows) the number of TFs, in roots and shoots, affecting that gene are reported (Target Hit Count) and the p-value and sign of the influence (dark grey=induced, light grey with hatching=repressed) is reported in the appropriate columns If there is no effect on that gene the cell is white. The total number of induced and repressed target genes in the pathways is also reported for each TF. The TFs are HHO3, ZFP4, HHO2, ERF056, HB6, ASR3, SNZ, GATA17, HYH, LBD38, GATA17L, CRF4, BEE2, ERF060, NAC4NAC080, TGA4, C2H2, bZIP3, bZIP1, COLS, HSFB2A, CDF1, TGA1, HHO5, HHO6, and PHL1.

DETAILED DESCRIPTION OF THE DISCLOSURE

Figure 1:
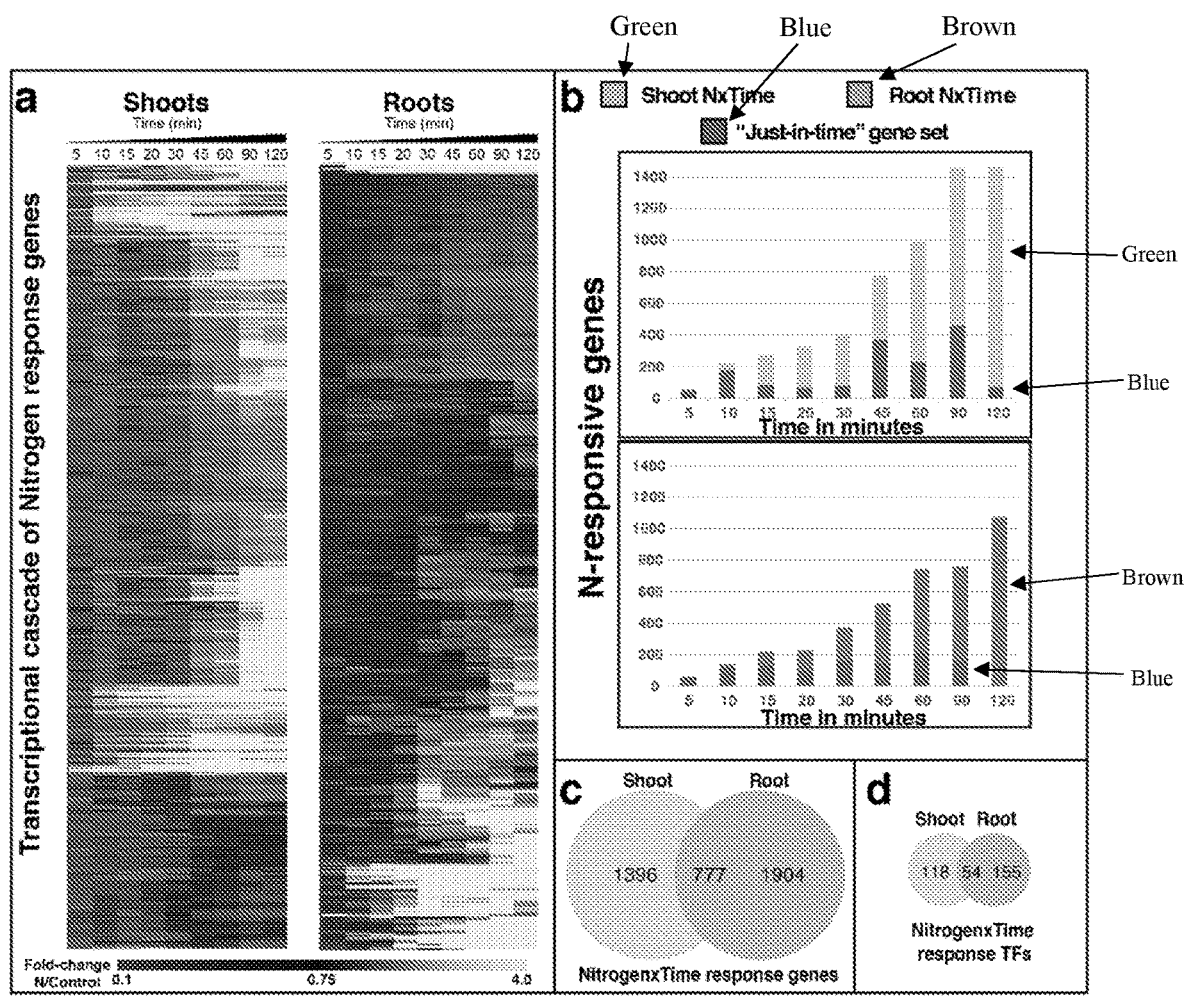
FIG. 1. Dynamic N-signaling & "just-in-time" gene set analysis identifies a temporal cascade of N-response genes. a. The transcriptional cascade triggered by N-signal perception of nitrate and ammonia sources shows a sequential activation and repression of genes in shoots and roots. b. The transcriptional response to these N-sources increases over time in shoots (green bars) and roots (brown bars); "Just-in-time" gene sets (blue bars) uses a "classification" algorithm to capture cohorts of genes whose expression is altered by the N-signal for the first time at that specific time-point (FIG. 13c). c. The shoot and root transcriptional response to the N-signals includes both shared and organ-specific responses. d. The shared and organ-specific responses to the N-signals are also seen within the subset of responsive Transcription Factors (TFs).

This disclosure provides a method for identifying regulatory network of N-responsive transcription factors and dynamic interactions between the transcription factors as well as with other target genes in the genome, including ones involved in nitrogen uptake from the soil and assimilation into the N-storage/transport amino acids glutamine/glutamate and asparagine. The disclosure also provides compositions relating to the N-responsive TFs and their targets, such as compositions comprising recombinant nucleic acid constructs, cDNAs, vectors and the like. The disclosure also provides plant cells and plants in which the transcription factors have been modulated to effect desirable effects on the regulation of genes in the N-uptake/assimilation pathway and N-related growth characteristics.

In this disclosure, we describe a method to uncover a previously hidden cascade of cis-elements underlying dynamic N-signaling, using a "just-in-time" analysis of N-response time-series transcriptome data. This time-series dataset was also used to learn the amplitude, cadence and regulatory interactions of 327 transcription factors (TFs) in shoots and roots with some being expressed in shoots or roots alone (Table 4). Some of the TF-target interactions indicated by time-based network inference, were supported using independent TF-target binding datasets which were also used to calculate a TF "N-specificity" index. The many Feed-Forward Loops (FFLs) of predicted TF interactions reveal temporal relationships of validated N-signaling TFs, and new TFs were also uncovered. These FFLs now provide the combinatorial logic for TF-perturbations to improve N-use efficiency in plants. In this disclosure, for example, we teach which of the N-responsive TFs target genes in the N-uptake/assimilation pathway—as listed in Table 3. In one embodiment, these TFs can be prioritized. Moreover, this time-based approach can uncover the temporal "transcriptional logic" for any biological response system of interest.

The present disclosure relates to N-responsive transcription factors that control N-uptake/assimilation and other related processes in response to N-availability and/or treatment. Several novel transcription factors are identified and regulatory interactions between the novel and known TFs involved in N-responses are also described providing an understanding of the dynamic N-signaling response in plants. The present disclosure provides compositions and methods which can be used to effect over-expression or under-expression of individual TFs, or combinations of TFs identified as part of FFLs using our approach. The present disclosure also provides plant cells and plants which have been modified to effect over-expression or under-expression of individual TFs, or combinations of TFs to manipulate their response to N availability and treatment.

The TFs of the present disclosure include any TF that is referenced in the description (including tables) or in the figures. Examples of TFs include those listed in Tables 1, 2, 3 and 4, and FIG. 27. A TF may be identified by a name or a Gene ID number. A TF also includes a sequence that is at least 85%, 90%, 95% or 99% or any value from 85 to 99% identical to a sequence, and functionally equivalent thereto, of a TF that is referenced herein.

A TF sequence or the sequence for any other gene is intended to include a polynucleotide sequence that encodes it and an amino acid sequence for the protein. The nucleotide and amino acid sequences associated with each GeneID referenced in this disclosure, available from public database (e.g., arabidopsis.org) as of the filing date of U.S. Provisional application No. 62/523,505, (filed on filed on Jun. 22, 2017) are incorporated herein by reference.

This disclosure also provides a method of identifying temporal relationships between TFs and for determining when the TFs are first induced in an N-response (e.g. "Just-in-Time" analysis, and for identifying relationships of TFs in the form of Feed-Forward Loops (FFLs) and other relationships. A method to calculate an "N-specificity index" for each TF in the network is also provided. This information can be used to identify TFs involved in the N-response whose manipulation in planta will improve N-use efficiency in plants, including under stress conditions, such as reduced N availability.

Figure 3:
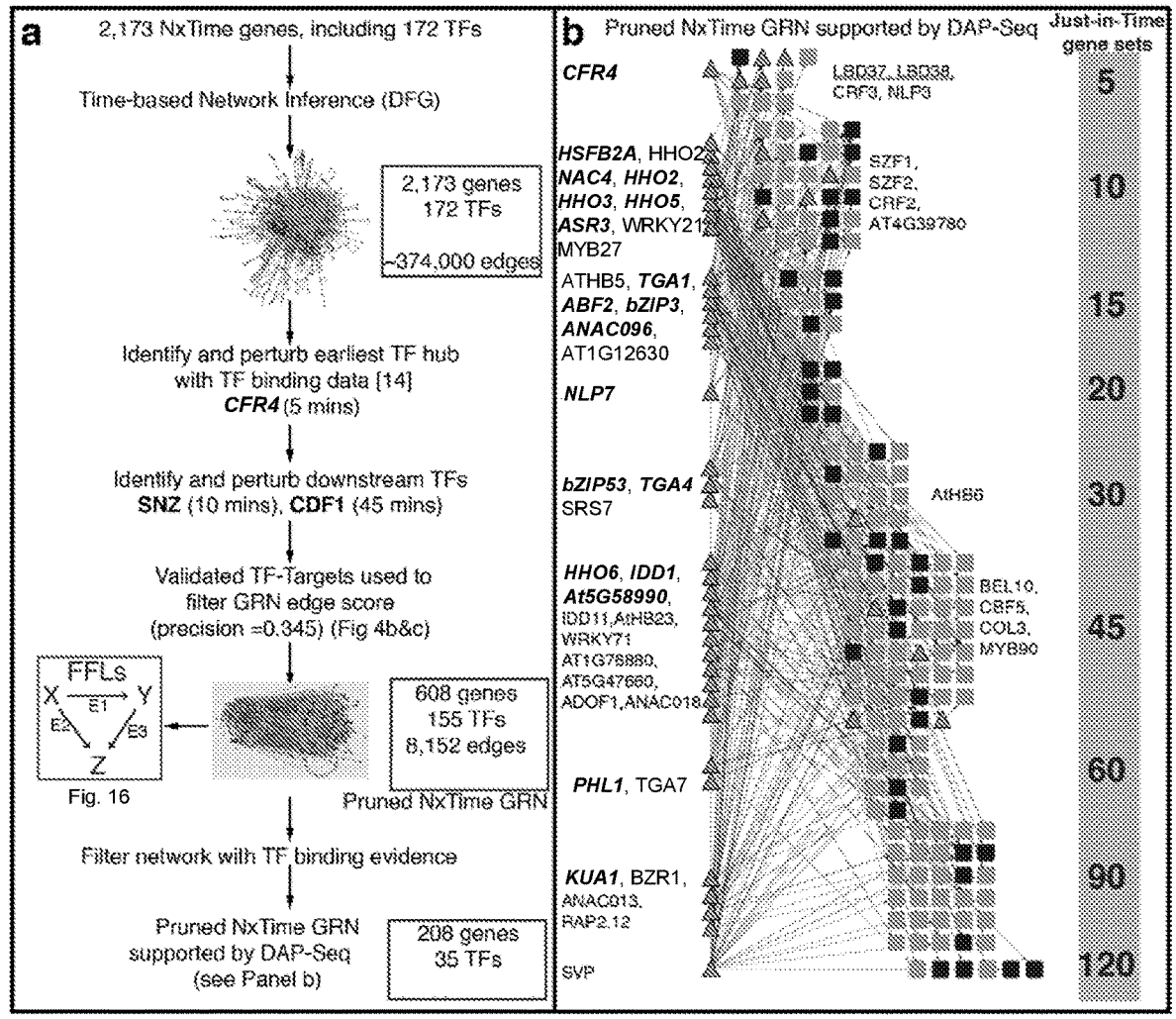
FIG. 3. A time-dependent DFG-inferred Gene Regulatory Network (GRN) in the dynamic N-signaling cascade. a. A time-based machine learning approach Dynamic Factor Graph (DFG) (Krouk et al., Genome Biol, 2010. 11(12): p. R123; Mirowski et al., Machine Learning and Knowledge Discovery in Databases: European Conference, ECML PKDD 2009, Bled, Slovenia, Sep. 7-11, 2009, Proceedings, Part II, W. Buntine, et al., Editors. 2009, Springer Berlin Heidelberg: Berlin, Heidelberg. p. 128-143) was used to infer TF-Target activation and repression. Validation studies of 3 TFs in the GRN (CRF4 and its validated downstream targets SNZ and CDF1) were used to "prune" the DFG-inferred network for precision (FIG. 4a). To do this, the predicted TF-target edges in the network were trimmed at 0.345 precision (see AUPR curve in FIG. 4b & c). b. DFG-Predicted TF-target edges also supported by an independent source of genome-wide TF-Target binding data (DAP-Seq (O'Malley et al., Cell, 2016. 166(6): p. 1598). This refined time-based GRN for N-signaling includes 208 N-responsive genes regulated by 35 TFs. The TFs with a significant "N-specificity" index (FIG. 7) are italicized and bolded. This GRN in Panel b is limited to TFs that are in the DAP-Seq database (O'Malley et al., Cell, 2016. 166(6): p. 1598). Validated TF regulators of N-metabolism are underlined NLP7 (Marchive et al., Nat Commun, 2013. 4: p. 1713), TGA1/4 (Alvarez et al., Plant J, 2014. 80(1): p. 1-13), NAC4 (Vidal et al., Plant Signal Behav, 2014. 9(3): p. e28501), LBD37,38 (Rubin et al., Plant Cell, 2009. 21(11): p. 3567-84.), CRF4 (present disclosure).
Figure 11:
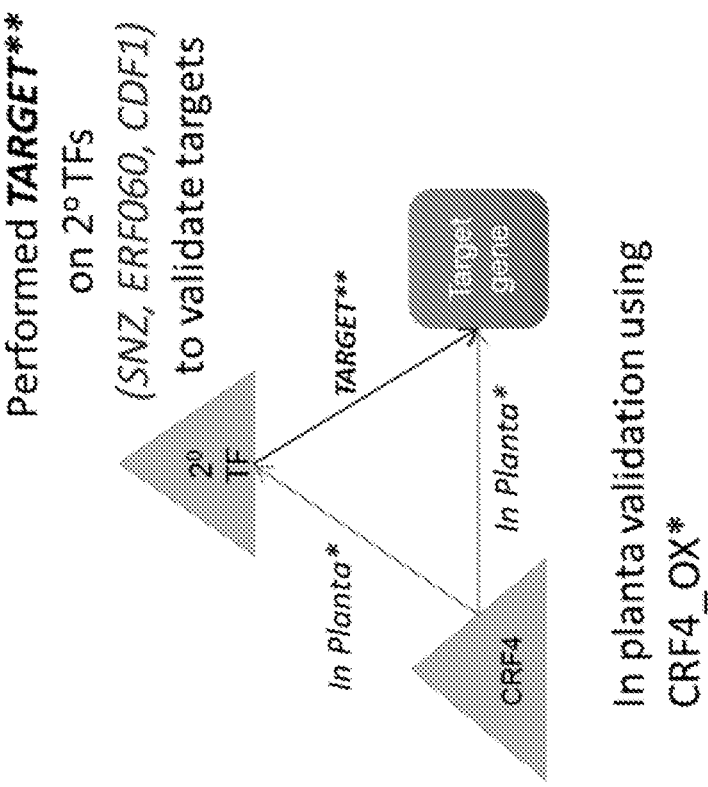
FIG. 11. CRF4 in planta validated targets include 1209 genes in the genome, include 67 TF targets. 16/67 TF targets of CRF4_OX are also responsive to N×TIME. 16 TFs targeted by CRF4 that are regulated by N×TIME=(AAR1, At5G58900, ZRF1A, SZF1, BEL10, ANAC036, AGL22, SNZ, ERF060, ANAC072, LBD37, DOF1, MYBL2, HD2A, CDF1, SZF2). Three TFs italicized: SNZ, ERF060, and CDF1 were overexpressed in plant cells using TARGET system (Bargmann et al., Mol Plant 6, 978-980, (2013)) to determine their genome-wide targets (Example 3). This data was used to make a network connecting all experimentally validated targets of CRF4 (in planta), SNZ, ERF060 and CDF1 (in plant cells). The targets in the N-assimilation pathway are shown in FIG. 12.
Figure 12:
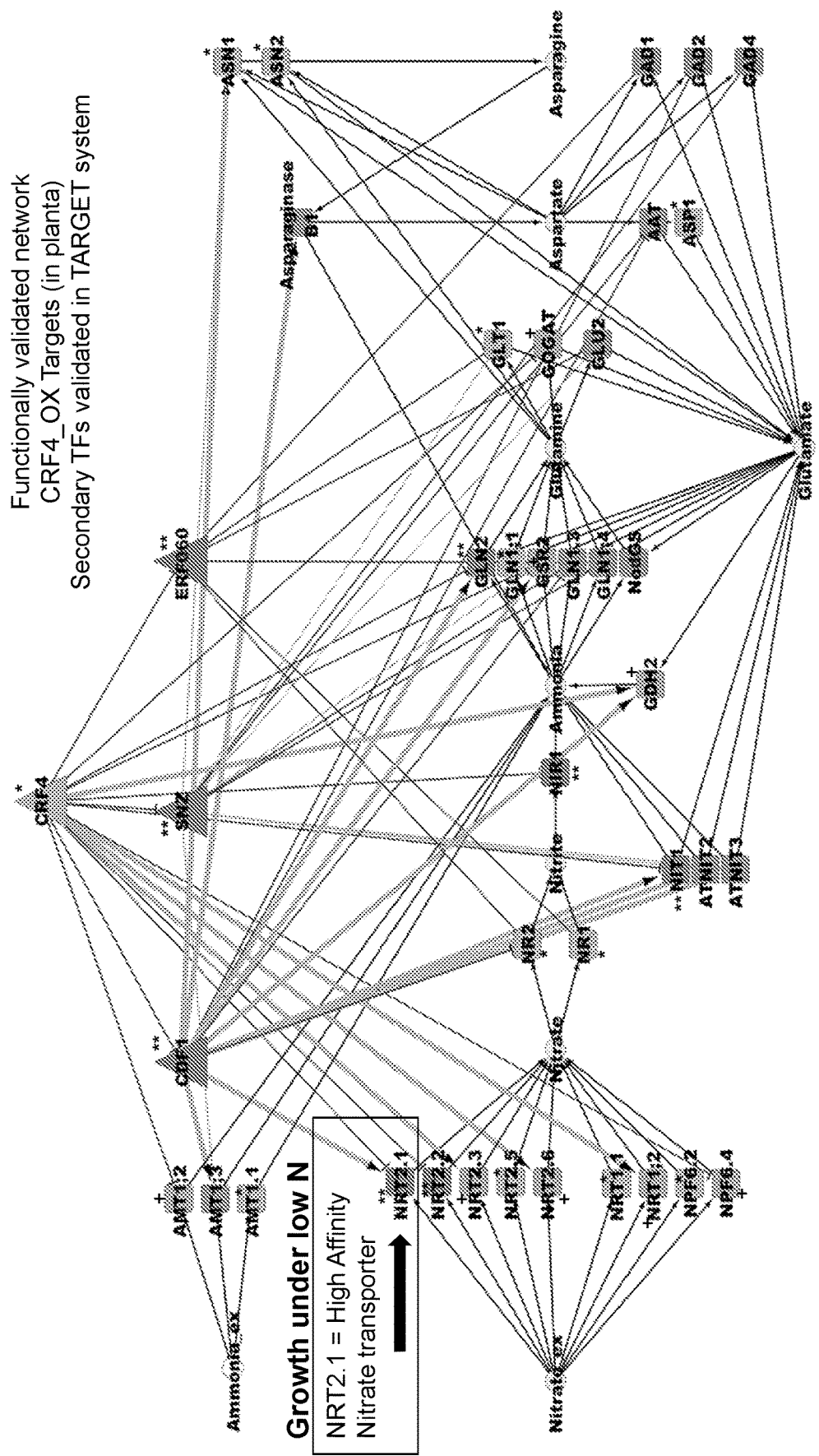
FIG. 12. Experimentally validated targets of CRF4, CDF1, SNZ, and ERF060 in the N-uptake assimilation pathway. CRF4 targets validated in planta using CRF4_OX (see Example 2). In planta CRF4 targets in the N-uptake/assimilation in shoots or roots. Targets of CDF1, SNZ, and ERF060 were experimentally validated in the cell based TARGET system. Validated targets of CDF1, SNZ, and ERF060 in the N-assimilation pathway are shown in FIG. 27. All N-uptake/assimilation targets validated to be regulated by CRF4 in planta, or by CDF1, SNZ or ERF060 in plant cells are shown in a network view constructed with cytoscape. Nodes with **=genes regulated by TFs and responsive to N×TIME. Nodes with +=genes regulated by TFs but not regulated in N×TIME data. Nodes with *=genes regulated by N×TIME but not regulated by TFs. Nodes with no symbol=genes regulated by the TF2s i.e., CDF1 or SNZ or ERF060. Solid thick line (edge) TF to gene target=validated induction; Solid thin line TF (edge) to gene target=validated repression. TFs are triangles, target genes in N-assimilation=rounded squares.
Figure 13:
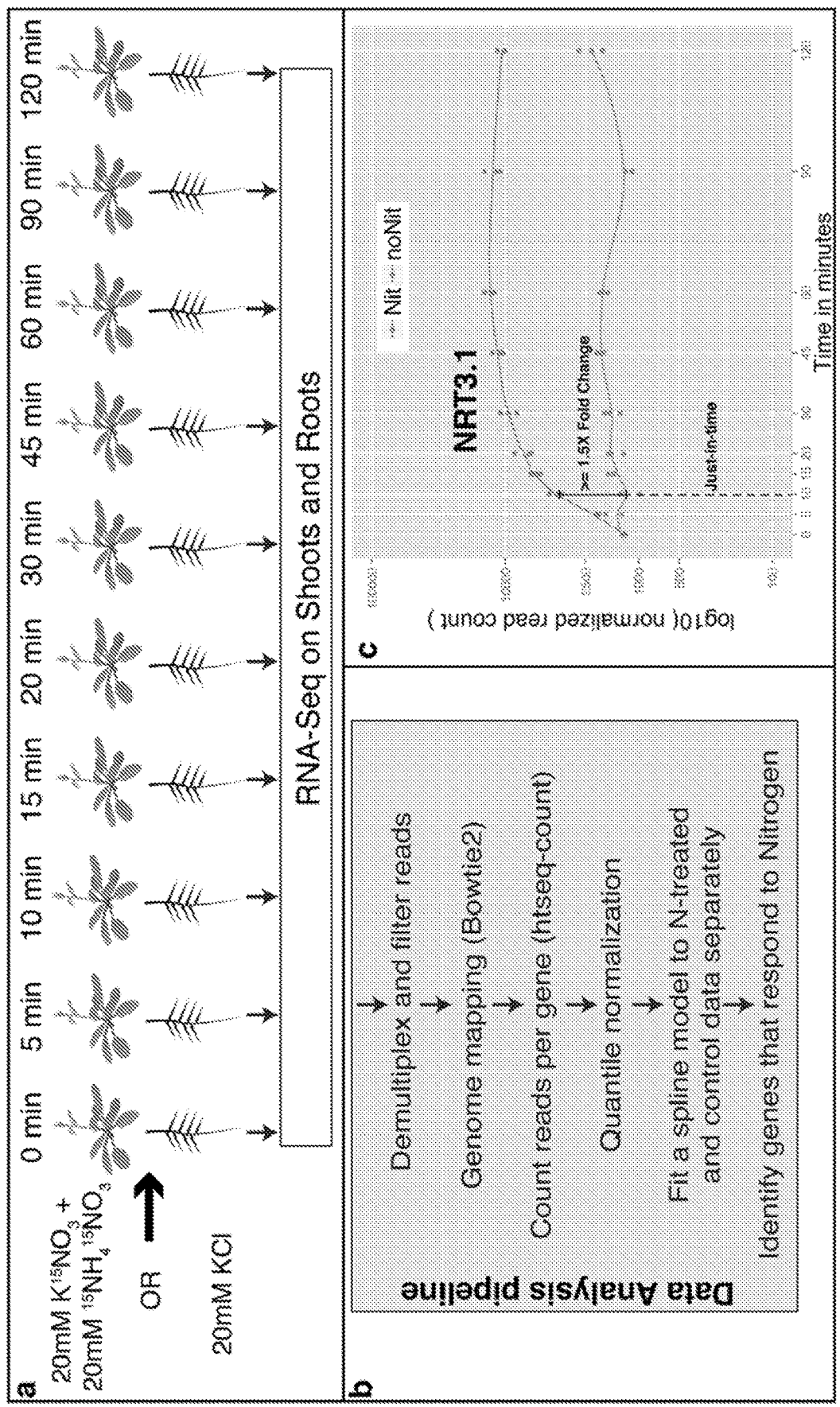
FIG. 13. A fine-scale time-series profile of plant transcriptional changes in response to N-supply. a. Three replicates of plants grown in a hydroponic system under N sufficient conditions (1 mM KNO3), were treated with either 60 mM nitrogen (20 mM KNO3+20 mM NH4NO3) or 20 mM KCl and harvested at time intervals 0, 5, 10, 15, 20, 30, 45, 60, 90, and 120 minutes after treatment. Roots and shoots from three independent Phytatray experiments were harvested separately at each time-point, and their transcriptome assayed using the RNA-Seq protocol on the Illumina sequencing platform. b. The resultant RNA-Seq data was filtered for quality and redundancy and converted into gene expression measures using the informatics pipeline shown. Genes responsive to the N-signal were identified by fitting the gene expression measures to a cubic spline model and testing for significant difference (FDR<0.01) between the N-treated and control fits (refer to method section that describes spline analysis) c. For example, a significant increase in the mRNA level of a nitrate transporter NRT3.1 was observed within 10 minutes of the N-supply. The "Just-in-Time" classification for this gene is 10 minutes since it is the first time point at which the fold-change (FC) is >=1.5, between gene expression in Nitrogen treated and control samples.
Figure 19:
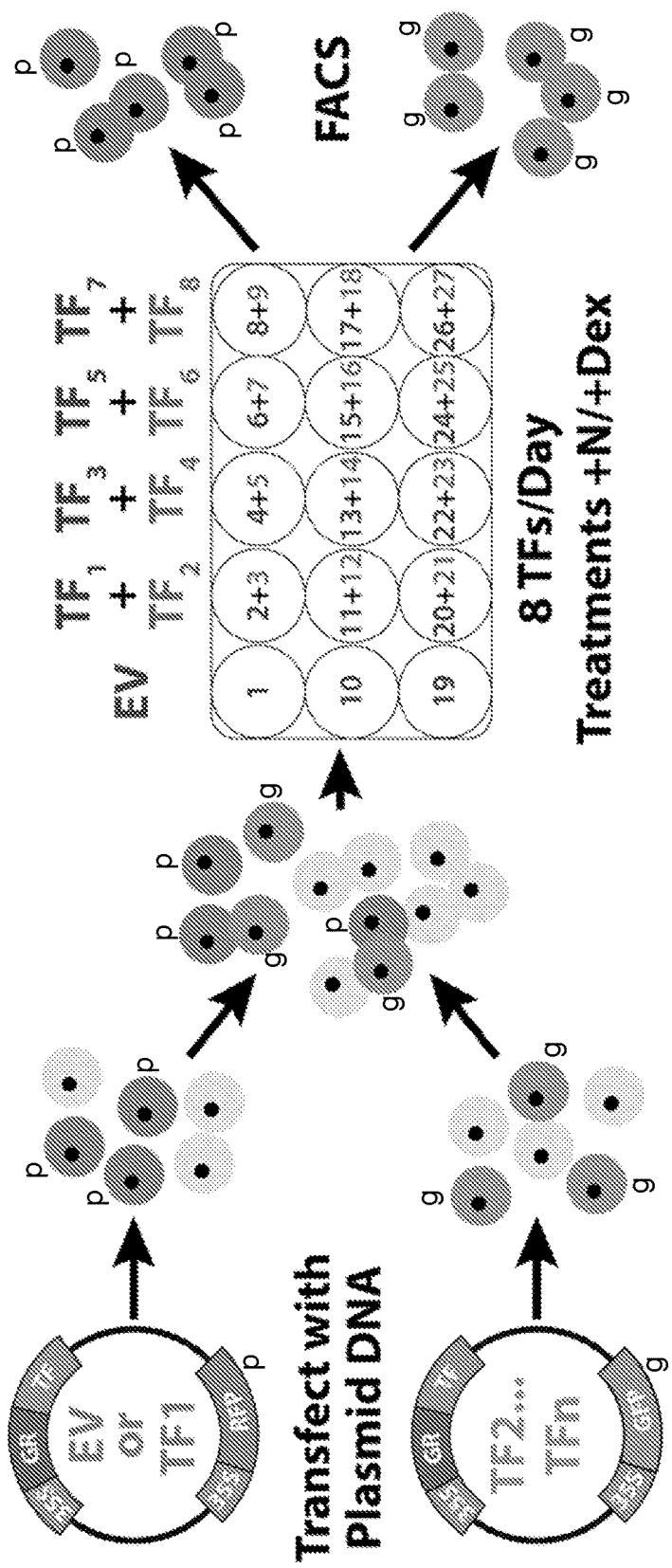
FIG. 19.

We describe a method to select TFs for testing alone and in combination (see Example 1). We provide such a proof-of-principle example of a FFL identified in the present disclosure as an early-responder TF, CRF4 (responds to N-treatment within 5 min), which was validated herein to affect N-use in planta in Example 2 (FIG. 3). We identified the CRF4 target genes by conditionally overexpressing CRF4 in planta. Conditional overexpression of the first-responder TF, CRF4, perturbed an incoherent FFL (FIG. 10) that represses the high-affinity nitrate transporter (NRT2.1), reducing biomass specifically under low-N (FIG. 13). We also functionally validated three TFs validated to act downstream of CRF4 (CDF1, SNZ and ERF060). We did this in a plant cell system called TARGET for TF overexpression (FIG. 19). We then assembled the TF-targets validated for CRF4 in plant shoots, validated targets for CDF1, SNZ, and ERF060 (Example 3) as network connections shown in FIG. 11. We specifically then made a subnetwork of targets in N-uptake/assimilation pathway. This enabled us to identify all the validated targets for CRF4, SNZ, ERF060 and CDF1, shown to affect the expression of genes in the N-assimilatory pathway (FIG. 12). This method was also used to show that other TFs are validated to share common targets with CRF4 including bZIP3 and HHO3 (FIG. 3). A list of all N-responsive TFs that target genes in the N-uptake/assimilation pathway is shown in Table 3 (23) below.

Figure 27:
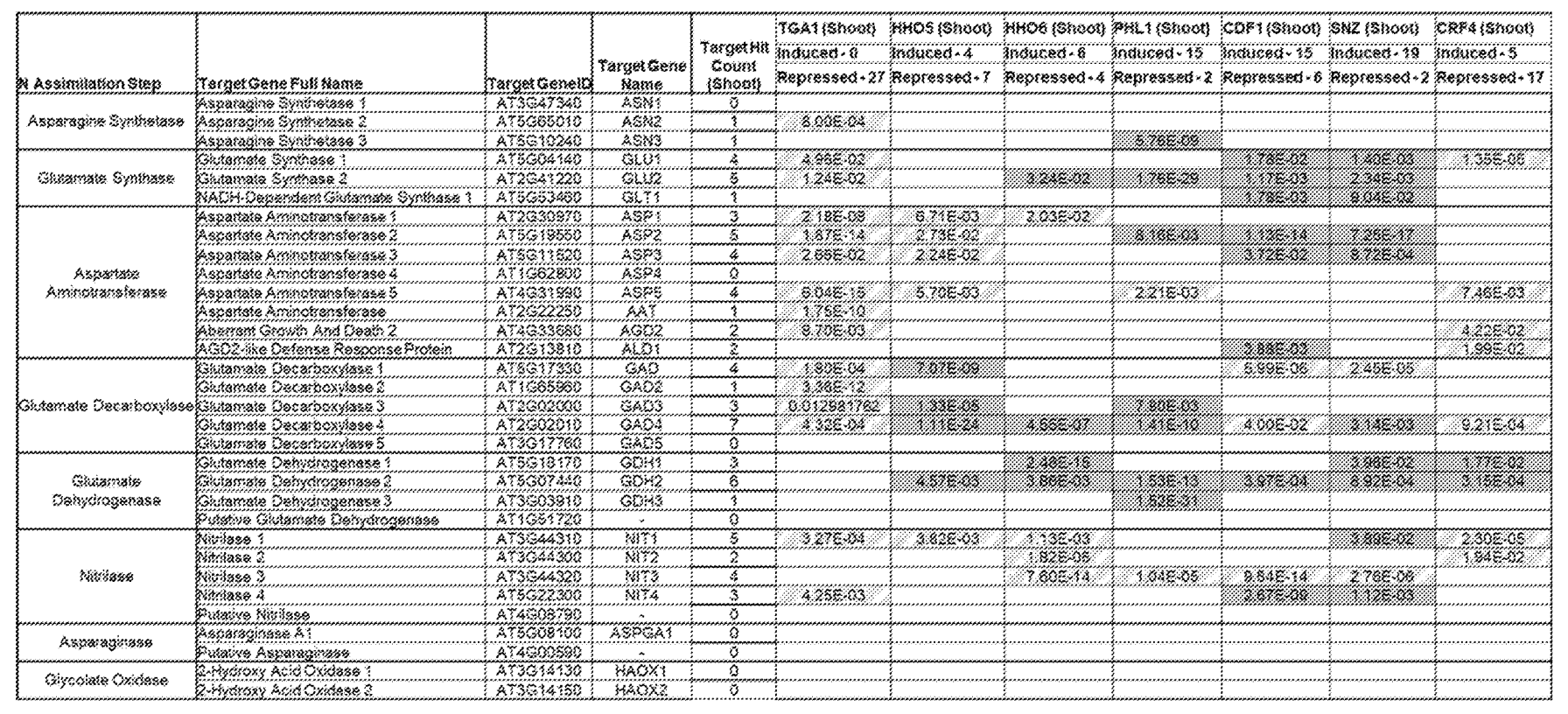

In another example, targets for four TFs, HHO5, HHO6, PHL1, and TGA1 were validated and their effects on the expression of genes in the N-uptake/assimilation pathway were identified (FIG. 27). All the 4 TFs were found to be positive regulators of genes involved in N-uptake and assimilation, thereby improving N uptake and assimilation.

In one embodiment, this disclosure provides a method for altering nitrogen assimilation and/or usage in a plant cell comprising under-expressing or overexpressing in the plant one or more TFs identified herein. Also provided is a method for reducing or improving nitrogen uptake-assimilation and/or usage in a plant in which less or more nitrogen is available for biosynthesis, said method comprising overexpressing or under-expressing one or more TFs in the plant. When more than one TFs are used, one or more TFs may be under-expressed, while other one or more TFs may be over-expressed to achieve the goal of reducing or increasing N-uptake/assimilation and/or usage under conditions of low, normal or high nitrogen availability.

The overexpression of a particular gene can be accomplished by any method known in the art. For example, a plant cell may be transformed with a nucleic acid vector comprising the coding sequences of the desired gene operably linked to a promoter active in a plant cell such that the desired gene is expressed at levels higher than normal (i.e., levels found in a control/nontransgenic plant). The promoters can be constitutively active in all or some plant tissues or can be inducible.

The under-expression of a desired gene can be accomplished by any method known in the art. For example, a gene may be knocked out, or mutated such that lower than normal levels of the gene product is produced in the transgenic cells or plant. For example, such mutations include frame-shift mutations or mutations resulting in a stop codon in the wild-type coding sequence, thus preventing expression of the gene product. Another exemplary mutation would be the removal of the transcribed sequences from the plant genome, for example, by homologous recombination. Another method for under-expressing a gene is transgenically introducing an insertion or deletion into the transcribed sequence or an insertion or deletion upstream or downstream of the transcribed sequence such that expression of the gene product is decreased as compared to wild-type or appropriate control. Additionally, microRNA (native or artificial) can be used to target a particular encoding mRNA for degradation, thus reducing the level of the expressed gene product in the transgenic plant cell. Another method for underexpression of a gene of interest is using CRISPR gene inactivation.

The present disclosure also provides compositions for modulating gene expression in plants, in particular gene expressions of TFs. The compositions comprise constructs for the expression of or suppression of the TFs. For example, a construct of the disclosure comprises a promoter, such as a tissue specific and/or inducible promoter, which is expressed in a plant cell, such as a leaf cell, a shoot cell, a root cell and the like, and promotes the expression of the TF. The compositions may comprise microRNAs or CRISPR constructs for suppressing the expression of one or more TFs. Any of a variety of promoters can be used in the constructs of the disclosure depending on the desired outcome. Tissue-specific or tissue-preferred promoters, inducible promoters, developmental promoters, constitutive promoters, constitutive promoters and/or chimeric promoters can be used to direct expression of the gene product in specific cells or organs the plant, when fused to the appropriate cell or organ specific promoter. Chimeric constructs can also be used to express one or more TFs to enhance or suppress nitrogen assimilation and/or usage or increase/reduce nitrogen storage.

The present disclosure provides plant cells in which have been introduced a polynucleotide encoding a N-responsive TF operably linked to a promoter—which may be constitutive or inducible or which is associated with a constitutive or inducible regulatory element—such that the N-response of the cell to N-exposure is modulated.

The present disclosure provides transgenic plants comprising an exogenous polynucleotide encoding a N-responsive TF operably linked to a promoter—which may be constitutive or inducible or which is associated with a constitutive or inducible regulatory element—such that the N-response of the transgenic plant to N-exposure is modified.

The present disclosure provides isolated nucleic acids comprising a full length cDNA sequence that is identical to a sequence encoding any N-responsive TF of a plant cell described herein, or is at least 85% identical to such sequence. For example, the cDNA sequence may be encoding a TF listed in Tables 1, 2, 3 or 4.

The present disclosure provides a recombinant or heterologous nucleic acid construct comprising in the 5 to 3' direction a promoter operable in a plant cell, and positioned downstream from the promoter and operably linked to the promoter is a nucleic acid molecule which encodes or is complementary to a molecule which encodes a transcription factor described herein. The disclosure also provide a vector comprising the recombinant nucleic acid construct.

In one embodiment, the disclosure provides a method for modulating (over-expressing or under-expressing) one or more TFs selected from Table 1. If more than TFs are used, they may be selected in any combination. The combinations of TFs to be tested would be prioritized using the method shown in Example 1. For example, two or more, three or more, four or more and so on or all of the TFs may be selected from Table 1. When more than one TF is to be modulated, each of the more than one TF, may be independently overexpressed or under-expressed.

TABLE 1

(40)
TFs that are NxTime
Responsive and have DAP-seq TF-target binding data

| GeneID | Name |
|---|---|
| AT4G27950 | CRF4 |
| AT5G62020 | HSFB2A |
| AT2G33550 | ASR3 |
| AT1G68550 | CRF10 |
| AT5G07680 | NAC4 |
| AT1G68670 | HHO2 |
| AT1G25550 | HHO3 |
| AT4G37180 | HHO5 |
| AT2G30590 | WRKY21 |
| AT5G65310 | ATHB5 |
| AT4G18880 | HSFA4A |
| AT1G45249 | ABF2 |
| AT1G12630 | ERF027 |
| AT5G15830 | bZIP3 |
| AT5G65210 | TGA1 |
| AT5G46590 | ANAC096 |
| AT4G24020 | NLP7 |
| AT3G62420 | BZIP53 |

TABLE 1-continued

(40)
TFs that are NxTime
Responsive and have DAP-seq TF-target binding data

| GeneID | Name |
|---|---|
| AT1G29860 | WRKY71 |
| AT2G22430 | ATHB6 |
| AT4G01550 | ANAC069 |
| AT1G19790 | SRS7 |
| AT5G10030 | TGA4 |
| AT1G52880 | ANAC018 |
| AT1G76880 | N/A |
| AT1G49560 | HHO6 |
| AT5G58900 | N/A |
| AT2G22540 | AGL22 |
| AT5G47390 | MYBH |
| AT5G39760 | AtHB23 |
| AT5G47660 | N/A |
| AT1G51700 | ADOF1 |
| AT5G66730 | ENY |
| AT3G13810 | AtIDD11 |
| AT5G29000 | PHL1 |
| AT1G32870 | ANAC013 |
| AT1G77920 | TGA7 |
| AT1G72010 | TCP22 |
| AT1G53910 | RAP2.12 |
| AT1G75080 | BZR1 |

In tables 1-4, "N/A" indicates that no name is assigned to that gene.

In one embodiment, the disclosure provides a method for modulating (over-expressing or under-expressing) one or more TFs selected from Table 2. If more than one TFs are used, they may be selected in any combination. Combinations of TF would be selected using the method taught in Example 1. For example, two or more, three or more, four or more and so on or all of the TFs may be selected from Table 2. The combinations of TFS would be selected from the list of FFLs which indicate which TF combinations work together to regulate a gene or a pathway of interest. This disclosure describes how to select TFs that work in combination to affect expression of N-uptake/assimilation pathway genes, but the approach can be used for any gene/pathway of interest. When more than one TF is to be modulated, each of the more than one TF, may be independently overexpressed or under-expressed.

TABLE 2

(19)
TFs that are NxTime Responsive and have DAP-seq
TF-target binding data with high N-Specificity Index

| GeneID | Name |
|---|---|
| AT4G27950 | CRF4 |
| AT1G25550 | HHO3 |
| AT1G68670 | HHO2 |
| AT4G37180 | HHO5 |
| AT5G62020 | HSFB2A |
| AT5G07680 | NAC4 |
| AT2G33550 | ASR3 |
| AT1G45249 | ABF2 |
| AT5G15830 | bZIP3 |
| AT5G65210 | TGA1 |
| AT5G46590 | ANAC096 |
| AT4G24020 | NLP7 |
| AT3G62420 | BZIP53 |
| AT5G10030 | TGA4 |
| AT1G49560 | HHO6 |
| AT5G66730 | IDD1 |

TABLE 2-continued

(19)
TFs that are NxTime Responsive and have DAP-seq
TF-target binding data with high N-Specificity Index

| GeneID | Name |
|---|---|
| AT5G58900 | N/A |
| AT5G29000 | PHL1 |
| AT5G47390 | MYBH |

In one embodiment, the disclosure provides a method for modulating (over-expressing or under-expressing) one or more TFs selected from Table 3. If more than one TFs are used, they may be selected in combinations. For example, two or more, three or more, four or more and so on or all of the TFs may be selected from Table 3. When more than one TF is to be modulated, each of the more than one TF, may be independently overexpressed or under-expressed.

TABLE 3

(23)
N-Regulated TFs that target the N-uptake/assimilation pathway genes

| GeneID | Name |
|---|---|
| AT4G27950 | CRF4 |
| AT5G07680 | NAC4 |
| AT5G15830 | bZIP3 |
| AT5G10970 | C2H2 |
| AT5G10030 | TGA4 |
| AT4G39780 | ERF060 |

TABLE 3-continued

(23)
N-Regulated TFs that target the N-uptake/assimilation pathway genes

| GeneID | Name |
|---|---|
| AT2G33550 | ASR3 |
| AT3G49940 | LBD38 |
| AT5G62430 | CDF1 |
| AT1G68670 | HHO2 |
| AT1G66140 | ZFP4 |
| AT5G49450 | bZIP1 |
| AT3G16870 | GATA17 |
| AT2G22200 | ERF056 |
| AT4G16141 | GATA17-L |
| AT5G62020 | HSFB2A |
| AT5G65210 | TGA1 |
| AT2G39250 | SNZ |
| AT2G22430 | HB6 |
| AT4G36540 | BEE2 |
| AT3G17609 | HYH |
| AT1G25550 | HHO3 |
| AT5G57660 | COL5 |

Table 4 includes a list of TFs that are N×Time Responsive. In one embodiment, the disclosure provides a method for modulating (over-expressing or under-expressing) one or more TFs selected from Table 4. If more than one TFs are used, they may be selected in any combination. For example, two or more, three or more, four or more and so on or all of the TFs may be selected from Table 4 based on their FFLs. When more than one TF is to be modulated, each of the more than one TF, may be independently overexpressed or under-expressed. A method for prioritizing which specific TFs to combine is taught in Example 1.

TABLE 4

N-responseive Transcription Factors

| N-responsive TFs in roots and shoots | Gene Symbol | TFs responsive to N-signal in shoots only | Gene Symbol | TFs responsive to N-signal in roots only | Gene Symbol |
|---|---|---|---|---|---|
| AT4G37180 | N/A | AT3G12270 | PRMT3 | AT2G33550 | N/A |
| AT1G68880 | bZIP | AT2G24500 | FZF | AT3G49940 | LBD38 |
| AT5G62430 | CDF1 | AT3G46640 | PCL1 | AT1G66600 | ABO3 |
| AT5G57660 | COL5 | AT3G57150 | NAP57 | AT5G28770 | BZO2H3 |
| AT5G07680 | NAC080 | AT3G23210 | bHLH34 | AT2G42280 | FBH4 |
| AT3G25890 | CRF11 | AT1G61730 | N/A | AT4G31800 | WRKY18 |
| AT5G15830 | bZIP3 | AT1G27050 | N/A | AT3G17609 | HYH |
| AT5G65210 | TGA1 | AT1G35560 | N/A | AT5G67420 | LBD37 |
| AT2G17150 | N/A | AT3G44750 | HDA3 | AT5G03680 | PTL |
| AT1G68670 | N/A | AT2G30590 | WRKY21 | AT5G56840 | N/A |
| AT5G10030 | TGA4 | AT1G43860 | N/A | AT3G11280 | N/A |
| AT3G62420 | BZIP53 | AT2G46310 | CRF5 | AT3G24310 | MYB305 |
| AT4G16141 | N/A | AT2G47890 | N/A | AT2G46270 | GBF3 |
| AT2G22200 | N/A | AT3G56570 | N/A | AT2G25900 | ATCTH |
| AT3G16870 | GATA17 | AT3G46590 | TRFL1 | AT5G22570 | WRKY38 |
| AT4G27950 | CRF4 | AT3G48100 | RR5 | AT1G67710 | ARR11 |
| AT5G37260 | RVE2 | AT5G56860 | GNC | AT5G61420 | MYB28 |
| AT3G61850 | DAG1 | AT1G19490 | N/A | AT3G44290 | NAC060 |
| AT1G07640 | OBP2 | AT2G22540 | SVP | AT4G37540 | LBD39 |
| AT4G00940 | N/A | AT1G67910 | N/A | AT1G69490 | NAP |
| AT1G20640 | N/A | AT4G30930 | NFD1 | AT2G18160 | bZIP2 |
| AT1G49560 | N/A | AT3G16940 | N/A | AT4G34000 | ABF3 |
| AT5G10970 | N/A | AT1G76350 | N/A | AT4G24060 | N/A |
| AT4G28610 | PHR1 | AT3G12560 | TRFL9 | AT3G07340 | N/A |
| AT4G36540 | BEE2 | AT1G63840 | N/A | AT3G51910 | HSFA7A |
| AT4G02640 | BZO2H1 | AT4G26150 | CGA1 | AT5G06510 | NF-YA10 |
| AT5G66730 | IDD1 | AT1G68550 | CRF10 | AT3G54990 | SMZ |
| AT2G40970 | MYBC1 | AT2G43500 | N/A | AT3G53200 | MYB27 |
| AT1G25550 | N/A | AT5G20885 | N/A | AT2G43000 | NAC042 |
| AT5G58900 | N/A | AT2G36930 | N/A | AT2G40750 | WRKY54 |
| AT5G29000 | PHL1 | AT2G39250 | SNZ | AT5G28650 | WRKY74 |
| AT1G14410 | WHY1 | AT1G70790 | N/A | AT5G60890 | MYB34 |
| AT1G13300 | HRS1 | AT4G36260 | STY2 | AT1G32510 | NAC011 |

TABLE 4-continued

N-responseive Transcription Factors

| N-responsive TFs in roots and shoots | Gene Symbol | TFs responsive to N-signal in shoots only | Gene Symbol | TFs responsive to N-signal in roots only | Gene Symbol |
|---|---|---|---|---|---|
| AT5G46590 | NAC096 | AT1G76880 | N/A | AT2G40260 | N/A |
| AT3G46130 | MYB48 | AT5G11060 | KNAT4 | AT3G12977 | N/A |
| AT5G56270 | WRKY2 | AT1G72010 | N/A | AT3G56970 | bHLH38 |
| AT1G75080 | BZR1 | AT2G04240 | XERICO | AT2G38470 | N/A |
| AT4G39780 | N/A | AT3G11580 | N/A | AT2G38470 | WRKY33 |
| AT4G25210 | N/A | AT5G25160 | ZFP3 | AT4G17460 | HAT1 |
| AT5G47390 | N/A | AT3G18010 | WOX1 | AT1G74080 | MYB122 |
| AT4G38340 | N/A | AT4G17230 | SCL13 | AT1G09540 | MYB61 |
| AT3G55980 | SZF1 | AT5G47660 | N/A | AT1G19350 | BES1 |
| AT4G14410 | bHLH104 | AT1G26960 | AtHB23 | AT2G47070 | SPL1 |
| AT1G45249 | ABF2 | AT3G16857 | RR1 | AT5G03150 | JKD |
| AT5G53290 | CRF3 | AT5G17600 | N/A | AT1G02230 | NAC004 |
| AT4G24020 | NLP7 | AT1G72220 | N/A | AT1G22070 | TGA3 |
| AT4G35270 | N/A | AT5G05410 | DREB2A | AT2G47260 | WRKY23 |
| AT2G17040 | NAC036 | AT1G07520 | N/A | AT4G12750 | N/A |
| AT1G66140 | ZFP4 | AT1G79430 | APL | AT5G40880 | N/A |
| AT5G62020 | HSFB2A | AT2G22430 | HB6 | AT1G76580 | N/A |
| AT2G40140 | CZF1 | AT3G23690 | N/A | AT2G28550 | RAP2.7 |
| AT5G41020 | N/A | AT3G15510 | NAC2 | AT5G59450 | N/A |
| AT1G72050 | TFIIIA | AT3G13810 | IDD11 | AT5G49300 | GATA16 |
| AT1G19700 | BEL10 | AT3G02340 | N/A | AT3G59580 | N/A |
| | | AT3G28910 | MYB30 | AT3G10500 | NAC053 |
| | | AT4G18880 | HSF A4A | AT4G37790 | HAT22 |
| | | AT1G14510 | AL7 | AT2G22850 | bZIP6 |
| | | AT4G28270 | RMA2 | AT3G61830 | ARF18 |
| | | AT3G06740 | GATA15 | AT3G11260 | WOX5 |
| | | AT5G46760 | MYC3 | AT1G67310 | N/A |
| | | AT1G32870 | NAC13 | AT1G18570 | MYB51 |
| | | AT5G02470 | DPA | AT2G43140 | N/A |
| | | AT5G48250 | BBX8 | AT5G51780 | N/A |
| | | AT1G66390 | MYB90 | AT4G36060 | bHLH11 |
| | | AT2G35940 | BLH1 | AT5G65790 | MYB68 |
| | | AT3G02790 | N/A | AT2G25000 | WRKY60 |
| | | AT3G61630 | CRF6 | AT1G51140 | FBH3 |
| | | AT4G27410 | RD26 | AT1G31320 | LBD4 |
| | | AT5G65310 | HB5 | AT5G06800 | N/A |
| | | AT2G36340 | N/A | AT3G47640 | PYE |
| | | AT2G48100 | N/A | AT3G49760 | bZIP5 |
| | | AT1G68130 | IDD14 | AT3G02830 | ZFN1 |
| | | AT3G02290 | N/A | AT3 G01220 | HB20 |
| | | AT2G27100 | SE | AT4G00238 | N/A |
| | | AT3G46090 | ZAT7 | AT1G13260 | RAV1 |
| | | AT5G52010 | N/A | AT1G72360 | ERF73 |
| | | AT1G71030 | MYBL2 | AT5G61590 | N/A |
| | | AT1G75540 | BBX21 | AT5G04410 | NAC2 |
| | | AT3G62240 | N/A | AT3G10800 | BZIP28 |
| | | AT5G25220 | KNAT3 | AT2G18060 | VND1 |
| | | AT1G19790 | SRS7 | AT5G18270 | ANAC087 |
| | | AT2G32600 | N/A | AT2G41835 | N/A |
| | | AT2G28200 | N/A | AT1G13600 | bZIP58 |
| | | AT1G52880 | NAM | AT1G74660 | MIF1 |
| | | AT5G41410 | BEL1 | AT1G34180 | NAC016 |
| | | AT3G54320 | WRI1 | AT1G80730 | ZFP1 |
| | | AT5G15820 | N/A | AT2G38300 | N/A |
| | | AT1G75410 | BLH3 | AT4G35040 | bZIP19 |
| | | AT2G24790 | COL3 | AT2G23760 | BLH4 |
| | | AT4G23750 | CRF2 | AT5G52830 | WRKY27 |
| | | AT3G47600 | MYB94 | AT2G30250 | WRKY25 |
| | | AT5G08750 | N/A | AT1G61660 | N/A |
| | | AT5G05090 | N/A | AT1G62990 | KNAT7 |
| | | AT5G14540 | N/A | AT3 G21430 | ALY3 |
| | | AT5G19430 | N/A | AT5G47230 | ERF5 |
| | | AT1G12630 | N/A | AT4G25560 | LAF1 |
| | | AT1G20910 | N/A | AT1G04990 | N/A |
| | | AT1G29860 | N/A | AT5G06110 | N/A |
| | | AT1G51700 | WRKY71 | AT3G18990 | VRN1 |
| | | AT5G47640 | DOF1 | AT2G28810 | N/A |
| | | AT1G73730 | NF-YB2 | AT2G27050 | EIL1 |
| | | AT4G25610 | EIL3 | AT4G13480 | MYB79 |
| | | AT1G12980 | N/A | AT2G16400 | BLH7 |
| | | AT2G45050 | ESR1 | AT3G25790 | N/A |
| | | AT4G33565 | GATA2 | AT5G13180 | NAC083 |
| | | AT1G53910 | N/A | AT1G74650 | MYB31 |
| | | AT1G77920 | RAP2.12 | AT4G13620 | N/A |
| | | | TGA7 | | |

TABLE 4-continued

N-responseive Transcription Factors

| N-responsive TFs in roots and shoots | Gene Symbol | TFs responsive to N-signal in shoots only | Gene Symbol | TFs responsive to N-signal in roots only | Gene Symbol |
|---|---|---|---|---|---|
| | | AT2G18300 | HBI1 | AT1G03040 | N/A |
| | | AT3G13040 | N/A | AT5G24800 | BZIP9 |
| | | AT2G30470 | HSI2 | AT2G01570 | RGA1 |
| | | AT5G39760 | HB23 | AT3G22170 | FHY3 |
| | | AT4G04885 | PCFS4 | AT3G48920 | MYB45 |
| | | AT4G11140 | CRF1 | AT5G56960 | N/A |
| | | AT5G38895 | N/A | AT3G14020 | NF-YA6 |
| | | AT1G02030 | N/A | AT5G38800 | bZIP43 |
| | | AT2G02740 | WHY3 | AT1G18330 | EPR1 |
| | | AT3G16720 | ATL2 | AT5G15150 | HB-3 |
| | | AT4G31920 | RR10 | AT3G46600 | N/A |
| | | | | AT1G57560 | MYB50 |
| | | | | AT1G69310 | WRKY57 |
| | | | | AT5G12850 | N/A |
| | | | | AT2G26150 | HSFA2 |
| | | | | AT5G62610 | N/A |
| | | | | AT1G72830 | NF-YA3 |
| | | | | AT4G18390 | TCP2 |
| | | | | AT3G50700 | IDD2 |
| | | | | AT3G48430 | REF6 |
| | | | | AT1G10480 | ZFP5 |
| | | | | AT1G01010 | NAC001 |
| | | | | AT2G31370 | N/A |
| | | | | AT1G69580 | N/A |
| | | | | AT5G20730 | NPH4 |
| | | | | AT1G49950 | TRB1 |
| | | | | AT1G69780 | ATHB13 |
| | | | | AT1G03970 | GBF4 |
| | | | | AT1G01720 | ATAF1 |
| | | | | AT4G32040 | KNAT5 |
| | | | | AT4G23980 | ARF9 |
| | | | | AT1G27740 | RSL4 |
| | | | | AT1G16530 | ASL9 |
| | | | | AT3G25990 | N/A |
| | | | | AT4G17785 | MYB39 |
| | | | | AT3G04670 | WRKY39 |
| | | | | AT2G25180 | RR12 |
| | | | | AT5G49620 | MYB78 |
| | | | | AT3G09735 | N/A |
| | | | | AT4G12350 | MYB42 |
| | | | | AT2G44940 | N/A |
| | | | | AT5G42700 | N/A |
| | | | | AT5G57150 | N/A |
| | | | | AT5G48670 | AGL80 |
| | | | | AT2G40950 | BZIP17 |
| | | | | AT5G66870 | ASL1 |
| | | | | AT1G25560 | TEM1 |
| | | | | AT4G25440 | ZFWD1 |

In one embodiment, the disclosure provides a method for modulating (over-expressing or under-expressing) one or more TFs. In Example 1, we describe a method for prioritizing which TFs to test using a working example wherein the one or more TFs are CRF4, in combination with its validated downstream TFs CDF1, SNZ, ERF060. Another embodiment includes altering expression of CRF4, bZIP1, and HHO3 in any combination. The one or more TFs may be selected in combinations of FFLs. For example, two, three, four, five or all of the TFs may be selected from CRF4, CDF1, SNZ, ERF060, bZIP1, and HHO3. When more than one TF is to be modulated, each of the more than one TF, may be independently overexpressed or under-expressed. The target TF combinations for which the TFs target genes in the N-assimilation pathway can be prioritized—as shown in Table 3.

In one aspect, the present disclosure provides a method for identifying temporal relationships of TFs that cooperatively operate in response to changes in N-availability. The general method is described in Example 1. The method is applicable to identification of TFs in response to any external stimulus in any type of biological material. The method comprises exposing a biological material to the external stimulus and generating mRNA transcription profiles (transcriptome profiles) at predetermined times following exposure. The transcriptome profiles are compared to control profiles, which have not been exposed to the external stimulus. This allows identification of genes expressed at each time. Time-bin gene sets (referred to as just-in-time" bins) are generated with each time-bin set representing first genes expressed at that time. Then "just-in-time" bins represent exclusive sets of genes first substantially regulated by the external stimulus at that time. For each "just-in-time" bin gene set, all promoters for all genes in the gene set are evaluated to identify cis-binding motifs that are over-represented. Separately, the "just-in-time" bin gene sets are also queried for overrepresented GO terms to determine the biological processed controlled at each "just-in-time" point.

Then, specific TF-target relationships and networks are identified using a machine learning approach.

In one embodiment, the biological material is a plant material and the external stimulus is Nitrogen. For example, using an external stimulus of exposure to a composition comprising $KNO_3$ and $NH_4NO_3$ can be used to expose biological material such as seedlings. Analysis can be carried out at any predetermined intervals after exposure, such as 0, 5, 10, 15, 20, 30, 45, 60, 90, and 120 or longer or any time between 0 and 120 minutes or longer than 120 minutes. The predetermined intervals can be of any duration.

The TFs identified by this method can be validated, for example, by using perturbation studies as described herein. A method of evaluating individual TFs, known as Transient Assay Reporting Genome-wide Effects of Transcription factors (TARGET) can be used. This method is described in U.S. patent application Ser. No. 14/457,402, and PCT application no. PCT/US2016/016811, the entire disclosures of which are incorporated herein by reference. A further improvement of the TARGET method is provided in Example 3 herein, which allows a more rapid validation testing of identified TFs.

In this disclosure, we were able to derive novel insights into the temporal dynamics of N-regulatory networks by devising and combining several time-based approaches. First, we were able to uncover a temporal cis-regulatory cascade underlying dynamic N-signaling using a "just-in-time" classification algorithm that captures the first time-point at which genes respond to N-signaling. Second, we used DFG, a time-driven machine-learning approach (Mirowski et al., Machine Learning and Knowledge Discovery in Databases: European Conference, ECML PKDD 2009, Bled, Slovenia, September 7-11, 2009, Proceedings, Part II, W. Buntine, et al., Editors. 2009, Springer Berlin Heidelberg: Berlin, Heidelberg. p. 128-143.), to infer the interactions of 172 TFs and 2172 genes in the N-signaling cascade. Third, we "pruned" the time-inferred Gene Regulatory Network (GRN) using a network precision cutoff derived from genome-wide targets of three novel regulators of N-uptake/metabolism (CRF4, SNZ, CDF1) validated herein. Fourth, for 35 TFs, the high-confidence inferred edges in the GRN were also supported by independent TF-target binding data (DAP-Seq) (O'Malley et al., Cell, 2016. 166(6): p. 1598), which we also used to calculate an "N-specificity" index for each such TF in the GRN.

This time-based GRN now reveals the temporal relationships of individual TFs previously validated in the N-response (e.g. NLP7/8, TGA1/4, NAC4, HRS1, LBD37,38, 39). It also connects these known TFs with new TFs in the N-response cascade (CRF4, SNZ, CDF1) validated herein. Specifically, our TF perturbation studies of CRF4 (5 min), SNZ (10 min), CDF1 (45 min), confirm their role in regulating a significant number of genes in the N-response network, including ones regulating nitrate uptake/assimilation in cells and regulating nitrate uptake/biomass in plants. Beyond these proof-of-principle examples, the high-confidence GRN of N-signaling now provides the temporal "transcriptional logic" for >150 candidate TFs for perturbations aimed at improving Nitrogen Use Efficiency (NUE) with potential applications in agriculture.

In one embodiment, this disclosure provides a method for modulating Nitrogen (N) uptake/assimilation and/or usage in plant cell or a plant comprising over-expressing or under-expressing CRF4. When a plant is exposed to low nitrogen environment, and the CRF4 is over-expressed, it is considered that N uptake and/or assimilation is reduced, thereby conserving nitrogen resources. Optionally, the expression of SNZ and/or CDF1 may be inhibited or under-expressed in the plant, whereby the N uptake and/or assimilation can be further reduced. Conversely, if increased N uptake and assimilation under low-N are desired, CRF4 can be inhibited or underexpressed and/or SNZ and/or CDF1 can be over-expressed.

The term "low nitrogen environment" as used in this disclosure means nutrient environment (such as soil or hydroponics) having 1 mM or less nitrogen (N), supplied as nitrate and/or ammonia.

As another example, four transcription factors—HHO5, HHO6, PHL1 and TGA1 have been identified as being positive regulators of N assimilation/uptake. Therefore, in one embodiment, one or more of HHO5, HHO6, PHL1 and TGA1 may be over-expressed to increase N uptake/assimilation (such as when increased metabolism or growth of a plant is desired). Conversely, the expression of one or more of HHO5, HHO6, PHL1 and TGA1 may be repressed when N uptake/assimilation (such as when reduced metabolism or growth is desired). Combinations of TFs can be determined using their validated target genes in the N-uptake/assimilation which are shown in FIG. 27.

The present disclosure identifies the effects of TFs on the genes involved in various N-uptake/assimilation steps (FIG. 27). For each TF, including the ones identified in this disclosure, FIG. 27 indicates if the target gene is induced or repressed by the expression of the TF. Dark grey boxes indicate that the TF induces the expression of the target gene, while light grey boxes with hatching indicates that the TF represses the target gene. White boxes indicate that no effect was seen. For example, HHO2, HB6, SNZ, GATA17L, bZIP3, and CDF1 induce the expression of AMT1.3 (gene AT3G24300). ZPF4, HHO2, GATA17, HYH, BEE2, C2H2, COLS, and HSFB2A repress the expression of AMT1.1 (gene AT4G13510) and so on. Therefore, if a particular gene in the N-uptake/assimilation pathway, or a group of genes is to be induced or repressed, the relevant one or more TFs may be over or underexpressed. For example, if the goal is to increase the expression of GLN1.2 (AT1G66200), ERF056 may be repressed and CDF1 may be overexpressed, or the combined repression of ERF056 and over-expression of CDF1 can be carried out. Other combinations for repressing and/or over-expressing the TFs may be easily identified from this disclosure including FIG. 27. In one example, if the goal is to increase nitrate uptake under low-N, the expression of NTR2.1—the high affinity nitrate transporter—can be modulated by down regulation of CRF4, and/or upregulation of its downstream TFs SNZ and CDF1 (as shown in Table 27, and FIG. 6). In another example, the storage of Nitrogen in a plant may be improved by increasing the expression of ASN genes. The present disclosure identifies that the combined over-expression of PHL1 and repression of TGA1 would result in an increased expression of ASN2 and ASN3 genes (as shown in FIG. 27).

In one embodiment, the disclosure provides a method to increase or decrease the expression of a gene in the N-uptake/assimilation pathway comprising over expressing a TF that induces the expression of the particular gene in the N-uptake/assimilation pathway, and/or repressing a TF that represses the expression of that particular gene. In one embodiment, the method comprises overexpressing multiple TFs that induce the expression of the desired gene, and/or repressing multiple TFs that repress the expression of that gene. Suitable combinations of TFs for overexpression or repression may be identified for modulating multiple target genes in the N-assimilation pathway, such as, for example, from FIG. 27. In one example, if the goal is to increase nitrate uptake under low-N, the expression of NTR2.1—the high affinity nitrate transporter—can be induced by down regulation of CRF4, and/or upregulation of its downstream TFs SNZ and CDF1 (as shown in Table 27, and FIG. 6).

TFs induced early in response to N-supply and at the top of the cascade as described herein are more likely to influence Nitrogen uptake since the Nitrogen uptake genes are regulated early as well. Therefore these TFs would be prioritized targets for transgenic plants (See FIG. 3B). For example, CRF4 is induced earliest and is at the top of the TF cascade (5 min). TFs in the cascade include HHO5 (10 min), etc, as shown in FIG. 3B).

In one embodiment, the expression of one or more TFs in a plant cell is modulated by introducing TFs into the nucleus in the TARGET system. The nucleotide sequences encoding a TF introduced into a plant cell may be endogenous or exogenous in origin. By "modulate" or "modulating" "expression of a target gene" is intended that the expression of the target gene is increased or decreased as a result of TF nuclear localization relative to the expression level in a plant that has not been altered by the methods described herein.

By "increased" or "over expression" it is intended that expression of the target nucleotide sequence is increased over expression observed in conventional transgenic lines for heterologous genes and over endogenous levels of expression for homologous genes. Heterologous or exogenous genes comprise genes that do not occur in the plant of interest in its native state. Homologous or endogenous genes are those that are natively present in the plant genome. Generally, expression of the target sequence is significantly increased (p-val 0.05), compared to uninduced controls. In some embodiments, the expression may be increased at least about 10% to 25%, 25% to 50%, 50% to 100% or 100% to 200%.

By "decreased expression" or "under-expression" it is intended that expression of the target nucleotide sequence is decreased below expression observed in conventional transgenic lines for heterologous genes and below endogenous levels of expression for homologous genes. Generally, expression of the target nucleotide sequence of interest is significantly decreased (p-vat 0.05) compared to controls. In some embodiments, the expression may be decreased at least about 10% to 25%, 25% to 50%, 50% to 100% or 100% to 200%.

Expression levels may be assessed by determining the level of a gene product by any method known in the art including, but not limited to determining the levels of the RNA and protein encoded by a particular target gene. For genes that encode proteins, expression levels may be determined, for example, by quantifying the amount of the protein present in plant cells, or in a plant or any portion thereof. Alternatively, if a desired target gene encodes a protein that has a known measurable activity, then activity levels may be measured to assess expression levels.

In various embodiments, expression of one or a combination of transcription factors described herein is modified by, for example, adjusting copy number of the gene(s) encoding the transcription factor(s), or by replacing an endogenous promoter(s), or by disrupting the gene(s) encoding the transcription factor(s), or by interfering with transcription and/or translation of the transcription factors. For increased expression the copy number of the gene encoding the transcription factor can be increased using any suitable genetic engineering approach, non-limiting examples of which are described herein. Increased copy number can be provided by editing the plant genome, or episomally. Alternatively, to increase expression, an endogenous promoter can be replaced with a stronger promoter, which may also be an inducible promoter as further described below, or expression can be driven from any suitable promoter using recombinant, episomal approaches. Thus, in various embodiments, nucleic acid vectors are used to modify cells such that expression of one or more of the transcription factors described herein is modified. The nucleic acid vectors may be integrated into the genome. The nucleic acid vectors can encode one or more polynucleotides that can facilitate downregulation of expression of a transcription factor, including but not necessarily limited to via antisense, and/or RNAi-mediated approaches, and/or via genome editing, such as by use of CRISPR-based genome editing systems. For example, a CRISPR-based editing approach can be used and can be adapted from known techniques, such as those described in Bortesi and Fischer "The CRISPR/Cas9 system for plant genome editing and beyond" Biotechnology Advances, Volume 33, Issue 1, January-February 2015, Pages 41-52, and the approaches described in Ma et al., "CRISPR/Cas9 Platforms for Genome Editing in Plants: Developments and Applications" Molecular Plant, Vol. 9, Issue 7, p961-9'74, 6 Jul. 2016, the disclosures of each of which are incorporated herein by reference. Zinc finger nucleases (ZFNs) or transcription activator-like effector nucleases (TALENs) can be used to modify expression of one or more of the transcription factors described herein. RNAi can be used to affect expression of one or more transcription factors described herein. Suitable RNAi approaches are known and can be adapted for use in the present disclosure, such as the description in Younis et al., "RNA Interference (RNAi) Induced Gene Silencing: A Promising Approach of Hi-Tech Plant Breeding" International Journal of Biological Sciences, International Journal of Biological Sciences, 10(10), 1150-1158. http://doi.org/10.7150/ijbs.10452, the disclosure of which is incorporated herein by reference.

Transformation/Transfection:

Any method or delivery system may be used for the delivery and/or transfection of nucleic acid vectors encoding any of the transcription factors or other genetic elements and/or systems as described herein. The vectors may be delivered to the plant cell either alone, or in combination with other agents.

Transfection may be accomplished by a wide variety of means, as is known to those of ordinary skill in the art. Such methods include, but are not limited to, *Agrobacterium*-mediated transformation (e.g., Komari et al., 1998, Curr. Opin. Plant Biol., 1:161), particle bombardment mediated transformation (e.g., Finer et al., 1999, Curr. Top. Microbiol. Immunol., 240:59), protoplast electroporation (e.g., Bates, 1999, Methods Mol. Biol., 111:359), viral infection (e.g., Porta and Lomonossoff, 1996, Mol. Biotechnol. 5:209), microinjection, and liposome injection. Other exemplary delivery systems that can be used to facilitate uptake by a cell of the nucleic acid include calcium phosphate and other chemical mediators of intracellular transport, microinjection compositions, and homologous recombination compositions (e.g., for integrating a gene into a preselected location within the chromosome of the cell). Alternative methods may involve, for example, the use of liposomes, electroporation, or chemicals that increase free (or "naked") DNA uptake, transformation using viruses or pollen and the use of microprojection. Standard molecular biology techniques are common in the art (e.g., J. Sambrook and E. F. Fritsch & T. Maniatis (Ed.), "Molecular Cloning, a Laboratory Manual (3rd edition), Cold Spring Harbor Press and Cold Spring Harbor, N.Y. (2001)). For example, in one embodiment of the present invention, *Arabidopsis* or another plant species is transformed with a gene encoding a TF using *Agrobacterium*. The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference).

Plant cells and plants can comprise two or more nucleotide sequence constructs. Any means for producing a plant or plant cell comprising the nucleotide sequence constructs described herein are encompassed by the present invention. For example, a nucleotide sequence encoding the modulator can be used to transform a plant at the same time as the nucleotide sequence encoding the precursor RNA. The nucleotide sequence encoding the precursor mRNA can be introduced into a plant that has already been transformed with the modulator nucleotide sequence. Alternatively, transformed plants, one expressing the modulator and one expressing the RNA precursor, can be crossed to bring the genes together in the same plant. Likewise, viral vectors may be used to express gene products by various methods generally known in the art. Suitable plant viral vectors for expressing genes should be self-replicating, capable of systemic infection in a host, and stable. Additionally, the viruses should be capable of containing the nucleic acid sequences that are foreign to the native virus forming the vector. Transient expression systems may also be used.

*Agrobacterium* transformation can be used for transformation of dicotyledonous as well as monocots—see U.S. Pat. No. 8,153,863, incorporated herein by reference, Tomes et al., 1995, "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); WO 92/14828; Hiei et al., 1994, The Plant Journal 6:271-282). See also, Shimamoto, K., 1994, Current Opinion in Biotechnology 5:158-162; Vasil et al., 1992, Bio/Technology 10:667-674; Vain et al., 1995, Biotechnology Advances 13(4):653-671; Vasil et al., 1996, Nature Biotechnology 14:702).

*Agrobacterium*:

A TF-encoding nucleic acid sequences or a nucleic acid designed to disrupt expression of TF utilized in the present invention can be introduced into plant cells using Ti plasmids of *Agrobacterium tumefaciens* (*A. tumefaciens*), root-inducing (Ri) plasmids of *Agrobacterium rhizogenes* (*A. rhizogenes*), and plant virus vectors. For reviews of such techniques see, for example, Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9, and Horsch et al., 1985, Science, 227:1229.

In using an *A. tumefaciens* culture as a transformation vehicle, it is most advantageous to use a non-oncogenic strain of *Agrobacterium* as the vector carrier so that normal non-oncogenic differentiation of the transformed tissues is possible. The *Agrobacterium* may harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid may contain at least one border region of the T-DNA region of a wild-type Ti plasmid flanking the nucleic acid to be transferred. Binary Ti plasmid systems have been shown effective in the transformation of plant cells (De Framond, Biotechnology, 1983, 1:262; Hoekema et al., 1983, Nature, 303:179). Such a binary system does not require integration into the Ti plasmid of *A. tumefaciens*. In some embodiments, a disarmed Ti-plasmid vector carried by *Agrobacterium* can exploit its natural gene transferability (EP-A-270355, EP-A-01 16718, Townsend et al., 1984, NAR, 12:8711, U.S. Pat. No. 5,563,055).

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*. In addition, gene transfer can be accomplished by in planta transformation by *Agrobacterium*, as described by Bechtold et al., (C.R. Acad. Sci. Paris, 1993, 316:1194). This approach is based on the vacuum infiltration of a suspension of *Agrobacterium* cells.

In certain embodiments, a TF-encoding nucleic acid or mutant thereof is introduced into plant cells by infecting such plant cells, an explant, a meristem or a seed, with transformed *A. tumefaciens* as described above. Under appropriate conditions known in the art, the transformed plant cells are grown to form shoots, roots, and develop further into plants.

Other methods such as microprojectile bombardment, electroporation and direct DNA uptake can also be used. Alternatively, a combination of different techniques may be employed to enhance the efficiency of the transformation process, e.g., bombardment with *Agrobacterium*-coated microparticles (See EP-A-486234) or microprojectile bombardment to induce wounding followed by co-cultivation with *Agrobacterium* (See EP-A-486233).

CaMV:

In some embodiments, cauliflower mosaic virus (CaMV) can be used as a vector for introducing a desired nucleic acid into plant cells (U.S. Pat. No. 4,407,956). CaMV viral DNA genome can be inserted into a parent bacterial plasmid creating a recombinant DNA molecule which can be propagated in bacteria. After cloning, the recombinant plasmid again can be cloned and further modified by introduction of the desired nucleic acid sequence. The modified viral portion of the recombinant plasmid can then be excised from the parent bacterial plasmid, and used to inoculate the plant cells or plants.

Mechanical and Chemical Means:

In some embodiments, a TF-encoding nucleic acid or a nucleic acid designed to disrupt expression of TF can be introduced into a plant cell using mechanical or chemical means. For example, in one embodiment, the TF-encoding nucleic acid or the nucleic acid designed to disrupt expression of TF can be mechanically transferred into the plant cell by microinjection using a micropipette. See, e.g., WO 92/09696, WO 94/00583, EP 331083, EP 175966, Green et al., 1987, Plant Tissue and Cell Culture, Academic Press, Crossway et al., 1986, Biotechniques 4:320-334.

PEG:

In one embodiment, the nucleic acid can be transferred into the plant cell by using polyethylene glycol (PEG) which forms a precipitation complex with genetic material that is taken up by the cell.

Electroporation:

Electroporation can be used to introduce a nucleic acid into the cell, e.g., precursor miRNA, or a nucleotide sequence able to be transcribed to produce TF protein (see, e.g., Fromm et al., 1985, PNAS, 82:5824). Typically, electroporation includes the application of one or more electrical voltage "pulses" having relatively short durations (usually less than 1 second, and often on the scale of milliseconds or microseconds) to a media containing the cells. The electrical pulses typically facilitate the non-lethal transport of extracellular nucleic acids into the cells. Electroporation techniques are described in, e.g., EP 290395, WO 8706614, Riggs et al., 1986, Proc. Natl. Acad. Sci. USA 83:5602-5606; D'Halluin et al., 1992, Plant Cell 4:1495-1505). Other forms of direct DNA uptake can also be used in the methods provided herein, such as those discussed in, e.g., DE 4005152, WO 9012096, U.S. Pat. No. 4,684,611, Paszkowski et al., 1984, EMBO J. 3:2717-2722.

Ballistic and Particle Bombardment:

Another method for introducing a TF-encoding nucleic acid or a nucleic acid designed to disrupt expression of TF into a plant cell is high velocity ballistic penetration by small particles with the nucleic acid to be introduced contained either within the matrix of such particles, or on the surface thereof (Klein et al., 1987, Nature 327:70). Genetic material can be introduced into a cell using particle gun ("gene gun") technology, also called microprojectile or microparticle bombardment. In this method, small, high-density particles (microprojectiles) are accelerated to high velocity in conjunction with a larger, powder-fired macroprojectile in a particle gun apparatus. The microprojectiles have sufficient momentum to penetrate cell walls and membranes, and can carry RNA or other nucleic acids into the interiors of bombarded cells. Bombardment transformation methods are also described in Sanford et al. (Techniques 3:3-16, 1991) and Klein et al. (Bio/Techniques 10:286, 1992). Although, typically only a single introduction of a new nucleic acid sequence(s) is required, this method particularly provides for multiple introductions.

Lipid Formulations and Colloidal Dispersions:

Lipid formulations may be used for the transfection and/or intracellular delivery of nucleic acids are commercially available, for instance, from QIAGEN, for example as EFFECTENE (a non-liposomal lipid with a special DNA condensing enhancer) and SUPER-FECT (a novel acting dendrimeric technology). LIPOFECTIN and LIPOFECTAMINE from Thermo Fisher Scientific may be used, which are formed of cationic lipids such as N-[1-(2,3-dioleyloxy)-propyl]-N,N,N-trimethylammonium chloride ("DOTMA") and dimethyl dioctadecylammonium bromide ("DDAB"). Liposomes also are well known in the art and have been widely described in the literature, for example, in Gregoriadis, G., 1985, Trends in Biotechnology 3:235-241; Freeman et al., 1984, Plant Cell Physiol. 29:1353). Nucleic Acid Constructs:

The nucleic acid constructs comprising TF sequences, and any other polynucleotides of the invention, may be provided in nucleotide sequence constructs or expression cassettes for expression in the plant of interest. The cassette will include 5' and 3' regulatory sequences operably linked to an encoding nucleotide sequence of the invention. The expression cassette may additionally comprise an additional gene to be co-transformed into the organism. Alternatively, the additional gene(s) can be provided on multiple expression cassettes. In certain embodiments, an expression cassette can be used with a plurality of restriction sites for insertion of the sequences of the invention to be under the transcriptional regulation of the regulatory regions. The expression cassette can additionally contain selectable marker genes (see below).

The expression cassette generally includes in the 5'-3' direction of transcription, a transcriptional and translational initiation region, a DNA sequence of the invention, e.g., TF or a sequence designed to disrupt expression of TF, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al., 1991, Mol. Gen. Genet. 262:141-144; Proudfoot, 1991, Cell 64:671-674; Sanfacon et al., 1991, Genes Dev. 5:141-149; Mogen et al., 1990, Plant Cell 2:1261-1272; Munroe et al., 1990, Gene 91:151-158; Ballas et al., 1989, Nucleic Acids Res. 17:7891-7903; and Joshi et al., 1987, Nucleic Acid Res. 15:9627-9639.

In some embodiments, a nucleic acid (e.g., encoding a TF) can be delivered to the cell in a vector. As used herein, a "vector" is any vehicle capable of facilitating the transfer of the nucleic acid to the cell such that the nucleic acid can be processed and/or expressed in the cell. The vector may transport the nucleic acid to the cells with reduced degradation, relative to the extent of degradation that would result in the absence of the vector. The vector optionally includes gene expression sequences or other components (such as promoters and other regulatory elements) able to enhance expression of the nucleic acid within the cell. The invention also encompasses the cells transfected with these vectors, including those cells previously described. In certain embodiments, the cells are transfected or transformed with a vector that specifically (or preferably) overexpresses a TF in the vegetative tissues of the plant, but not in the majority of other cell types of the plant. Vectors employed for transformation of a plant cell include an encoding nucleic acid sequence operably associated with a promoter, such as a leaf-specific promoter.

Vectors useful in the invention include, but are not limited to, plasmids, phagemids, viruses, other vehicles derived from viral or bacterial sources that have been manipulated by the insertion or incorporation of the nucleotide sequences (or precursor nucleotide sequences) of the invention. Viral vectors useful in certain embodiments include, but are not limited to, nucleic acid sequences from the following viruses: retroviruses; adenovirus, or other adeno-associated viruses; mosaic viruses such as tobamoviruses; potyviruses, nepoviruses, and RNA viruses such as retroviruses. One can readily employ other vectors not named but known to the art. Some viral vectors can be based on non-cytopathic eukaryotic viruses in which non-essential genes have been replaced with the nucleotide sequence of interest. Non-cytopathic viruses include retroviruses, the life cycle of which involves reverse transcription of genomic viral RNA into DNA with subsequent proviral integration into host cellular DNA. Genetically altered retroviral expression vectors can have general utility for the high-efficiency transduction of nucleic acids. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the cells with viral particles) are well known to those of ordinary skill in the art. Examples of standard protocols can be found in Kriegler, M., 1990, Gene Transfer and Expression, A Laboratory Manual, W.H. Freeman Co., New York, or Murry, E. J. Ed., 1991, Methods in Molecular Biology, Vol. 7, Humana Press, Inc., Cliffton, N.J. Another-example of a virus for certain applications is the adeno-associated virus, which is a double-stranded DNA virus. The adeno-associated virus can be engineered to be replication-deficient and is capable of infecting a wide range of-cell types and species. The adeno-associated virus further has advantages, such as heat and lipid solvent stability; high transduction frequencies in cells of diverse lineages; and/or lack of superinfection inhibition, which may allow multiple series of transductions.

Another vector suitable for use with the method provided herein is a plasmid vector. Plasmid vectors, have been extensively described in the art and are well-known to those of skill in the art. See, e.g., Sambrook et al., 1989, Molecular Cloning: A Laboratory Manual, Second Edition, Cold Spring Harbor Laboratory Press. These plasmids may have a promoter compatible with the host cell, and the plasmids can express a peptide from a gene operatively encoded within the plasmid. Some commonly used plasmids include pBR322, pUC18, pUC19, pRC/CMV, SV40, and pBlue-Script. Other plasmids are well-known to those of ordinary skill in the art. Additionally, plasmids may be custom-designed, for example, using restriction enzymes and ligation reactions, to remove and add specific fragments of DNA or other nucleic acids, as necessary. The present invention also includes vectors for producing nucleic acids or precursor nucleic acids containing a desired nucleotide sequence (which can, for instance, then be cleaved or otherwise processed within the cell to produce a precursor miRNA). These vectors may include a sequence encoding a nucleic acid and an in vivo expression element, as further described below. In some cases, the in vivo expression element includes at least one promoter.

Where appropriate, the gene(s) for enhanced expression may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5,380,831, and 5,436,391, and Murray et al., 1989, Nucleic Acids Res. 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When desired, the sequence is modified to avoid predicted hairpin secondary mRNA structures. However, it is recognized that in the case of nucleotide sequences encoding the miRNA precursors, one or more hairpin and other secondary structures may be desired for proper processing of the precursor into an mature miRNA and/or for the functional activity of the miRNA in gene silencing.

The expression cassettes can additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al., 1989, PNAS USA 86:6126-6130); potyvirus leaders, for example, TEV leader (Tobacco Etch Virus) (Allison et al., 1986); MDMV leader (Maize Dwarf Mosaic Virus); Virology 154:9-20), and human immunoglobulin heavy-chain binding protein (BiP), (Macejak et al., 1991, Nature 353:90-94); untranslated leader from the coat protein miRNA of alfalfa mosaic virus (AMV RNA 4) (Jobling et al., 1987, Nature 325:622-625); tobacco mosaic virus leader (TMV) (Gallie et al., 1989, Molecular Biology of RNA, ed. Cech (Liss, New York), pp. 237-256); and maize chlorotic mottle virus leader (MCMV) (Lommel et al., 1991, Virology 81:382-385). See also, Della-Cioppa et al., 1987, Plant Physiol. 84:965-968.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Promoters and Other Regulatory Sequences:

The nucleic acid sequence encoding a TF or a nucleic acid designed to disrupt expression of same can be operably linked with a promoter, such as a leaf-preferred or leaf-specific promoter. It may be desirable to introduce more than one copy of a polynucleotide into a plant for enhanced expression. For example, multiple copies of a TF polynucleotide would have the effect of increasing production of a TF even further in the plant. In specific embodiments, the TF polynucleotide may be expressed primarily or entirely in specific regions or cells (such as roots, shoots, leaves etc. of the plant).

In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates. In certain specific embodiments, a TF is under the control of a seed-specific promoter, and may optionally comprise other regulatory elements that result in constitutive or inducible expression of a TF.

In one embodiment, the TF nucleic acid sequence is operably linked to a gene expression sequence, which directs the expression of the TF within the cell. A "gene expression sequence," as used herein, is any regulatory nucleotide sequence, such as a promoter sequence or promoter-enhancer combination, which facilitates the efficient transcription and translation of the nucleotide sequence to which it is operably linked. The gene expression sequence may, for example, be a eukaryotic promoter or a viral promoter, such as a constitutive or inducible promoter. Promoters and enhancers consist of short arrays of DNA sequences that interact specifically with cellular proteins involved in transcription, for instance, as discussed in Maniatis et al., 1987, Science 236:1237. Promoter and enhancer elements have been isolated from a variety of eukaryotic sources including genes in plant, yeast, insect and mammalian cells and viruses (analogous control elements, i.e., promoters, are also found in prokaryotes). In some embodiments, the nucleic acid is linked to a gene expression sequence which permits expression of the nucleic acid in a plant cell. A sequence which permits expression of the nucleic acid in a plant cell is one which is selectively active in the particular plant cell and thereby causes the expression of the nucleic acid in these cells. Those of ordinary skill in the art will be able to easily identify promoters that are capable of expressing a nucleic acid in a cell based on the type of plant cell.

A number of promoters can be used in the practice of the invention. The promoters can be selected based on the desired outcome. Generally, the nucleotide sequence and the modulator sequences can be combined with promoters of choice to alter gene expression if the target sequences in the tissue or organ of choice. Thus, the nucleotide sequence or modulator nucleotide sequence can be combined with constitutive, tissue-preferred, inducible, developmental, or other promoters for expression in plants depending upon the desired outcome.

The selection of a particular promoter and enhancer depends on what cell type is to be used and the mode of delivery. For example, a wide variety of promoters have been isolated from plants and animals, which are functional not only in the cellular source of the promoter, but also in numerous other plant species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, and promoters from other open reading frames in the T-DNA, such as ORF7, etc. Promoters isolated from plant viruses include the 35S promoter from cauliflower mosaic virus. Promoters that have been isolated and reported for use in plants include ribulose-1,3-biphosphate carboxylase small subunit promoter, phaseolin promoter, etc. Thus, a variety of promoters and regulatory elements may be used in the expression vectors of the present invention.

Promoters useful in the present compositions and methods include both natural constitutive and inducible promoters as well as engineered promoters. The CaMV promoters are examples of constitutive promoters. Other constitutive mammalian promoters include, but are not limited to, polymerase promoters as well as the promoters for the following genes: hypoxanthine phosphoribosyl transferase ("HPTR"), adenosine deaminase, pyruvate kinase, and alpha-actin. Promoters useful as expression elements of the invention also include inducible promoters. Inducible promoters are expressed in the presence of an inducing agent. For example, a metallothionein promoter can be induced to promote transcription in the presence of certain metal ions. Other inducible promoters are known to those of ordinary skill in the art. The in vivo expression element can include, as necessary, 5' non-transcribing and 5' non-translating sequences involved with the initiation of transcription, and can optionally include enhancer sequences or upstream activator sequences.

In some embodiments an inducible promoter can be used to allow control of nucleic acid expression through the presentation of external stimuli (e.g., environmentally inducible promoters). Thus, the timing and amount of nucleic acid expression can be controlled in some cases. Non-limiting examples of expression systems, promoters, inducible promoters, environmentally inducible promoters, and enhancers are well known to those of ordinary skill in the art. Examples include those described in International Patent Application Publications WO 00/12714, WO 00/11175, WO 00/12713, WO 00/03012, WO 00/03017, WO 00/01832, WO 99/50428, WO 99/46976 and U.S. Pat. Nos. 6,028,250, 5,959,176, 5,907,086, 5,898,096, 5,824,857, 5,744,334, 5,689,044, and 5,612,472. A general descriptions of plant expression vectors and reporter genes can also be found in Gruber et al., 1993, "Vectors for Plant Transformation," in Methods in Plant Molecular Biology & Biotechnology, Glich et al., Eds., p. 89-119, CRC Press.

For plant expression vectors, viral promoters that can be used in certain embodiments include the 35S RNA and 19S RNA promoters of CaMV (Brisson et al., Nature, 1984, 310:511; Odell et al., Nature, 1985, 313:810); the full-length transcript promoter from Figwort Mosaic Virus (FMV) (Gowda et al., 1989, J. Cell Biochem., 13D: 301) and the coat protein promoter to TMV (Takamatsu et al., 1987, EMBO J. 6:307). Alternatively, plant promoters such as the light-inducible promoter from the small subunit of ribulose bis-phosphate carboxylase (ssRUBISCO) (Coruzzi et al., 1984, EMBO J., 3:1671; Broglie et al., 1984, Science, 224:838); mannopine synthase promoter (Velten et al., 1984, EMBO J., 3:2723) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., 1986, Mol. Cell. Biol., 6:559; Severin et al., 1990, Plant Mol. Biol., 15:827) may be used. Exemplary viral promoters which function constitutively in eukaryotic cells include, for example, promoters from the simian virus, papilloma virus, adenovirus, human immunodeficiency virus, Rous sarcoma virus, cytomegalovirus, the long terminal repeats of Moloney leukemia virus and other retroviruses, and the thymidine kinase promoter of herpes simplex virus. Other constitutive promoters are known to those of ordinary skill in the art.

In embodiments, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., Proc. Natl. Acad. Sci., U.S.A., 90:4567, 1993); In2-1 and In2-2 regulator sequences which are activated by substituted benzenesulfonamides, e.g., herbicide safeners (Hershey et al., Plant Mol. Biol., 17:679, 1991); and the GRE regulatory sequences which are induced by glucocorticoids (Schena et al., Proc. Natl. Acad Sci., U.S.A., 88:10421, 1991). Other promoters, both constitutive and inducible will be known to those of skill in the art.

A number of inducible promoters are known in the art. For resistance genes, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al., 1983, Neth. J. Plant Pathol. 89:245-254; Uknes et al., 1992, Plant Cell 4:645-656; and Van Loon, 1985, Plant Mol. Virol. 4:111-116. Of particular interest are promoters that are expressed locally at or near the site of pathogen infection. See, for example, Marineau et al., 1987, Plant Mol. Biol. 9:335-342; Matton et al., 1989, Molecular Plant-Microbe Interactions 2:325-331; Somsisch et al., 1986, Proc. Natl. Acad. Sci. USA 83:2427-2430; Somsisch et al., 1988, Mol. Gen. Genet. 2:93-98; and Yang, 1996, Proc. Natl. Acad. Sci. USA 93:14972-14977. See also, Chen et al., 1996, Plant J. 10:955-966; Zhang et al., 1994, Proc. Natl. Acad. Sci. USA 91:2507-2511; Warner et al., 1993, Plant J. 3:191-201; Siebertz et al., 1989, Plant Cell 1:961-968; U.S. Pat. No.

5,750,386; Cordero et al., 1992, Physiol. Mol. Plant Path. 41:189-200; and the references cited therein.

Additionally, as pathogens find entry into plants through wounds or insect damage, a wound-inducible promoter may be used in the DNA constructs of the invention. Such wound-inducible promoters include potato proteinase inhibitor (pin II) gene (Ryan, 1990, Ann. Rev. Phytopath. 28:425-449; Duan et al., 1996, Nature Biotechnology 14:494-498); wun1 and wun2, U.S. Pat. No. 5,428,148; win1 and win2 (Stanford et al., 1989, Mol. Gen. Genet. 215:200-208); systemin (McGurl et al., 1992, Science 225: 1570-1573); WIPI (Rohmeier et al., 1993, Plant Mol. Biol. 22:783-792; Eckelkamp et al., 1993, FEBS Letters 323:73-76); MPI gene (Corderok et al., 1994, Plant J. 6(2):141-150); and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al., 1991, Proc. Natl. Acad. Sci. USA 88:10421-10425 and McNellis et al., 1998, Plant J. 14(2):247-257) and tetramiR167e-inducible and tetramiR167e-repressible promoters (see, for example, Gatz et al., 1991, Mol. Gen. Genet. 227:229-237, and U.S. Pat. Nos. 5,814,618 and 5,789,156), herein incorporated by reference.

Where enhanced expression in particular tissues is desired, tissue-preferred promoters can be utilized. Tissue-preferred promoters include those described by Yamamoto et al., 1997, Plant J. 12(2):255-265; Kawamata et al., 1997, Plant Cell Physiol. 38(7):792-803; Hansen et al., 1997, Mol. Gen Genet. 254(3):337-343; Russell et al., 1997, Transgenic Res. 6(2):157-168; Rinehart et al., 1996, Plant Physiol. 112(3):1331-1341; Van Camp et al., 1996, Plant Physiol. 112(2):525-535; Canevascini et al., 1996, Plant Physiol. 12(2):513-524; Yamamoto et al., 1994, Plant Cell Physiol. 35(5):773-778; Lam, 1994, Results Probl. Cell Differ. 20:181-196; Orozco et al., 1993, Plant Mol. Biol. 23(6): 1129-1138; Matsuoka et al., 1993, Proc Natl. Acad. Sci. USA 90(20):9586-9590; and Guevara-Garcia et al., 1993, Plant J 4(3):495-505.

In certain embodiments, to provide pericycle-specific expression, any of a number of promoters from genes in *Arabidopsis* can be used. In some embodiments, the promoter from one (or more) of the following genes may be used: (i) At1g11080, (ii) At3g60160, (iii) At1g24575, (iv) At3g45160, or (v) At1g23130. In specific embodiments, we will also use (vi) promoter elements from the GFP-marker line used in Gifford et al. (in preparation) (see also, Bonke et al., 2003, Nature 426, 181-6; Tian et al., 2004, Plant Physiol 135, 25-38). Several of the predicted genes have a number of potential orthologs in rice and poplar and thus are predicted that they will be applicable for use in crop species; (i) Os04g44410, Os10g39560, Os06g51370, Os02g42310, Os01g22980, Os05g06660, and Poptr1 #568263, Poptr1 #555534, Poptr1 #365170; (ii) Os04g49900, Os04g49890, Os01g67580, and Poptr1 #87573, Poptr1 #80582, Poptr1 #565079, Poptr1 #99223.

Promoters used in the nucleic acid constructs of the present invention can be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

An efficient plant promoter that may be used in specific embodiments is an "overproducing" or "overexpressing" plant promoter. Overexpressing plant promoters that can be used in the compositions and methods provided herein include the promoter of the small sub-unit ("ss") of the ribulose-1,5-biphosphate carboxylase from soybean (e.g., Berry-Lowe et al., 1982, J. Molecular & App. Genet., 1:483), and the promoter of the chlorophyll a-b binding protein. These two promoters are known to be light-induced in eukaryotic plant cells. For example, see Cashmore, Genetic Engineering of plants: An Agricultural Perspective, p. 29-38; Coruzzi et al., 1983, J. Biol. Chem., 258:1399; and Dunsmuir et al., 1983, J. Molecular & App. Genet., 2:285.

The promoters and control elements of, e.g., SUCS (root nodules; broadbean; Kuster et al., 1993, Mol Plant Microbe Interact 6:507-14) for roots can be used in compositions and methods provided herein to confer tissue specificity.

In certain embodiment, two promoter elements can be used in combination, such as, for example, (i) an inducible element responsive to a treatment that can be provided to the plant prior to N-fertilizer treatment, and (ii) a plant tissue-specific expression element to drive expression in the specific tissue alone.

Any promoter or other expression element described herein or known in the art may be used either alone or in combination with any other promoter or other expression element described herein or known in the art. For example, promoter elements that confer tissue specific expression of a gene can be used with other promoter elements conferring constitutive or inducible expression.

Isolating Related Promoter Sequences:

Promoter and promoter control elements that are related to those described in herein can also be used. Related promoters may be used that exhibit at least 80% sequence identity, preferably at least 85%, more preferably at least 90%, and most preferably at least 95%, even more preferably, at least 96%, at least 97%, at least 98% or at least 99% sequence identity. Such sequence identity can be calculated by the algorithms and computers programs described above. Usually, such sequence identity is exhibited in an alignment region that is at least 75% of the length of a sequence or corresponding full-length sequence of a promoter described herein; more usually at least 80%; more usually, at least 85%, more usually at least 90%, and most usually at least 95%, even more usually, at least 96%, at least 97%, at least 98% or at least 99% of the length of a sequence of a promoter described herein.

The vector backbone can be any of those typical in the art such as plasmids, viruses, artificial chromosomes, BACs, YACs and PACs and vectors of the sort described by (a)

BAC: Shizuya et al., 1992, Proc. Natl. Acad. Sci. USA 89: 8794-8797; Hamilton et al., 1996, Proc. Natl. Acad. Sci. USA 93: 9975-9979; (b) YAC: Burke et al., 1987, Science 236:806-812; (c) PAC: Sternberg N. et al., 1990, Proc Natl Acad Sci USA. January; 87(1):103-7; (d) Bacteria-Yeast Shuttle Vectors: Bradshaw et al., 1995, Nucl Acids Res 23: 4850-4856; (e) Lambda Phage Vectors: Replacement Vector, e.g., Frischauf et al., 1983, J. Mol. Biol. 170: 827-842; or Insertion vector, e.g., Huynh et al., 1985, In: Glover N M (ed) DNA Cloning: A practical Approach, Vol. 1 Oxford: IRL Press; T-DNA gene fusion vectors: Walden et al., 1990, Mol Cell Biol 1: 175-194; and (g) Plasmid vectors: Sambrook et al., infra.

Typically, the construct comprises a vector containing a sequence of the present invention operationally linked to any marker gene. Although many marker genes can be used, Green Fluorescent Protein (GFP) is commonly used. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin (see below). Vectors can also include origins of replication, scaffold attachment regions (SARs), markers, homologous sequences, introns, etc.

Tissue or Cell-type Specific Transcription:

The invention also provides a method of providing increased transcription of a nucleic acid sequence in a selected tissue, such as vegetative tissues, leaves, seeds, fruit, etc. The method comprises growing a plant having integrated in its genome a nucleic acid construct comprising, an exogeneous gene encoding a TF, said gene operably associated with a tissue specific promoter, whereby transcription of said gene is increased (or decreased) in said selected tissue.

Specific promoters may be used in the compositions and methods provided herein. As used herein, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used in the compositions and methods of the present invention, include RCc2 and RCc3, promoters that direct root-specific gene transcription in rice (Xu et al., 1995, Plant Mol. Biol. 27:237 and TobRB27, a root-specific promoter from tobacco (Yamamoto et al., 1991, Plant Cell 3:371). Examples of tissue-specific promoters under developmental control include promoters that initiate transcription only in certain tissues or organs, such as roots.

"Preferential transcription" is defined as transcription that occurs in a particular pattern of cell types or developmental times or in response to specific stimuli or combination thereof. Non-limitative examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or in a leaf, is useful (1) to modulate root size, shape, and development; (2) to modulate the number of roots, or root hairs; (3) to modulate mineral, fertilizer, or water uptake; (4) to modulate transport of nutrients; or (4) to modulate energy or nutrient usage in relation to other organs and tissues. Up-regulation and transcription down-regulation is useful for these applications. For instance, genes, transcripts, and/or polypeptides that increase growth, for example, may require up-regulation of transcription. In contrast, transcriptional down-regulation may be desired to inhibit nutrient usage in a root to be directed to the leaf instead, for instance.

Typically, promoter or control elements, which provide preferential transcription in cells, tissues, or organs of a root, produce transcript levels that are statistically significant as compared to other cells, organs or tissues. For preferential up-regulation of transcription, promoter and control elements produce transcript levels that are above background of the assay.

Root-preferred promoters are known and can be selected from the many available from the literature. See, for example, Hire et al., 1992, Plant Mol. Biol. 20(2): 207-218 (soybean root-preferred glutamine synthetase gene); Keller and Baumgartner, 1991, Plant Cell 3(10):1051-1061 (root-preferred control element in the GRP 1.8 gene of French bean); Sanger et al., 1990, Plant Mol. Biol. 14(3):433-443 (root-preferred promoter of the mannopine synthase (MAS) gene of *Agrobacterium tumefaciens*); Miao et al., 1991, Plant Cell 3(1):11-22 (full-length cDNA clone encoding cytosolic glutamine synthetase (GS), which is expressed in roots and root nodules of soybean). Bogusz et al., 1990, Plant Cell 2(7):633-641 (root-preferred promoters from hemoglobin genes from the nitrogen-fixing nonlegume *Parasponia andersonii* and the related non-nitrogen-fixing nonlegume *Trema tomentosa*). Leach and Aoyagi, 1991, Plant Science (Limerick) 79(1):69-76 (ro1C and ro1D root-inducing genes of *Agrobacterium rhizogenes*); Teeri et al., 1989, EMBO J. 8(2):343-350) (octopine synthase and TR2' gene); (VfENOD-GRP3 gene promoter); Kuster et al., 1995, Plant Mol. Biol. 29(4):759-772 and Capana et al., 1994, Plant Mol. Biol. 25(4):681-691 ro1B promoter. See also U.S. Pat. Nos. 5,837,876; 5,750,386; 5,633,363; 5,459,252; 5,401,836; 5,110,732; and 5,023,179, root-specific glutamine synthetase (see Tingey et al., 1987, EMBO J., 6:1-9; Edwards et al., 1990, PNAS, 87:3439-3463). In addition, promoters of the above-listed orthologous genes in other plant species can be identified and used in the compositions and methods provided herein.

In specific embodiments, the compositions and methods provided herein use leaf-specific promoters operably associated to a nucleotide encoding a TF. In certain embodiments, the promoter is a constitutive or inducible promoter. In another specific embodiment, the compositions and methods provided herein use vegetative tissue-specific promoters operably associated to a nucleotide encoding a TF. In certain embodiments, the promoter is a constitutive or inducible promoter.

Selection and Identification of Transfected Host Cells:

The method of the present invention comprises detecting host cells that express a selectable marker. In certain embodiments, the step of detecting host cells that express the selectable marker is performed by Fluorescence Activated Cell Sorting (FACS) in the methods of the present invention. Fluorescence activated cell sorting (FACS) is a well-known method for separating particles, including cells, based on the fluorescent properties of the particles (see, e.g., Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

Desired altered plants may be obtained by using the methods described herein. In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be also to identify plant or plant cell transformants containing the gene constructs of the present invention. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Screening of Transformed Plants for Improved Agronomic Traits

According to the present invention, to obtain plants with desired agronomic characteristics (e.g., size of any part of the plant, yield, or growth and the like), the transformed plants may be screened for those exhibiting the desired physiological alteration. Alternatively, the transformed plants may be directly screened for those exhibiting the desired agronomic changes. A plant with the desired improvement can be isolated by screening the engineered plants for altered expression pattern or level of TF. A plant can also be screened for nutrient uptake, overall increased plant growth rate, enhanced vegetative yield, improved reproductive yields, increased levels of glutamine or asparagine, or increased nitrogen usage or storage. The screening of the engineered plants can involve Southern analysis to confirm the presence and number of transgene insertions; Northern analysis, RNase protection, primer extension, reverse transcriptase/PCR and the like to measure mRNA levels; measuring the amino acid composition, free amino acid pool or total nitrogen content of various plant tissues; measuring growth rates in terms of fresh weight gains over time; or measuring plant yield in terms of total dry weight and/or total seed weight, or a combination of any of the above methods. The procedures and methods for examining these parameters are well known to those skilled in the art. In other embodiments, the screening of the transformed plants may be for improved agronomic characteristics (e.g., faster growth, greater vegetative or reproductive yields, or improved protein contents, etc.), as compared to unengineered progenitor plants, when cultivated under growth conditions (i.e., cultivated using soils or media containing or receiving sufficient amounts of nitrogen nutrients to sustain healthy plant growth). Plants exhibiting increased growth and/or yield as compared with wild-type plants can be selected by visual observation.

Cells:

Optionally, germ line cells may be used in the methods described herein rather than, or in addition to, somatic cells. The term "germ line cells" refers to cells in the plant organism which can trace their eventual cell lineage to either the male or female reproductive cell of the plant. Other cells, referred to as "somatic cells" are cells which give rise to leaves, roots and vascular elements which, although important to the plant, do not directly give rise to gamete cells. Somatic cells, however, also may be used. With regard to callus and suspension cells which have somatic embryogenesis, many or most of the cells in the culture have the potential capacity to give rise to an adult plant. If the plant originates from single cells or a small number of cells from the embryogenic callus or suspension culture, the cells in the callus and suspension can therefore be referred to as germ cells. In the case of immature embryos which are prepared for treatment by the methods described herein, certain cells in the apical meristem region of the plant have been shown to produce a cell lineage which eventually gives rise to the female and male reproductive organs. With many or most species, the apical meristem is generally regarded as giving rise to the lineage that eventually will give rise to the gamete cells. An example of a non-gamete cell in an embryo would be the first leaf primordia in corn which is destined to give rise only to the first leaf and none of the reproductive structures.

Plant Regeneration:

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al., 1984, in Cell Culture and Somatic Cell Genetics of Plants, Vols. I, II, and III, Laboratory Procedures and Their Applications (Academic Press); and Weissbach et al., 1989, Methods For Plant Mol. Biol.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Normally, a plant cell is regenerated to obtain a whole plant from the transformation process. The term "growing" or "regeneration" as used herein means growing a whole plant from a plant cell, a group of plant cells, a plant part (including seeds), or a plant piece (e.g., from a protoplast, callus, or tissue part). Regeneration can occur from protoplasts, callus, explants, organs or other parts. The regeneration of plants from either single plant protoplasts or various explants is well known in the art. See, for example, Methods for Plant Molecular Biology, A. Weissbach and H. Weissbach, eds., 1988, Academic Press, Inc., San Diego, Calif. This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., 1994, Springer, New York 1994; Corn and Corn Improvement, 3rd edition, Sprague and Dudley Eds., 1988, American Society of Agronomy, Madison, Wis. The regeneration of plants containing the foreign gene introduced by *Agrobacterium* from leaf explants can be achieved as described by Horsch et al., 1985, Science, 227:1229-1231. In this procedure, transformants are grown in the presence of a selection agent and in a medium that induces the regeneration of shoots in the plant species being transformed as described by Fraley et al., 1983, Proc. Natl. Acad. Sci. (U.S.A.), 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

In vegetatively propagated crops, the mature transgenic plants can be propagated by utilizing cuttings or tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The resulting inbred plant produces seed containing the newly introduced foreign gene(s). These seeds can be grown to produce plants that would produce the selected phenotype, e.g., increased lateral root growth, uptake of nutrients, overall plant growth and/or vegetative or reproductive yields.

The present disclosure includes parts obtained from the regenerated plant, such as flowers, seeds, leaves, branches, fruit, and the like, provided that these parts comprise cells comprising the TF nucleic acid sequence of the present invention. Progeny and variants, and mutants of the regenerated plants are also included within the scope of the invention, provided that these parts comprise the introduced nucleic acid sequences. Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

This disclosure provides a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Plants and Plant Cells:

This disclosure also provides a plant cell having the nucleotide sequence constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

In certain embodiments, a plant cell comprises a TF nucleotide sequence operably associated with a vegetative tissue specific promoter, which is optionally a constitutive or inducible promoter. In other embodiments, a plant cell comprises multiple copies of a TF operably associated with a vegetative tissue specific promoter. In specific embodiments provided herein are plants (and plant cells thereof) that overexpress, constitutionally express and/or inducibly express a TF in the vegetative tissues of the plant, as compared to other tissues in the plant and/or as compared to a wild type plant.

The present disclosure also provides a plant comprising a plant cell as disclosed. Transformed seeds and plant parts are also encompassed. In addition to a plant, the present invention provides any clone of such a plant, seed, selfed or hybrid progeny and descendants, and any part of any of these, such as cuttings, seed. The invention provides any plant propagule that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant. Plant extracts and derivatives are also provided.

Any species of woody, ornamental or decorative, crop or cereal, fruit or vegetable plant, and algae (e.g., *Chlamydomonas reinhardtii*) may be used in the compositions and methods provided herein. Non-limiting examples of plants include plants from the genus *Arabidopsis* or the genus *Oryza*. Other examples include plants from the genuses Acorns, *Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

Plants included in the invention are any plants amenable to transformation techniques, including gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, *sequoia*, cedar, oak, etc. Still other examples of plants include, but are not limited to, wheat, cauliflower, tomato, tobacco, corn, *petunia*, trees, etc.

In certain embodiments, plants of the present invention are crop plants (for example, cereals and pulses, maize, wheat, potatoes, tapioca, rice, sorghum, millet, cassava, barley, pea, and other root, tuber, or seed crops. Exemplary cereal crops used in the compositions and methods of the invention include, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). Grain plants that provide seeds of interest include oil-seed plants and leguminous plants. Other seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Other important seed crops are oil-seed rape, sugar beet, maize, sunflower, soybean, and sorghum. Leguminous plants include beans and peas. Beans include guar, locust bean, fenugreek, soybean, garden beans, cowpea, mungbean, lima bean, fava bean, lentils, chickpea, etc.

Horticultural plants to which the present invention may be applied may include lettuce, endive, and vegetable brassicas including cabbage, broccoli, and cauliflower, and carnations and geraniums. The present invention may also be applied to tobacco, cucurbits, carrot, strawberry, sunflower, tomato, pepper, *chrysanthemum*, poplar, *eucalyptus*, and pine.

As specific example, the present disclosure may be used for transformation of plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

Cultivation

Methods of cultivation of plants are well known in the art. For example, for the cultivation of wheat see Alcoz et al., 1993, Agronomy Journal 85:1198-1203; Rao and Dao, 1992, J. Am. Soc. Agronomy 84:1028-1032; Howard and Lessman, 1991, Agronomy Journal 83:208-211; for the cultivation of corn see Tollenear et al., 1993, Agronomy Journal 85:251-255; Straw et al., Tennessee Farm and Home Science: Progress Report, Spring 1993, 166:20-24; Miles, S. R., 1934, J. Am. Soc. Agronomy 26:129-137; Dara et al., 1992, J. Am. Soc. Agronomy 84:1006-1010; Binford et al., 1992, Agronomy Journal 84:53-59; for the cultivation of soybean see Chen et al., 1992, Canadian Journal of Plant Science 72:1049-1056; Wallace et al., 1990, Journal of Plant Nutrition 13:1523-1537; for the cultivation of rice see Oritani and Yoshida, 1984, Japanese Journal of Crop Science 53:204-212; for the cultivation of linseed see Diepenbrock and Porksen, 1992, Industrial Crops and Products 1:165-173; for the cultivation of tomato see Grubinger et al., 1993, Journal of the American Society for Horticultural Science 118:212-216; Cerne, M., 1990, Acta Horticulture 277:179-182; for the cultivation of pineapple see Magistad et al., 1932, J. Am. Soc. Agronomy 24:610-622; Asoegwu, S. N., 1988, Fertilizer Research 15:203-210; Asoegwu, S. N., 1987, Fruits 42:505-509; for the cultivation of lettuce see Richardson and Hardgrave, 1992, Journal of the Science of Food and Agriculture 59:345-349; for the cultivation of mint see Munsi, P. S., 1992, Acta Horticulturae 306:436-443; for the cultivation of chamomile see Letchamo, W., 1992, Acta Horticulturae 306:375-384; for the cultivation of tobacco see Sisson et al., 1991, Crop Science 31:1615-1620; for the cultivation of potato see Porter and Sisson, 1991, American Potato Journal, 68:493-505; for the cultivation of *brassica* crops see Rahn et al., 1992, Conference "Proceedings, second congress of the European Society for Agronomy" Warwick Univ., p. 424-425; for the cultivation of banana see Hegde and Srinivas, 1991, Tropical Agriculture 68:331-334; Langenegger and Smith, 1988, Fruits 43:639-643; for the cultivation of strawberries see Human and Kotze, 1990, Communications in Soil Science and Plant Analysis 21:771-782; for the cultivation of sorghum see Mahalle and Seth, 1989, Indian Journal of Agricultural Sciences 59:395-397; for the cultivation of plantain see Anjorin and Obigbesan, 1985, Conference "International Cooperation for Effective Plantain and Banana Research" Proceedings of the third meeting. Abidjan, Ivory Coast, p. 115-117; for the cultivation of sugar cane see Yadav, R. L., 1986, Fertiliser News 31:17-22; Yadav and Sharma, 1983, Indian Journal of Agricultural Sciences 53:38-43; for the cultivation of sugar beet see Draycott et al., 1983, Conference "Symposium Nitrogen and Sugar Beet" International Institute for Sugar Beet Research—Brussels Belgium, p. 293-303. See also Goh and Haynes, 1986, "Nitrogen and Agronomic Practice" in Mineral Nitrogen in the Plant-Soil System, Academic Press, Inc., Orlando, Fla., p. 379-468; Engelstad, 0. P., 1985, Fertilizer Technology and Use, Third Edition, Soil Science Society of America, p. 633; Yadav and Sharmna, 1983, Indian Journal of Agricultural Sciences, 53:3-43.

Products of Transgenic Plants

Engineered plants exhibiting the desired physiological and/or agronomic changes can be used directly in agricultural production.

Thus, provided herein are products derived from the transgenic plants or methods of producing transgenic plants provided herein. In certain embodiments, the products are commercial products. Some non-limiting example include genetically engineered trees for e.g., the production of pulp, paper, paper products or lumber; tobacco, e.g., for the production of cigarettes, cigars, or chewing tobacco; crops, e.g., for the production of fruits, vegetables and other food, including grains, e.g., for the production of wheat, bread, flour, rice, corn; and canola, sunflower, e.g., for the production of oils or biofuels.

In certain embodiments, commercial products are derived from a genetically engineered (e.g., comprising overexpression of a TF in the vegetative tissues of the plant) species of woody, ornamental or decorative, crop or cereal, fruit or vegetable plant, and algae (e.g., *Chlamydomonas reinhardtii*), which may be used in the compositions and methods provided herein. Non-limiting examples of plants include plants from the genus *Arabidopsis* or the genus *Oryza*. Other examples include plants from the genuses Acorns, *Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

In some embodiments, commercial products are derived from a genetically engineered gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

In certain embodiments, commercial products are derived from a genetically engineered (e.g., comprising overexpression of a TF in the leaves or seeds of the plant) woody species, such as poplar, pine, *sequoia*, cedar, oak, etc.

In other embodiments, commercial products are derived from a genetically engineered (e.g., comprising overexpression of a TF in the vegetative tissues of the plant) plant including, but are not limited to, wheat, cauliflower, tomato, tobacco, corn, *petunia*, trees, etc.

In certain embodiments, commercial products are derived from a genetically engineered crop plants, for example, cereals and pulses, maize, wheat, potatoes, tapioca, rice, sorghum, millet, cassaya, barley, pea, and other root, tuber, or seed crops. In one embodiment, commercial products are derived from a genetically engineered (e.g., comprising overexpression of TFS of interest in the vegetative tissues of the plant) cereal crops, including, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). In another embodiments, commercial products are derived from a genetically engineered (e.g., comprising overexpression of TFs of interest in leaf or seed tissue of the plant) grain plants that provide seeds of interest, oil-seed plants and leguminous plants. In other embodiments, commercial products are derived from a genetically engineered grain seed plants, such as corn, wheat, barley, rice, sorghum, rye, etc. In yet other embodiments, commercial products are derived from a genetically engineered (e.g., comprising overexpression TFs of interest) oil seed plants, such as cotton, soybean, safflower, sunflower, *Brassica*, maize, alfalfa, palm, coconut, etc. In certain embodiments, commercial products are derived from a genetically engineered oil-seed rape, sugar beet, maize, sunflower, soybean, or sorghum. In some embodiments, commercial products are derived from a genetically engineered leguminous plants, such as beans and peas (e.g., guar, locust bean, fenugreek, soybean, garden beans, cowpea, mungbean, lima bean, fava bean, lentils, chickpea, etc.)

In certain embodiments, commercial products are derived from a genetically engineered horticultural plant of the present invention, such as lettuce, endive, and vegetable brassicas including cabbage, broccoli, and cauliflower, and carnations and geraniums; tomato, tobacco, cucurbits, carrot, strawberry, sunflower, tomato, pepper, *chrysanthemum*, poplar, *eucalyptus*, and pine.

In still other embodiments, commercial products are derived from a genetically engineered corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

Kits:

In one aspect, the present invention provides kits comprising the compositions for carrying out any of the above-mentioned methods, optionally including instructions for use of the composition e.g., for the overexpression or under-expression of one or more TFs. A "kit" may be a package comprising one or more compositions of the invention and the instructions, and/or analogs, derivatives, or functionally equivalent compositions thereof. Thus, for example, the kit can include a description of use of the composition for participation in any technique associated in the overexpression or under-expression of genes. The kit can include a description of use of the compositions as discussed herein. Instructions also may be provided for use of the composition in any suitable technique as previously described. The instructions may be of any form provided in connection with the composition. The kits may have one or more containers, which may contain the inventive composition and other ingredients as previously described. The kits also may contain instructions for preparing, mixing, diluting, and/or administrating the compositions in some cases. The kits also can include other containers with one or more solvents, surfactants, preservative and/or diluents (e.g., normal saline (0.9% NaCl), or 5% dextrose and the like) as well as containers for mixing, diluting and/or administrating the compositions. The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition. Suitable solvents are well known, for example as previously described, and are available in the literature.

The role for potential or identified TFs in N-response may be evaluated by techniques known in the art. A convenient method for investigating TFs is the TARGET system which uses transient transformation of a plasmid containing a glucocorticoid receptor (GR)-tagged TF in protoplasts to study the genome-wide effects of TF activation. (See U.S. patent application Ser. No. 14/457,402, and PCT application no. PCT/US2016/016811). The components of the TARGET system are described below.

Localization Signals and Inducing Agents:

The glucorticoid receptor (GR) may be used as the inducible cellular localization signal in the chimeric protein encoded by the nucleic acid construct. In the case of the a TF-GR chimeric protein, dexamethasone may be used as the inducing agent. Alternately, another glucocorticoid may be used instead of dexamethasone. Treatment with dexamethasone releases the glucocorticoid receptor from sequestration in the cytoplasm, allowing the TF-GR fusion protein to access its target genes (e.g., in the nucleus). The GR is not the only such inducible cellular localization signal that may be used in this method. Any receptor component or other protein known in the art that is capable of being released from sequestration or otherwise re-localized to the destination of the transcription factor component by treatment of the protoplasts with an inducing agent may potentially be used in the TARGET system.

Expression System and Selectable Markers:

Using any gene transfer technique, such as the above-listed techniques (of Section 5.2), an expression vector harboring the nucleic acid may be transformed into a cell to achieve temporary or prolonged expression. Any suitable expression system may be used, so long as it is capable of undergoing transformation and expressing of the precursor nucleic acid in the cell. In one embodiment, a pET vector (Novagen, Madison, Wis.), or a pBI vector (Clontech, Palo Alto, Calif.) is used as the expression vector. In some embodiments an expression vector further encoding a green fluorescent protein ("GFP") is used to allow simple selection of transfected cells and to monitor expression levels. Non-limiting examples of such vectors include Clontech's "Living Colors Vectors" pEYFP and pEYFP-C.

The recombinant construct of the present invention may include a selectable marker for propagation of the construct. For example, a construct to be propagated in bacteria preferably contains an antibiotic resistance gene, such as one that confers resistance to kanamycin, tetracycline, strepto-mycin, or chloramphenicol. Suitable vectors for propagating the construct include plasmids, cosmids, bacteriophages or viruses, to name but a few.

In some embodiments, the selectable marker encoded by the nucleic acid molecule used in the method of the invention is a fluorescent selection marker. A fluorescent selection marker that can be used in the method of the invention includes, but is not limited to, green fluorescent protein, yellow fluorescent protein, red fluorescent protein, cyan fluorescent protein, or blue fluorescent protein. In a specific embodiment, the fluorescent selection marker used in the method of the invention is red fluorescent protein. In certain embodiments, the step of detecting host cells that express the selectable marker is performed by Fluorescence Activated Cell Sorting (FACS). Any selectable marker known in the art that may be encoded in the nucleic acid construct and which is selectable using a cell sorting or other selection technique may be used to identify those cells that have expressed the nucleic acid construct containing the chimeric protein.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding .beta.-glucuronidase (Jefferson, 1987, Plant Molec Biol. Rep 5:387-405), luciferase (Ow et al., 1986, Science 234:856-859), B and C1 gene products that regulate anthocyanin pigment production (Goff et al., 1990, EMBO J 9:2517-2522).

In some cases, a selectable marker may be included with the nucleic acid being delivered to the cell. A selectable marker may refer to the use of a gene that encodes an enzymatic or other detectable activity (e.g., luminescence or fluorescence) that confers the ability to distinguish cells expressing the nucleic acid construct from those that do not. A selectable marker may confer resistance to an antibiotic or drug upon the cell in which the selectable marker is expressed. Selectable markers may be "dominant" in some cases; a dominant selectable marker encodes an enzymatic or other activity (e.g., luminescence or fluorescence) that can be detected in any cell or cell line.

In some embodiments, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II. Other suitable markers will be known to those of skill in the art.

Detecting the Level of mRNA Expressed in Host Cells:

The methods of the present invention comprise a step of detecting the level of mRNA expressed in the host cells of the invention.

In some embodiments, the level of mRNA expressed in host cells is determined by quantitative real-time PCR (qPCR), a method for DNA amplification in which fluorescent dyes are used to detect the amount of PCR product after each PCR cycle. (Higuchi et al., 1992; Simultaneous amplification and detection of specific DNA-sequences. Bio-Technology 10(4), 413-417].). The qPCR method has become the tool of choice for many scientists because of method's dynamic range, accuracy, high sensitivity, specificity and speed. Quantitative PCR is carried out in a thermal cycler with the capacity to illuminate each sample with a beam of light of a specified wavelength and detect the fluorescence emitted by the excited fluorochrome. The thermal cycler is also able to rapidly heat and chill samples thereby taking advantage of the physicochemical properties of the nucleic acids and DNA polymerase.

In some embodiments, the level of mRNA expressed in host cells is determined by high throughput sequencing (Next-generation sequencing; also 'Next-gen sequencing' or NGS). =NGS methods are highly parallelized processes that enable the sequencing of thousands to millions of molecules at once. Popular NGS methods include pyrosequencing developed by 454 Life Sciences (now Roche), which makes use of luciferase to read out signals as individual nucleotides are added to DNA templates, Illumina sequencing that uses reversible dye-terminator techniques that adds a single nucleotide to the DNA template in each cycle and SOLiD sequencing by Life Technologies that sequences by preferential ligation of fixed-length oligonucleotides.

In some embodiments, the level of mRNA expressed in host cells is determined by gene microarrays. A microarray works by exploiting the ability of a given mRNA molecule to bind specifically to, or hybridize to, the DNA template from which it originated. By using an array containing many DNA samples, it can be determined in a single experiment, the expression levels of hundreds or thousands of genes within a cell by measuring the amount of mRNA bound to each site on the array. With the aid of a computer, the amount of mRNA bound to the spots on the microarray is precisely measured, generating a profile of gene expression in the cell.

Detecting TF Binding to Gene Targets

In some embodiments, the method comprises detection of the level of TF binding to gene targets by ChIP-Seq analysis. ChIP-Seq analysis utilizes chromatin immunoprecipitation in parallel with DNA sequencing to map the binding sites of a TF or other protein of interest. First, protein interactions with chromatin are cross-linked and fragmented. Then, immunoprecipitation is used to isolate the TF with bound chromatin/DNA. The associated chromatin/DNA fragments are sequenced to determine the gene location of protein binding. Other assays known in the art may be used to detect the location of TF binding to genomic regions of DNA.

In some embodiments, the yeast one hybrid method may be used. The yeast one hybrid method detects protein-DNA interactions, and may be adapted for use in plants. The DNA binding domains unveiled by ChIP-Seq may be cloned upstream of a reporter gene in a vector or may be introduced into the plant genome by homologous recombination, which allows the transcription factor to interact with the DNA element in a natural environment. A fusion protein containing a constitutive TF activation domain and the DNA binding domain of the TF of interest may then be expressed, and the interaction of the binding domain with the DNA will be detected by reporter gene expression. The yeast one hybrid method can thus be used in some embodiments as a way to interrogate the relationship between binding and activation, as only the binding domain of the TF of interest is used in the fusion protein in the heterologous system.

Identifying Conserved Connections Across Species:

In some embodiments, gene networks conserved between *Arabidopsis* (or another model species) and a species of interest may be determined by a data mining approach. In this approach, *Arabidopsis* plants are grown under the same conditions as plants from another species of interest, including perturbation of environmental signals (e.g. nitrogen). RNA is then extracted from the roots and shoots of the plants, and cDNA synthesized from the extracted RNA. A microarray analysis and filtering approach may be used to determine the genes of each species regulated by the environmental signal when compared with control conditions. An ortholog analysis may then determine the genes orthologous between the two species. Data integration and network analysis then allows for the determination of a core translational network.

Examples of embodiments are provided below.

A method for modulating Nitrogen (N) uptake and/or assimilation and/or usage in a plant cell or a plant comprising independently over-expressing or underexpresing one or more N-responsive transcription factors (TF). The one or more N-responsive TFs may be selected from the TFs described in Tables 1, 2, 3, 4, or FIG. 27, or the N-responsive TFs may be any combination of 2 or more from the composite listing of TFs in said Tables or figure. An example of the one or more TFs is CRF4, CDF1, SNZ and/or ERF060. In another example, the one or more TFs may be selected from CRF4, bZIP3 and HHO3, or from CRF4, CDF1, SNZ and ERF060, bZIP1, and HHO3, or from HHO5, HHO6, PHL1, and TGA1. These TFs can be selected and/or combined based on their shared targets in the N-uptake/pathway as shown in FIG. 27. The plant may be a species of woody, ornamental, decorative, crop, cereal, fruit, or vegetable plant. For example, the plant can be a species of a genus selected from the group consisting of: Acorns, *Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia.*

A method for increasing or decreasing N uptake or assimilation in a plant or plant cell by modulating (upregulating or downregulating) the expression of one or more genes encoding for enzyme(s) in the N uptake/assimilation pathway comprising overexpressing one or more TFs inducing said genes, repressing one or more TFs repressing said genes, or a combination of the two. Examples of specific TFs that induce or repress steps and genes in the N-uptake/assimilation pathway are provided in FIG. 27.

A method for repressing (under-expressing) a TF (such as CRF4) to increase the N uptake and/or assimilation in a plant, wherein the repression comprises disrupting a polynucleotide sequence that encodes or controls expression of the TF, or inhibiting translation of an mRNA that encodes for the TF. Disrupting the polynucleotide may comprise editing a segment of a TF gene, or comprises RNA interference (RNAi)-mediated targeting of mRNA encoding TF. Editing may comprise Clustered Regularly Interspaced Short Palindromic Repeats (CRISPR) editing of the gene. RNAi-mediated targeting comprises introducing into the plant cell a microRNA or an shRNA targeted to mRNA encoding the CRF4 gene, and wherein the mRNA is degraded. Inhibiting translation of the mRNA that encodes the CRF4 can be performed using RNAi-mediated targeting of the mRNA.

A method for inducing (over-expressing) a TF (such as SNZ, CDF1, HHO5, HHO6, PHL1 or TGA1 by introducing into a plant cell a polynucleotide (recombinant) encoding the TF and operably linked to a promoter, wherein overexpression of the TF results in increased N uptake and/or assimilation.

A transgenic plant comprising a recombinant polynucleotide encoding a transcription factor (TF) of any of Tables 1, 2, 3, 4, or FIG. 27, wherein the TF is operably linked to a promoter with activity in plants, and wherein the promoter is optionally, a constitutive or inducible promoter, or is associated with a constitutive or inducible regulatory element. The transgenic plant may further comprise one or more additional polynucleotides encoding TFs, each one or more TF being operably linked to a promoter with activity in plants, and wherein the promoter is optionally, a constitutive or inducible promoter, or is associated with a constitutive or inducible regulatory element, and wherein the promoter is the same or different from the promoter of the first polynucleotide.

A plant cell comprising a polynucleotide encoding a transcription factor (TF) of any of Tables 1, 2, 3, or 4, wherein the TF is operably linked to a promoter with activity in plants, and wherein the promoter is optionally, a constitutive or inducible promoter, or is associated with a constitutive or inducible regulatory element. The plant cell may further comprise one or more additional polynucleotides encoding TFs, each one or more TF being operably linked to a promoter with activity in plants, and wherein the promoter is optionally, a constitutive or inducible promoter, or is associated with a constitutive or inducible regulatory element, and wherein the promoter is optionally different from the promoter of the first polynucleotide.

A plant or plant cell comprising one or more polynucleotides encoding a group of TFs, each TF in the group being operably linked to a promoter with activity in plants, wherein the group of TFs collectively induces or represses a gene or genes in the N-uptake/assimilation pathway, resulting in increased or decreased N uptake and assimilation as desired.

The plant or the plant cell may be from a species of woody, ornamental, decorative, crop, cereal, fruit, or vegetable plant. For example, the plant or plant cell may be from Acorns, *Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia.*

A transgenic plant or a plant cell, wherein the said transgenic plant or a plant cell comprises a recombinant polynucleotide operably linked to a promoter to induce overexpression of a transcription factor listed in Tables 1, 2, 3, 4, or FIG. 27. The transgenic plant may further comprise a recombinant polynucleotide which will cause underexpression of one or more additional transcription factors listed in Tables 1, 2, 3, 4 or FIG. 27.

A transgenic plant or a plant cell, wherein the said transgenic plant or a plant cell comprises a polynucleotide which will cause underexpression of one or more transcription factors listed in Tables 1, 2, 3, 4, or FIG. 27.

A product derived from the plant or plant cell, wherein the plant or plant cell comprises one or more polynucleotides which will cause overexpression or underexpression of the one or more transcription factors listed in Tables 1, 2, 3, 4, or FIG. 27.

An isolated nucleic acid molecule comprising a full length cDNA sequence that is identical to a sequence encoding a N-responsive TF listed in Tables 1, 2, 3, 4, or FIG. 27 of a plant cell, or is at least 95% identical to such sequence.

A recombinant nucleic acid construct comprising in the 5 to 3' direction a promoter operable in a plant cell, and positioned downstream from the promoter and operably linked therewith a nucleic acid molecule which encodes or is complementary to a molecule which encodes a TF described herein, wherein the TF is a TF listed in Tables 1, 2, 3, 4, or FIG. 27.

A vector comprising a nucleic acid construct of as described above.

A seed or crop, or a progeny thereof of a transgenic plant as described herein.

A method for identifying transcription factors that are activated in response to a specific external stimulus comprising:

a) exposing a biological material to the external stimulus;

b) at predetermined times following exposure, generating transcriptome profiles;

c) comparing transcriptome profiles from b) to controls, wherein the controls are not exposed to the external stimulus, thereby identifying genes first expressed at each time and generating time-bin sets, wherein each time-bin set represents first genes expressed at that time;

d) generate "just-in-time" bins for each time, each bin representing exclusive sets of genes first substantially regulated by the external stimulus;

e) for each "just-in-time" bin gene set, evaluate all promoters for all genes in the gene set to identify cis-binding motifs that are over-represented;

f) for each just-in-time bin gene set, evaluate all genes for significant enrichment of Gene Ontology (GO) terms g) using machine learning algorithm and use time-series data to identify stimulus-responsive transcription factors that regulate downstream TFs or target genes.

The following example or examples are provided to further illustrate the invention and are not intended to be limiting in any way.

Figures and tables in this disclosure are labeled as Figures or Figs.

Example 1

This example describes a method to identify TFs associated with the N-uptake assimilation pathway, to prioritize, and identify TF pairs. This approach is applicable to any pathway in any biological system. In particular, this example teaches how to select TFs that regulate the genes in the N-uptake/assimilation pathway, however, the general approach below could be applied to identify TFs that regulate any pathway of interest.

Figure 8:
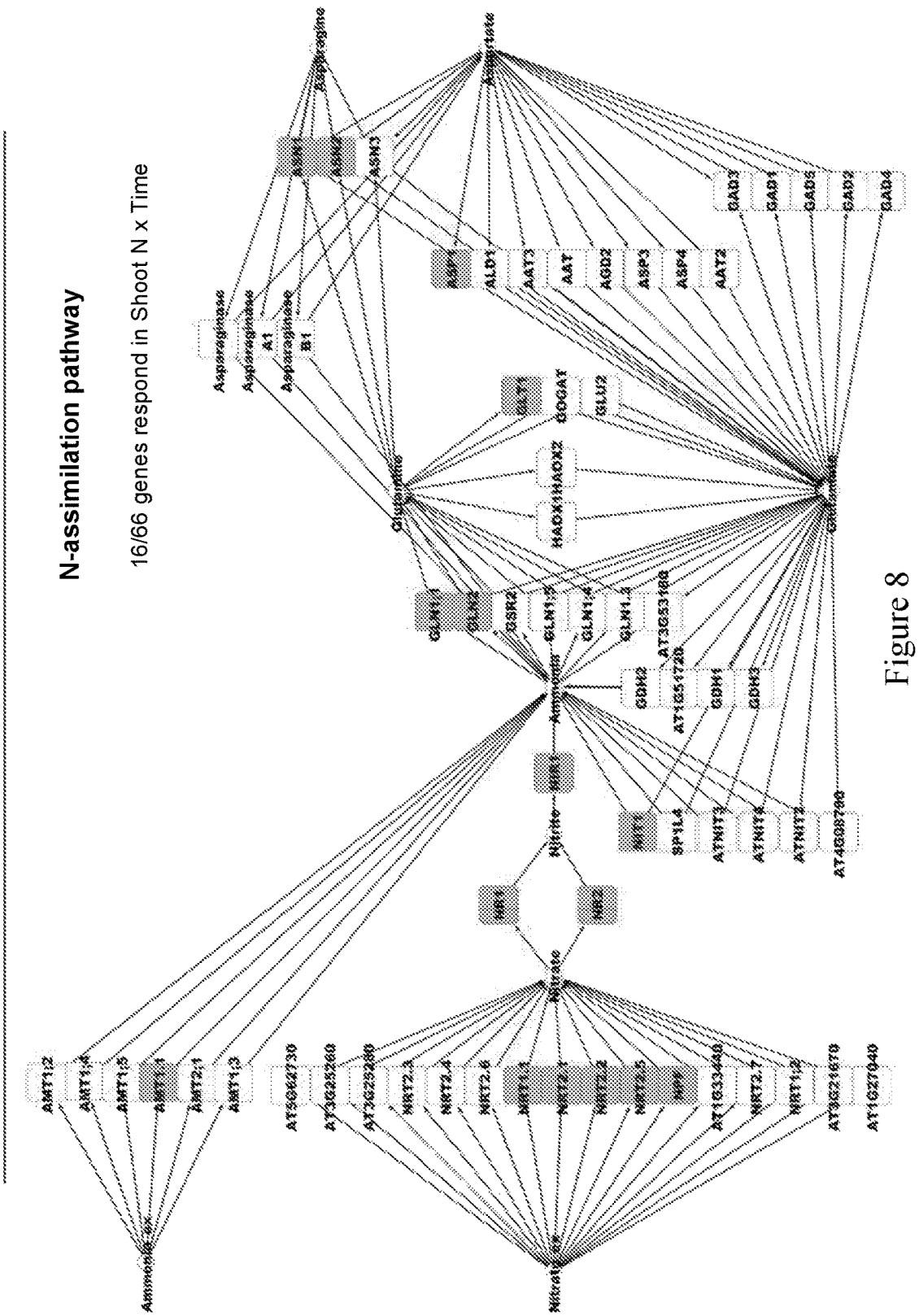
FIG. 8. All genes involved in N-uptake/assimilation pathway in the *Arabidopsis* genome. Genes shown in grey boxes are N-regulated by N×Time in shoots.

As a proof-of-principle example of the methods, the N-uptake/assimilation pathway involving CRF4 and its downstream TF2s is described. (CRF4→TF2s→N-uptake/assimilation genes). N-uptake/assimilation pathway genes are shown in FIG. 8. Genes regulated by N×TIME in green.

Step 1. Pick a TF1 Regulated Early in the N×Time-Response (e.g., CRF4—regulated by N within 5 min of treatment). The 40 TFs on left in FIG. 3*b* are ordered by the Just-in-Time analysis. This network of 40 N-responsive TFs and their predicted targets in the genome (FIG. 3*b*) are supported both by DFG Time series analysis AND by in vitro TF-target binding data (DAP-Seq). 19 TFs (bolded) (FIG. 3*b*) have a high N-specificity index (FIG. 7) in which TFs are listed by their earliest just-in-time point of N-induction. TFs may be validated in any order. For example, in one embodiment, TFs of highest priority to be validated in planta are ones that are regulated early in the N×Time course, and also have a high N-specificity index (e.g. CDF4; FIG. 7).

Figure 9:
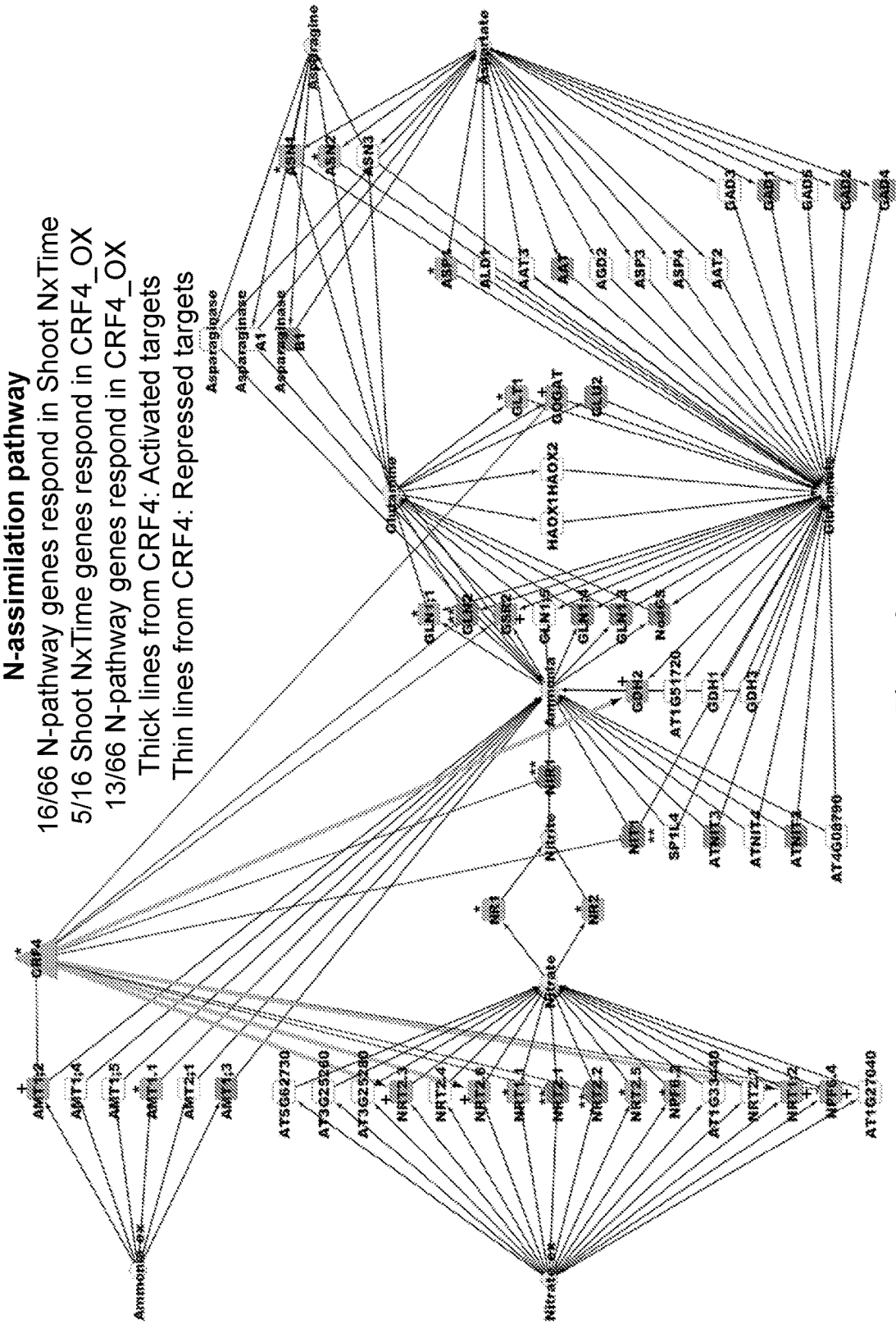
FIG. 9. N-uptake/assimilation pathway genes regulated by CRX4_OX (CRF4 inducible overexpression) in transplanta line. Triangle with *=CRF4. Solid thick line (edge) to gene target=validated induction; Solid thin line (edge) to gene target=validated repression. Nodes with **=genes regulated by CRF4_OX and responsive to N×TIME. Nodes with +=genes regulated by CRF4_OX but not regulated in N×TIME data. Nodes with *=genes regulated by N×TIME but not regulated by CRF4_OX. White nodes=genes not regulated by N×TIME data or by CRF4_OX.

Step 2. Perturb TF1 in Planta and Identify Validated Targets in Pathway of Interest:

(Working proof-of-principle example: CRF4 and N-uptake/assimilation pathway (FIG. 8). As an example, CRF4 was conditionally overexpressed in plants and its validated targets identified. Further, the list of CRF4 in planta regulated targets can be intersected with the list of N-uptake/assimilation genes (Example 2). The CRF4-regulated targets in the N-uptake/assimilation genes in shoots is visualized as a network by cytoscape (Thin lines=repressed gene target, Thick edges=induced gene target) (see FIG. 9). Next, it can be determined if CRF4 regulates these downstream targets in the N-uptake/assimilation pathway through a TF2. This can be carried out by conducting Step 3.

Step 3. Determine the TF2s Acting Downstream of TF1 (CRF4): (Working Example CRF4→16 TF2s).

Figure 10:
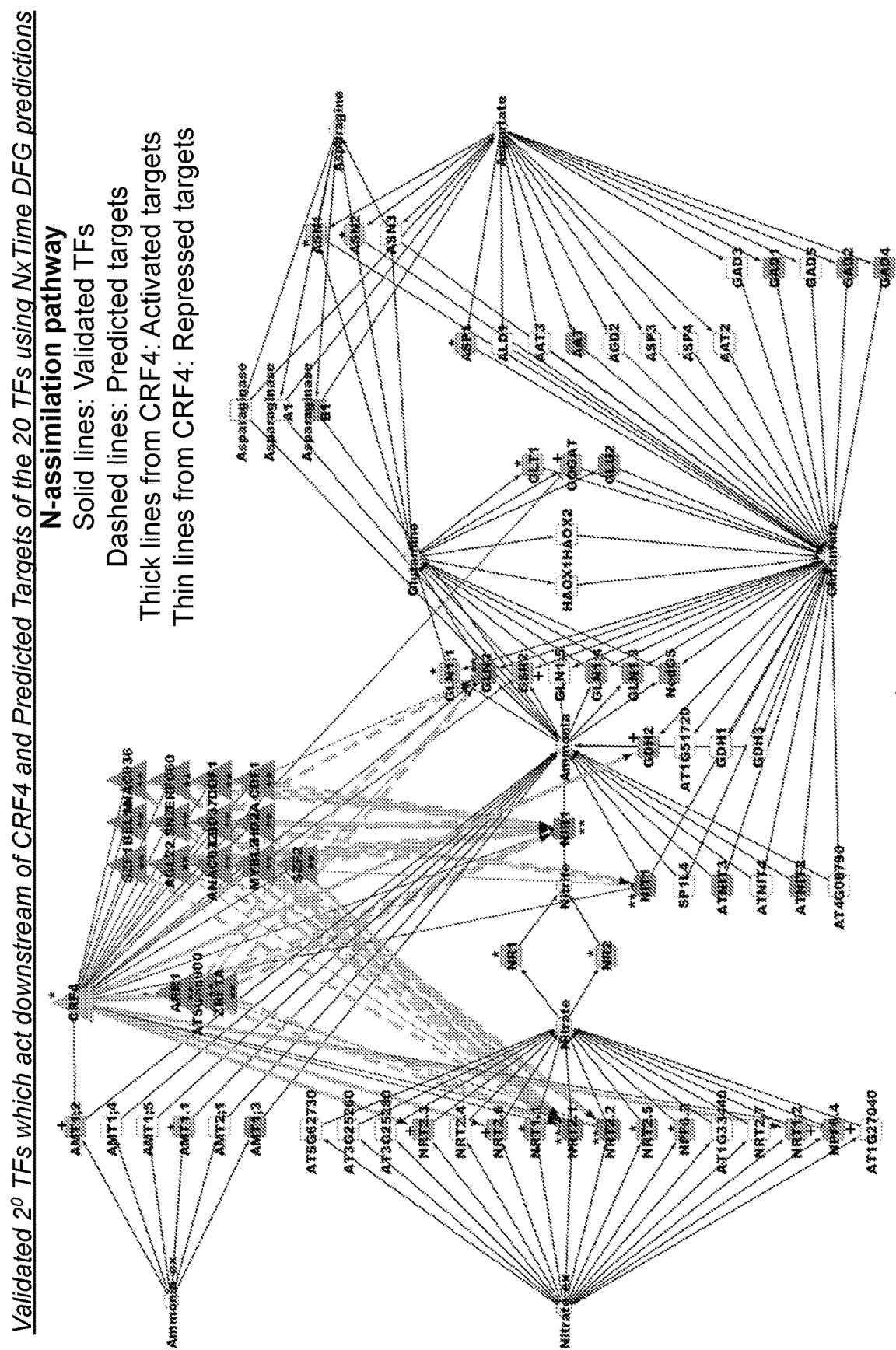
FIG. 10. Validated TF2s acting downstream of CRF4_OX (in blue triangles) to regulate genes in N-assimilation. Triangle with *=CRF4. 16 TFs targeted by CRF4 that are regulated by N×TIME=(AAR1, At5G58900, ZRF1A, SZF1, BEL10, ANAC036, AGL22, SNZ, ERF060, ANAC072, LBD37, DOF1, MYBL2, HD2A, CDF1, SZF2). Solid thick line (edge) CRF4 to gene target=validated induction; Solid thin line CRF4 (edge) to gene target=validated repression. Dashed lines TF2 to target=predicted target genes of TF2s based on TIME-series machine learning by DFG. Nodes with **=genes regulated by CRF4_OX and responsive to N×TIME. Nodes with +=genes regulated by CRF4_OX but not regulated in N×TIME data. Nodes with *=genes regulated by N×TIME but not regulated by CRF4_OX. White nodes=genes not regulated by N×TIME data or by CRF4_OX.

As an example, we used the validated in planta targets of CRF4 in Shoots or. Of the 1,209 CRF4 target genes in shoots, 67 are TFs (Example 2; FIG. 11). Of the 67 TF2s (also referred to as 2° TFs) that are validated targets of CRF4 in shoots in planta, we prioritize the 16TFs that are N-responsive in N×TIME (FIG. 11). This results in 16 TF2s that are targets of CRF4 and also N-responsive (e.g. AAR1, At5G58900, ZRF1A, SZF1, BEL10, ANAC036, AGL22, SNZ, ERF060, ANAC072, LBD37, DOF1, MYBL2, HD2A, CDF1, SZF2) (FIG. 11). Next, we predict edges between these 16 TF2 validated in planta targets of CRF4 and targets in N-uptake/assimilation pathway using time-based TF-target DFG network predictions. As shown in the working example, the TF2-target DFG predictions are indicated by dashed lines are red=repression, green=induction (FIG. 10).

Step 4: Validation of Predicted TF2 Targets in Plant Cell-Based TARGET System:

(Example: CRF4→CDF1, SNZ, ERF060→N-uptake/assimilation). As an example, we next selected 3/16 TF2s that are regulated by CRF4 in planta (CDF1, SNZ, ERF060) to functionally validate their targets in the genome using the TARGET cell-based system for rapid TF perturbation. We then combined the validated targets of CRF4 (validated in planta), with CDF1, SNZ and ERF060 (validated in plant cells) (FIG. 11) to construct a network that shows the validated regulated targets in the N-uptake/assimilation pathway genes (FIG. 12).

Step 5. Prioritizing Further TF2 Testing:

A candidate is then selected for TF2 validation. For example, we selected our next candidates for TF2 validation testing—listed in FIG. 11.

The above scheme is also illustrated in FIG. 3a.

Example 2

This example describes high-resolution time-course transcriptome study of the dynamic N-response in *Arabidopsis* to identify novel N-response genes, N-response TFs and downstream cascade from activation of the N-response TFs.

Results

Fine-Scale Time-Course of Nitrogen (N) Signal-Triggered Transcriptional Changes in *Arabidopsis*

We followed the dynamic changes in the shoot or root transcriptome from early (5 minutes) to late-term responses (up to 2 hours) following N-treatment of whole plants. The N-supply used in our study includes the inorganic-N nutrient/signals ($NO_3^-$) and ($NH_4^+$), at levels previously shown to induce an organic-N response network affecting the circadian clock. Thus, the fine-scale transcriptional response in our present study represents a response to overall N-nutrition (e.g. a mixture of inorganic and organic-N signaling).

Briefly, *Arabidopsis* seedlings grown for 14 days in low, but sufficient-N (1 mM $KNO_3$), were treated with a supply of N (20 mM $KNO_3$, 20 mM $NH_4NO_3$), as in the widely-used plant MS tissue culture media (Gutierrez et al., Proc Natl Acad Sci USA, 2008. 105(12): p. 4939-44; Murashige et al., Physiologia Plantarum, 1962. 15(3): p. 473-497), or a control supply of KCl (20 mM). Shoot and root transcriptomes were sampled at 0, 5, 10, 15, 20, 30, 45, 60, 90 and 120 min after the N-treatment (FIG. 13a). Genes responding to N-signals as a function of time (compared to controls), were identified using a linear cubic-spline model in the Limma package (Ritchie et al., Nucleic Acids Res, 2015. 43(7): p. e47) (FDR adjusted p-val<0.01, see FIG. 13 b&c). This cubic-spline model identified genes that respond to N-signals as a function of time: 2,172 N×Time genes in shoots, and 2,681 N×Time genes in roots (FIG. 1a & b). It also identified genes whose N-response was transient (e.g., NLP7, FIG. 18). The N×Time gene sets in shoot and root are organ-specific, but share 777 common genes including 54 TFs (FIG. 1c & d).

Figure 18:
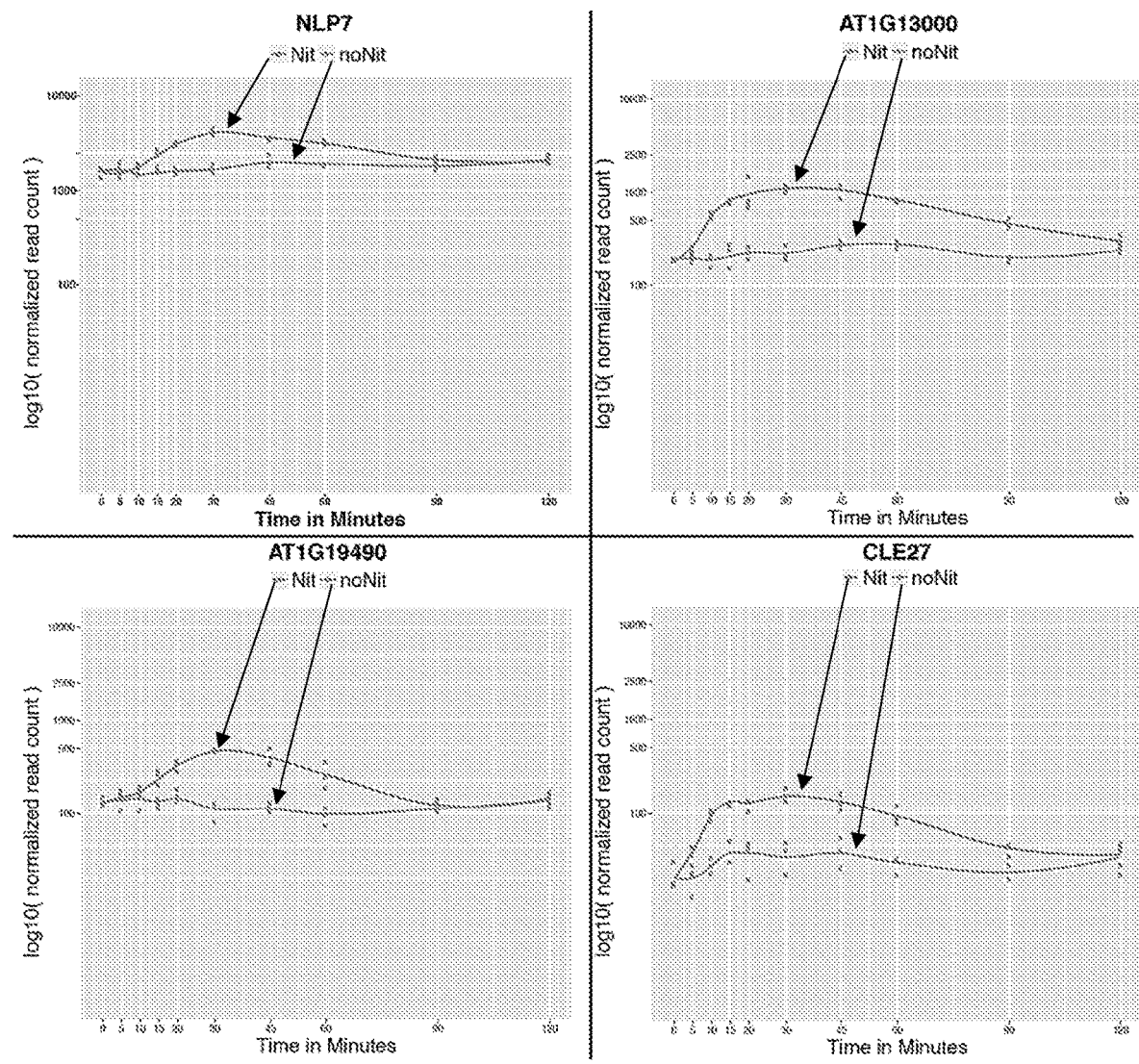
FIG. 18. Fine-scale time-series capture transient changes in N-regulated gene expression in shoots. Transient changes in N-regulated gene expression are generally missed in end-point measurements. Genes shown here to be N-regulated at earlier time-points would not be detected as N-responsive, if assayed only at 2 hours after N-signal. For example, NPL7, a main player in the N-response was not previously known to be transcriptionally regulated by N-supply at these early time-points. Genes responding to nitrogen significantly (FDR adjusted p-val <0.05) over the time-series N-response data were identified by fitting a Cubic Spline Model (df=5) to the N-treatment and Control samples, using the lmFit function in the Limma R package (Ritchie et al., Nucleic Acids Res, 2015. 43(7): p. e47).

Our analysis of the N×Time genes recovered many known N-response genes (Wang et al., Plant Physiol, 2003. 132(2): p. 556-67; Gutierrez et al., Proc Natl Acad Sci USA, 2008. 105(12): p. 4939-44; Krouk et al., Genome Biol, 2010. 11(12): p. R123; Wang et al., Plant Physiol, 2004. 136(1): p. 2512-22; Canales et al., Front Plant Sci, 2014. 5: p. 22), and also discovered 2,737 novel N-response genes. This expansion of the N-response gene set, is partially due to the increased coverage and sensitivity from RNA-seq compared to previous microarray studies of the N-response (e.g. 511 N-response genes were unrepresented on microarrays). We also captured new transient transcriptional responses to N-supply, including that for the well-known regulator NLP7 (FIG. 18). The additional coverage also captures responses to both inorganic and organic-N signals as in, but now over a time-scale. Finally, our data broadly captures dynamic N-response genes in shoots—an organ in which the N-response has been poorly studied—even though N-assimilation is tied to photosynthesis and organic N-signaling phase-shifts the circadian clock. We therefore focused our detailed analysis of dynamic transcriptome responses to nitrate and ammonium supply and the dynamic propagation of N-signaling in shoots (FIG. 1).

Globally, the temporal response to N-signaling in the shoot regulates genes in primary and secondary metabolism, global RNA processing, photosynthesis and circadian rhythm. This fine-scale time-course transcriptome data reveals the timing and order in which these biological and physiological processes are affected by N-signaling. For example, previous studies showed that the master clock gene CCA1 is N-regulated (Gutierrez et al., Proc Natl Acad Sci USA, 2008. 105(12): p. 4939-44), and our time-based study reveals that N-signaling simultaneously up-regulates the expression of the circadian TFs TOC1 and CDF1, while repressing ZTL within 30 minutes of N-signal perception. A novel insight from our time-based study, is the major effect of dynamic N-signaling on the translational machinery and RNA cycling processes.

Figure 2:
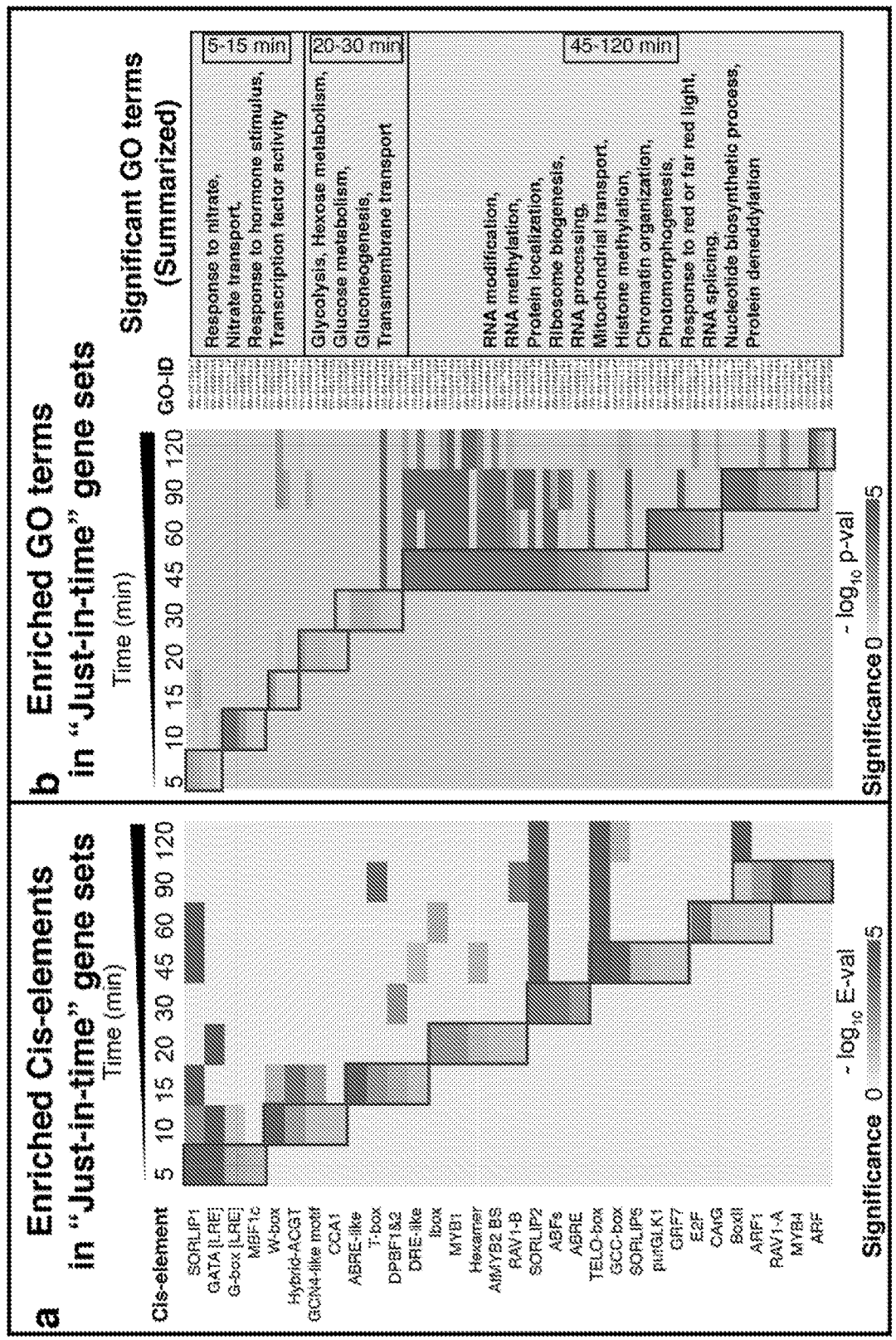
FIG. 2. "Just-in-time" analysis uncovers a temporal cascade of cis-motifs and biological processes in the dynamic N-signaling response. "Just-in-time" analysis (FIG. 13c) identified the genes that are first induced by N-signals at each time-point. a. A cascade of unique sets of cis-motifs are enriched in each of the "just-in-time" gene sets (see FIG. 1b). b. The "just-in-time" gene sets also have non-overlapping sets of GO-terms enriched in each time-point. Within 15 min of exposure to the N-signals, the primary transcriptional response is related to uptake and assimilation of nitrate. Within 30 min, energy generation processes are induced. After 45 min of N-signal perception, a large turnover of the cellular transcriptional and translational machinery occurs, leading to changes in genes affecting the chromatin status of the plant, its photosynthetic machinery and its circadian rhythm.
Figure 15:
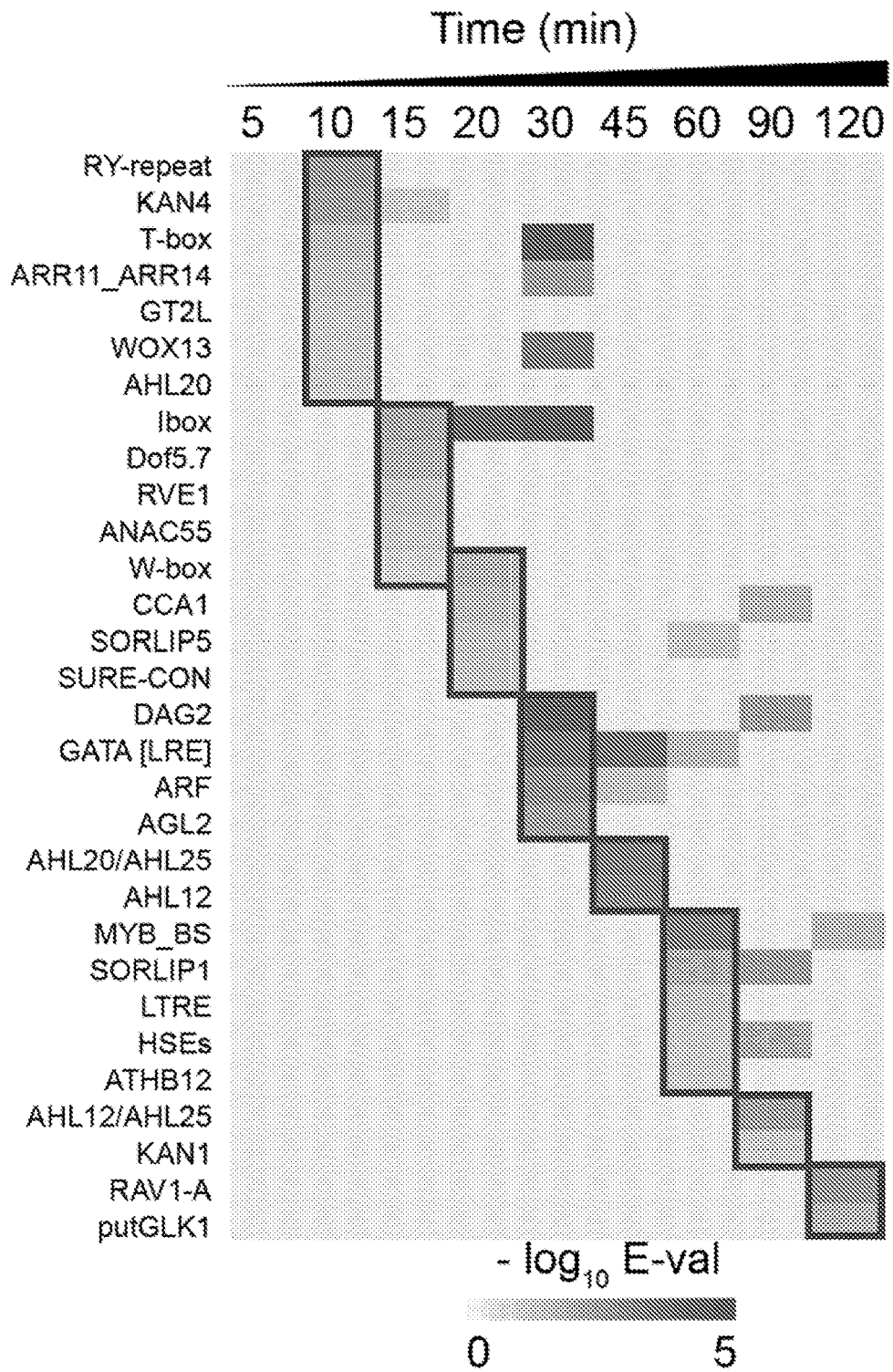
FIG. 15. Cis-motif enrichment in "just-in-time" bins in the root response. The set of cis-motifs specifically enriched in "just-in-time" analysis of the root N×Time series data is shown. Although, some cis-motifs are shared with the shoot dataset (FIG. 2a), many of the cis motifs in the root "just-in-time" gene sets are unique to the root response (eg., WOX13, Dof5.7 etc). This result implies that distinct sets of TFs are likely driving the dynamics of the N-signal response in the roots vs. the shoots.
Figure 16:
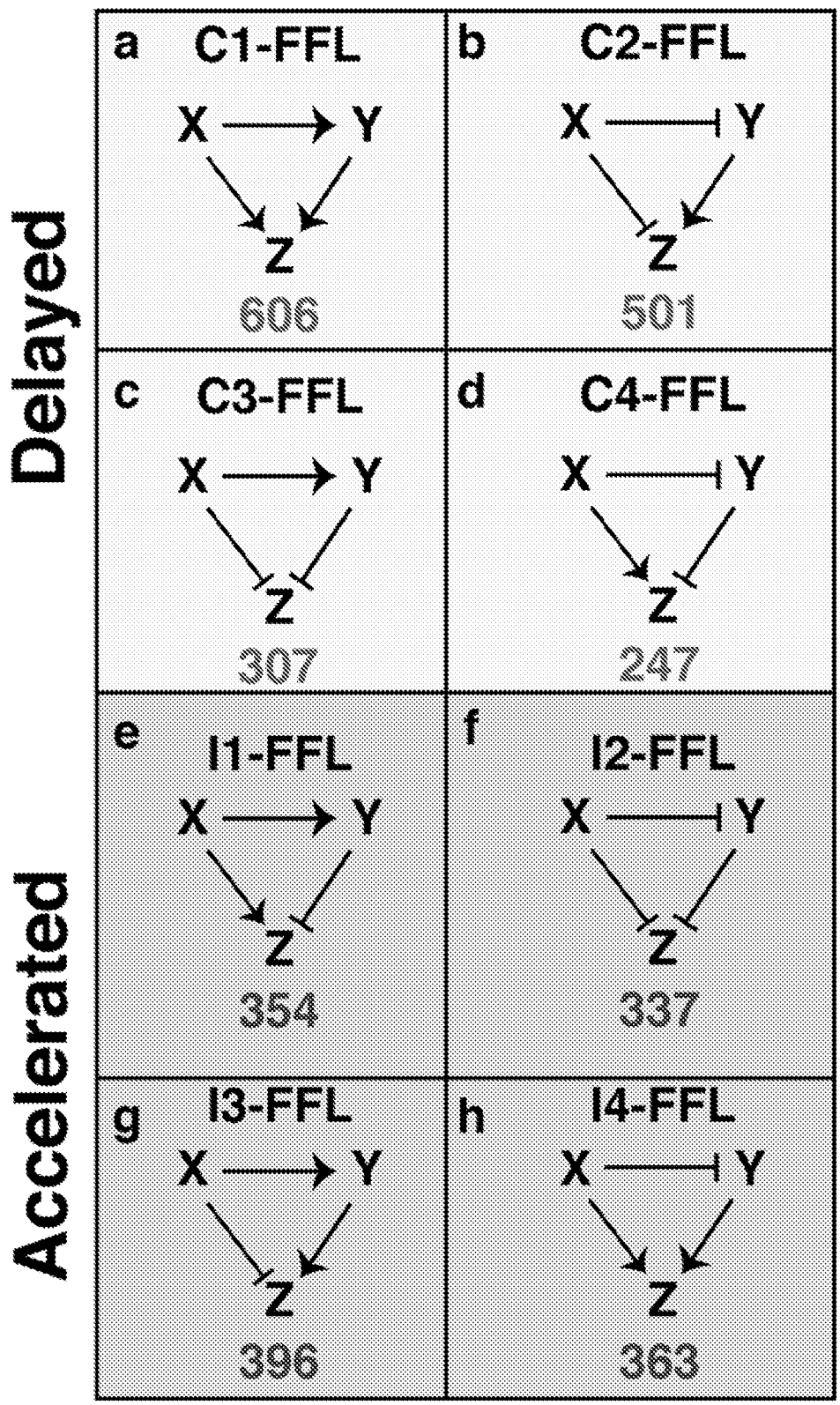
FIG. 16. Feed Forward Loops (FFLs) govern the dynamic N-signaling cascade by acting as both signal persistence detectors (a-d) and rapid response generators (e-h). The FFLs in the pruned DFG network (FIG. 3a) were identified using the "NetMatch" tool (Ferro et al., Bioinformatics, 2007. 23(7): p. 910-2) and first classified into the two types: Coherent FFLs and Incoherent FFLs based on the direction of regulation (Alon, U. Nat Rev Genet, 2007. 8(6): p. 450-61). Each FFL was then classified into the four variants within each type (Alon, U. Nat Rev Genet, 2007. 8(6): p. 450-61) (a-d) The four major variants of the Coherent-FFL motif are found in our pruned DFG network (FIG. 3a) with hundreds of instances for each variant (e-h). The four major variants of the Incoherent-FFL motif are also found in our pruned DFG network (FIG. 3a) with again hundreds of instances for each variant.
Figure 17:
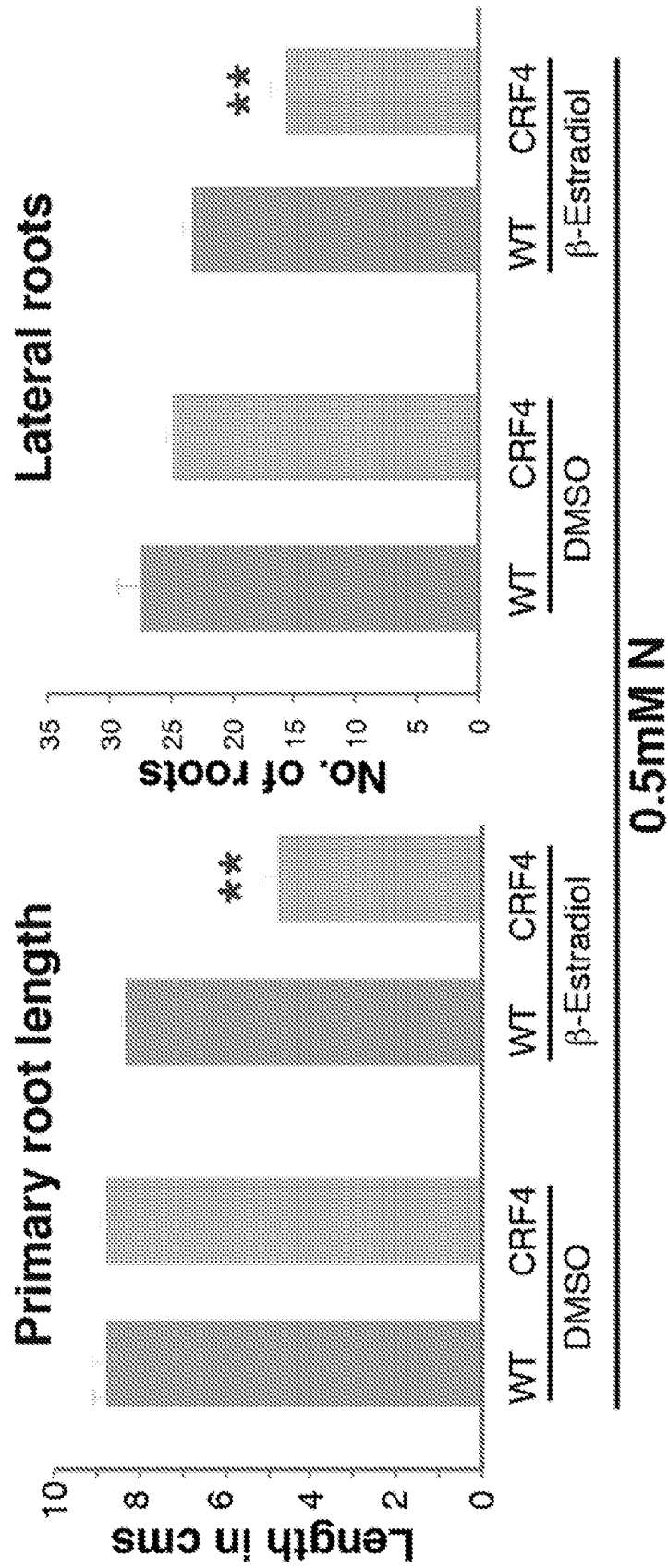
FIG. 17. Conditional over-expression of CRF4 has a negative effect on Root growth traits specifically in low-N growth conditions. a. The induction of CRF4 over-expression by β-Estradiol (Coego et al., Plant J, 2014. 77(6): p. 944-53) resulted in a reduction of primary root length and the number of lateral roots specifically under low-N (0.5 mM N, supplied as $NH_4NO_3$) conditions.

A "Just-in-Time" Analysis Uncovers a Temporal Cascade of Cis-Regulatory Elements and Biological Processes that Underlie the Dynamic Response to N-Supply To uncover the regulatory elements underlying the dynamic transcriptional response to N-supply, we implemented a "just-in-time" (JIT) analysis approach (see Methods). The "just-in-time" approach bins genes based on the first time-point at which a gene responds to N-signaling (Fold-Change (FC) >=1.5, FIG. 13c). Next, sets of genes assigned to each JIT point bin (FIG. 1b), were analyzed for overrepresented cis-regulatory motifs using a genome-wide background assuming a hyper-geometric distribution (Li et al., Plant Physiol, 2011. 156(4): p. 2124-40). This analysis uncovered a clear temporal cascade of cis-regulatory motifs significantly over-represented (e-val <0.05) in the promoters of genes first responding to the N-signal at each JIT point (FIG. 2a). To our knowledge, this is the first report of a clear temporal cascade of cis-regulatory motifs in the transcriptional response to N-supply. The transient enrichment of unique cis-motifs in specific "just-in-time" sets is particularly noticeable at the 10, 15 and 20 min time-points (FIG. 2a). Conversely, certain cis-motifs—such as SORLIP2 and TELO-box—are over-represented at consecutive "just-in-time" sets (FIG. 2a). The temporal cascade of enriched cis-regulatory motifs uncovered in the JIT gene sets, indicate that N-signaling is propagated through different sets of cis-elements and associated transcription factors in shoots (FIG. 2a) vs. roots (FIG. 15).

In addition to the enrichment of cis-regulatory motifs, we also identified over-represented GO terms (FDR adjusted p<0.01) in each JIT gene set in shoots (FIG. 2b). The early "just-in-time" gene sets (5-15 min) are significantly over-represented in genes related to N-uptake/assimilation processes. Next, the genes enriched in the intermediate (20-30 min) N-response "just-in-time" sets are related to energy generation processes. Finally, in the later "just-in-time" gene sets (>=45 min), N-signaling regulates genes in metabolic and developmental processes (FIG. 2b).

Overall, the temporal cascade of enriched cis-regulatory elements uncovered in the "just-in-time" analysis, implicates a cascade of associated TFs regulating largely non-overlapping sets of genes at consecutive time-points in the N-signaling cascade. To identify and validate such implied TF-target associations, we employed a time-based machine learning approach and experimental validation studies described below.

Inferring a Time-Derived High-Confidence GRN Driving the Temporal N-Response in Shoots.

To complement the temporal cis-regulatory element cascade we uncovered in the N-signaling response, we inferred a GRN of TF-target relationships as a function of time. Because causality moves forward in time, fine-scale time-series experiments are a valuable resource to infer GRN network models that can predict TF-target relationships. To do this, we used a time-based machine-learning method called Dynamic Factor Graphs (DFG) (Mirowski et al., Machine Learning and Knowledge Discovery in Databases: European Conference, ECML PKDD 2009, Bled, Slovenia, Sep. 7-11, 2009, Proceedings, Part II, W. Buntine, et al., Editors. 2009, Springer Berlin Heidelberg: Berlin, Heidelberg. p. 128-143.). We thus implemented the time-based DFG network inference method, with rigorous hyper-parameterization steps that test predictions based on out-of-sample data (see Methods), to infer the influence of every TF on every gene in the NxTime gene set (FIG. 3a). The resulting time-based DFG network inferred the influence of the 172 N-responsive TFs on the 2,172 NxTime response genes in the shoot. To overcome a major challenge in de novo network inference—the high false positive (FP) rate—we employed a "network pruning" approach that co-maximizes Precision and Recall to control the FP rate (Stolovitzky et al., Ann N Y Acad Sci, 2009. 1158: p. 159-95). To implement this "network pruning" step, we first validated the true genome-wide targets of the "earliest" TF hub CRF4 in the GRN (JIT: 5 min, FIG. 3b) using a transient cell-based TF perturbation assay (TARGET (Bargmann et al., Mol Plant, 2013. 6(3): p. 978-80)), and also using an inducible over-expression transplanta line (CRF4-OX) (Coego et al., Plant J, 2014. 77(6): p. 944-53). From the validated genome-wide targets of CRF4 (FIG. 4a), we identified two downstream TF targets (SNZ and CDF1) that were N-responsive "early" and "late" in the "just-in-time" analysis (SNZ: 10 min, CDF1: 45 min). We next validated the genome-wide targets of SNZ and CDF1 in shoot cells using the cell-based TARGET system (Bargmann et al., Mol Plant, 2013. 6(3): p. 978-80), incorporated herein by reference (FIG. 4a).

The TF-target validation data for CRF4, SNZ and CDF1 (FIG. 4a), was used to compute a network performance metric of the DFG-inferred TF-target predictions called Area Under Precision-Recall (AUPR) curve (Stolovitzky et al., Ann N Y Acad Sci, 2009. 1158: p. 159-95) (FIG. 4c). This AUPR analysis was performed to; i. establish that the DFG-inferred GRN is significantly better than a random network of the NxTime response genes (FIG. 4b & c); and ii. identify the network edge score threshold that maximizes Precision of DFG-inferred GRN (FIG. 4c) (see Methods). To do this, we compared the TF-target predictions from the DFG-inferred network to a random ranking of TF-target edges, by computing 1,000 random networks of equal size, and computed the AUPR values for each of the random networks (FIG. 4b). DFG's AUPR value of 0.24 is significantly better (p-val <0.001) than the mean AUPR of 0.14 for the random networks (FIG. 4b & c). Next, the resulting Precision-Recall (PR) curve (Stolovitzky et al., Ann N Y Acad Sci, 2009. 1158: p. 159-95) (FIG. 4c) was used to identify the threshold at which to "prune" the DFG-inferred network. To identify a high-confidence DFG network, a point in the PR curve is chosen such that it maximizes precision before the curve flattens. From DFG's PR curve (FIG. 4c), we chose a precision of 0.345, which is the last precision peak before the AUPR curve flattens. The corresponding edge in the ranked DFG-inferred GRN has a score of 0.955. Therefore, only edges with score >=0.955 were retained in the DFG-inferred network (FIG. 3a).

The resultant "pruned" DFG-inferred GRN network with a precision of 0.345 (i.e., one in three predicted edges are likely to be true), includes 608 genes connected by 8,152 edges (FIG. 3a). This high-confidence DFG-inferred GRN now provides a wealth of regulatory information in the N-signaling network. For example, this "pruned" DFG-inferred GRN predicts that 245 genes in the NxTime set are regulated by the three novel transcription factors (CRF4, SNZ and CDF1), and 85 of these DFG-predicted edges were validated in our TF perturbation studies. These DFG-predicted and experimentally validated targets for CRF4, SNZ and CDF1 include five key genes in the N-uptake/assimilation pathway (NRT1.1, NR1 & NR2, NIR, GLN1.1) (FIG. 5, edges denoted by *), ten genes involved in transcriptional/translational machinery, as well as genes involved in the circadian clock (e.g. TIC).

Independent TF-Target Binding Data Supports Predicted Edges in the N-Signaling GRN.

The "pruned" DFG network, identified as hubs (i.e., influential TFs) multiple known/validated regulators of N-signaling (e.g. TGA1/4, NLP7/8, NAC4, HRS1, LBD37/38/39), as well as 146 potential novel regulators of N-signaling, including ones (CRF4, SNZ and CDF1) validated herein to be highly N-specific and to regulate a significant number of genes in the NxTime GRN (FIG. 4a). To build additional support for these DFG-predicted edges in the GRN, we overlaid an independent source of TF-target binding data (DAP-Seq). Briefly, in a recent study, O'Malley et al., identified the genome-wide binding sites for 529 TFs in *Arabidopsis* through in vitro assays of TF binding to genomic DNA (O'Malley et al., Cell, 2016. 166(6): p. 1598). We used this extensive TF-DNA binding information to derive additional edge support for the DFG time-inferred N-signaling GRN network as follows: A TF-target edge in our time-driven DFG-inferred GRN, is supported by the DAP-Seq dataset, only if that TF is shown to bind the promoter of its predicted target in the DAP-Seq assay (FIG. 3b. The actual TF binding data from the DAP-Seq datasets (Ecker, J. R. 2017; Available from: neomorph.salk.edu/dap_web/pages/index.php were used to determine TF-target binding, we did not use the in silico DAP-seq derived motif information for edge support. Importantly, our DFG-network inferred from time-series data now provides the direction of regulation for each TF on its targets in the N-response network (FIG. 3b), which is unavailable from TF-target binding data alone. While, the TF binding data supports many of the edges in our "pruned" DFG-inferred GRN, this analysis is limited to the set of TFs with available DAP-Seq TF-target binding data (TFs on left in FIG. 3b). Therefore, given our rigorous network "pruning" procedure to obtain a precision of 0.345 (FIG. 3a), we use the complete "pruned" DFG network of 155 TFs (608 genes) and 8152 edges (FIG. 3a) for subsequent analysis.

Assigning a "N-Specificity" Index to TFs in the GRN for the N-Response. Our time-derived GRN covers a broad transcriptional response to N-signals shoots, and alters the expression of ~6% of all *Arabidopsis* genes within two hours of N-supply. This N-signaling cascade affects genes involved in numerous cellular and developmental processes (FIG. 2), and acts through a large number of TFs (FIGS. 1d & 3a). To identify TFs that play a highly significant and specific role in N-signaling in our GRN, we computed a "N-specificity" index for each TF in the N-signal responsive gene set (FIG. 7). Briefly, for each N-regulated TF, we tested if the proportion of its genome-wide targets was significantly overrepresented in the N-responsive time-dependent gene set (2,172 genes) (see Methods), compared to the proportion of all its bound targets in the genome (based on TF-DNA binding DAP-Seq data). A subset of the N-responsive TFs with a high "N-specificity" score (p-val <0.05). These "N-specific" TFs include ones previously validated to regulate the N-response, such as NLP7, TGA1/4, NAC4, and also identify 15 novel TF regulators highly specific to the dynamic N-signal response (FIG. 3b (Left side) TFs in BOLD=high N-specificity index). We note that the N-specificity calculation in Table 1 and FIG. 3b is limited to TFs for with TF-Target binding data from DAP-seq, including CRF4. Later, we show that the concept of N-specificity index can be applied to any TF for which there are validated genome-wide targets, including ones not in the DAP-Seq dataset (e.g. SNZ and CDF1) (FIG. 4a).

A Temporal Cascade of Feed-Forward Loops (FFLs) in Dynamic N-Signaling.

Figure 5:
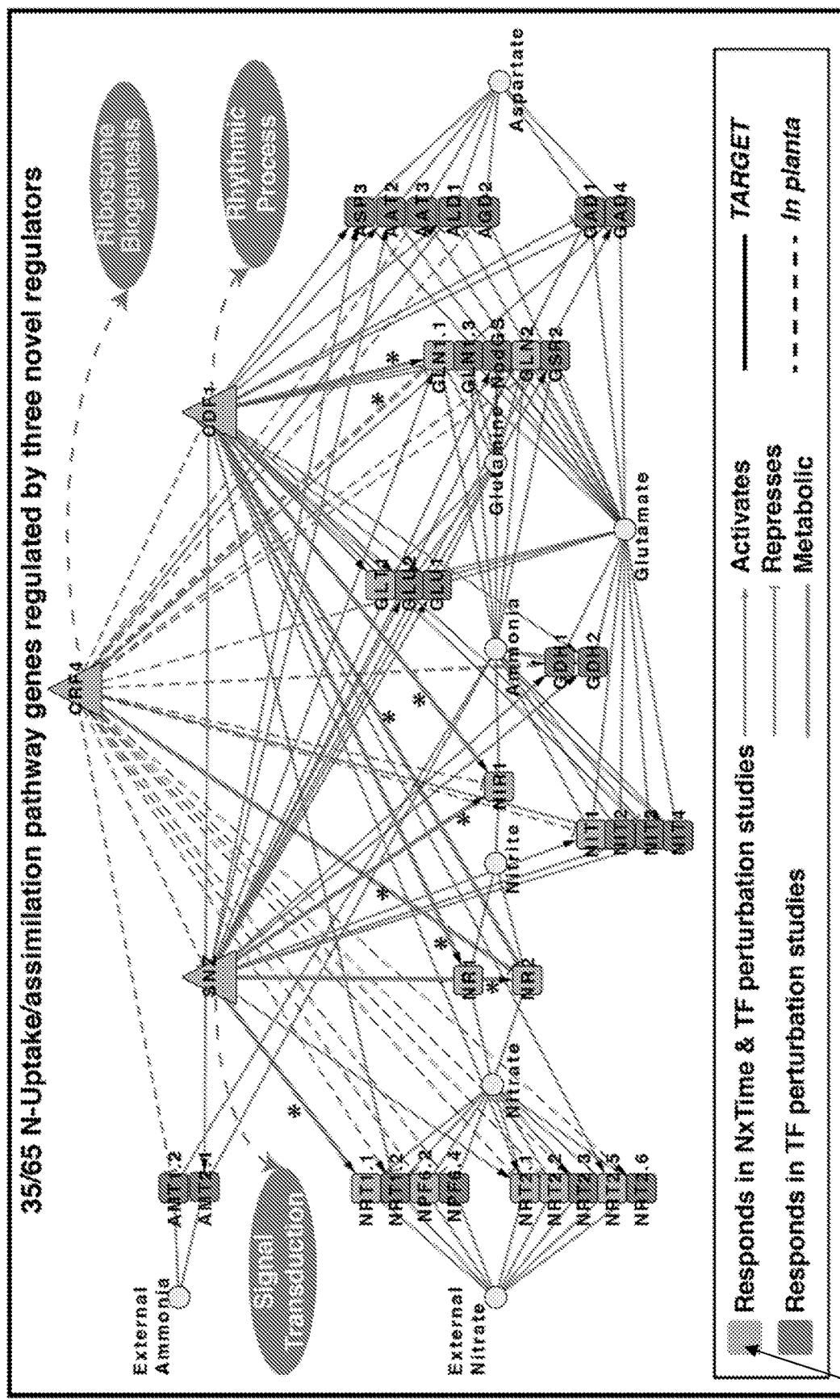
FIG. 5. Three novel TF regulators (CRF4, SNZ, CDF1) of genes in the N-uptake/assimilation pathway. Nitrogen uptake and initial assimilation is governed by a set of 65 genes. The three novel regulators of N-uptake/assimilation (CRF4, SNZ and CDF1) discovered in the GRN are validated to regulate the expression of 35/65 or 53% of these N-uptake/assimilation genes as determined by TF perturbation studies. 12 N-uptake/assimilation genes respond to the N-supply in the time course (FIG. 1a) and are regulated by one or more of these three TFs (Nodes in green). In addition, the expression level of 23 additional N-uptake/assimilation genes was perturbed by over-expressing one or more of CRF4, SNZ and/or CDF1. CRF4 was validated to represses multiple steps in the N-uptake/assimilation pathway and the two downstream TFs SNZ and CDF1 in planta. Plant cell-based over-expression assays showed that SNZ and CDF1 induce the expression of many N-uptake/assimilation pathway genes. Thus, CRF4 repression of N-uptake/assimilation pathway genes is at least partially due to repression of the TF activators of the pathway, SNZ and CDF1. Edges that are both predicted by DFG (with a precision of 0.345) and validated by TF perturbation are shown by (*) and thicker edge width. Grey circles indicate other cellular processes validated to be regulated by these three TFs (FIG. 4a).

Our high-confidence DFG-inferred GRN now provides a genome-wide view of potential Feed Forward Loops (FFLs) involved in dynamic N-signaling in plants. Briefly, a FFL describes the regulation of a target by a primary and a secondary TF, such that the primary TF regulates both the secondary TF and the final target (Milo et al., Science, 2002. 298(5594): p. 824-7; Alon, U., Nat Rev Genet, 2007. 8(6): p. 450-61). Using a motif search algorithm called NetMatch (Ferro et al., Bioinformatics, 2007. 23(7): p. 910-2), we identified 3,111 FFLs in the "pruned" DFG-inferred GRN for dynamic N-signaling in shoots, and 171 FFLs in the TF-only subnetwork. All eight variants of the "classic" FFL (Alon, U., Nat Rev Genet, 2007. 8(6): p. 450-61) exist in our time-dependent N-regulatory GRN of shoots, based on induction or repression edges, between the two transcription factors and the target, as assayed genome-wide (Supp. FIG. 5). The two main FFL classes (each includes four variants), in our shoot data are the Coherent Feed Forward Loop (C-FFL) (1661 loops; FIG. 16a-d)), and the Incoherent Feed Forward Loop (I-FFL) (1450 loops) (FIG. 16, e-h), which are suggested to generate distinct regulatory regimes (Mangan et al., Proc Natl Acad Sci USA, 2003. 100(21): p. 11980-5.). In response to a signal/stimulus, C-FFLs act a persistence detector (Alon, U., Nat Rev Genet, 2007. 8(6): p. 450-61)—activating the target only after the initial N-signal persists for a period-, while the I-FFLs act as a response accelerator (Alon, U., Nat Rev Genet, 2007. 8(6): p. 450-61)—producing a rapid response of the target gene to the initial N-signal-, followed by a dampening. While these FFLs are derived from our pruned, high-confidence DFG-inferred GRN, the regulatory dynamics of individual FFLs and their role in N-signal transduction can be validated. One of the TFs validated in our study—CDF1—is predicted to initiate five FFLs by repressing three intermediate TFs SZF1, RAP2.12 and KNAT3. Of these three FFL TFs, SZF1 (AT3G55980) and KNAT3 (AT5G25220) were found to be validated targets of CDF1, as they were indeed repressed by over-expressing CDF1 in our cell-based TARGET assay.

Three Novel TF Hubs—CRF4, SNZ and CDF1—in N-Signaling and N-Use in Planta.

To assess the significance of our DFG-inferred network to N-signaling/use in planta, we prioritized CRF4 for initial in planta validation studies as it is: i) an "early" N-responder (5 min JIT) (FIG. 3b); ii) a novel, early hub in the DFG-inferred GRN (FIG. 3b) with a high N-specificity index (Table 1). We also experimentally validated two true TF targets of CRF4 that react "early" (SNZ, 10 min JIT) and "late" (CDF1, 45 min JIT) in the temporal N-signaling cascade (FIG. 3a). These validated TF targets of CRF4 were predicted by DFG inference, but were "pruned" as their edge score was below the 0.955 score threshold, and are thus False Negatives. We determined the genome-wide targets of all three TFs (CRF4, SNZ, CDF1) using a cell-based TF perturbation system called TARGET, as well as in planta, using an inducible TF overexpression line for CRF4 (CRF4-OX). These TF-target validation data (FIG. 4a), show that the validated genome-wide targets of CRF4, SNZ and CDF1 are: i. significantly over-represented in the N×Time gene set, ii. include 54% of the genes in the N-uptake/assimilation pathway, which iii. affects N-uptake and use in planta, as detailed below.

i. Roles of CRF4, SNZ and CDF1 in Dynamic N-Signaling:

The 2,496 validated genome-wide targets of CRF4 (FIG. 4a), are relevant to the dynamic N-response as they are; i. significantly enriched in N×Time gene sets, ii. support a high N-specificity index, and iii. are enriched in GO-terms related to "Nitrate assimilation" and "Ribosome biogenesis" (FIG. 4a), among others. Likewise, the validated targets of the TFs acting downstream of CRF4—SNZ (1,753 targets, FIG. 4a) and CDF1 (3,193 targets, FIG. 4a) comprise: i. highly significant overlaps with the N×Time gene set (FIG. 4a), ii. support a high N-specificity index (FIG. 4a), and iii. are significantly enriched in GO-terms related to "Nitrogen assimilation/metabolism" and "rhythmic processes" (for CDF1) (FIG. 4a).

ii. Roles of CRF4, SNZ and CDF1 in Regulation of N-Uptake/Assimilation Pathway Genes:

The validated genome-wide targets of CRF4, SNZ and CDF1 (FIG. 4a), show that 54% of genes in the N-uptake/assimilation pathway (35/65) are regulated by these three TFs (FIG. 5). This includes 75% (12/16) of the N-responsive genes in the N-uptake/assimilation pathway, and 23 additional pathway genes that did not respond within 2 hours of the N-supply (FIG. 5). These experimentally validated regulatory edges establish the extensive role of CRF4, SNZ and CDF1 in the regulation of genes in the N-uptake/assimilation pathway. Overall, the role of CRF4 is to repress multiple steps in the N-uptake and assimilation steps (FIG. 5). Conversely, SNZ acts primarily as an inducer of N-uptake/assimilation, while CDF1 induces or represses various steps of the N-pathway (FIG. 5). As validated in planta, at least part of the repression of the N-uptake/assimilation pathway by CRF4 likely acts through CRF4 repression of the activators SNZ and CDF1. The validated targets of CRF4, SNZ, CDF1 in the N-uptake/assimilation pathway include nine edges predicted by our "pruned" high-confidence GRN (FIG. 5, edges with asterisks). This validation outcome reflects a crucial feature of our "pruned" high-confidence N-signaling GRN—high precision, but low recall (FIG. 4c). Thus, our high-confidence GRN is likely to underestimate the influence of a given TF on the network. This effect is clearly demonstrated by the additional regulatory edges in the N-uptake/assimilation pathway discovered experimentally by TF perturbation of CRF4, SNZ and CDF1 (FIG. 5, e.g. edges with no asterisk).

iii. Role of CRF4 in Regulating N-Uptake and N-Use in Planta.

Our "high-confidence" GRN and validation studies of CRF4, SNZ & CDF1, link CRF4 directly or indirectly to the regulation of 21 genes in the N-uptake/assimilation pathway, including seven genes involved in nitrate-uptake (i.e., nitrate transporters) (FIG. 5). Specifically, CRF4 represses SNZ and CDF1, which are inducers of the main high-affinity nitrate transporter gene, NRT2.1 (FIG. 6a). Under low-N conditions (0.5 mM N) the high-affinity N-transporter, NRT2.1, is the major functional nitrate-uptake system. We thus tested whether CRF4 repression of NRT2.1 gene expression in CRF4-OX as depicted in FIG. 6c, had an effect on high-affinity nitrate-uptake in planta (FIG. 6b). To do this, we measured the rate of nitrate-uptake using a $^{15}NO_3^-$ tracer under low-N conditions (0.5 mM N) in an inducible CRF4-OX line, in the nrt2.1 mutant, and in wild-type Arabidopsis. A 2-way ANOVA test, followed by Tukey HSD analysis (Methods) showed that $^{15}NO_3$-uptake rate was significantly reduced in the induced CRF4-OX lines, at levels comparable to the nrt2.1 mutant (FIG. 6b). By contrast, nitrate uptake rates were normal in the CRF4-OX controls (no β-estradiol induction) which were comparable to wild-type (FIG. 6b).

Figure 6:
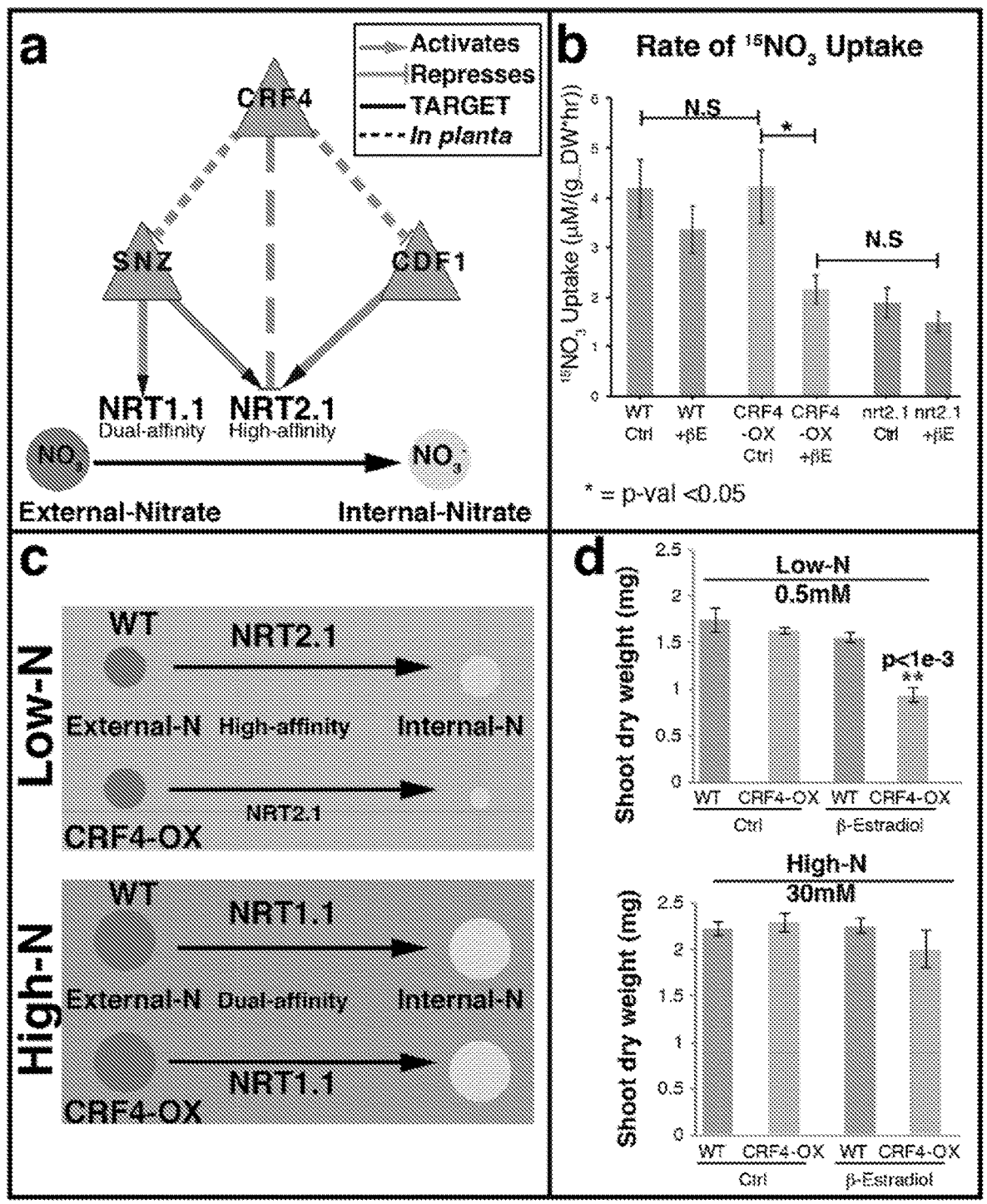
FIG. 6. CRF4 repression of nitrate transporter (NRT2.1) affects high-affinity nitrate uptake and biomass in planta. a. The TF perturbations showed that NRT2.1 is repressed by CRF4 in planta and induced by SNZ and CDF1 in TARGET cell-based assays. CRF4 is also validated to repress SNZ and CDF1 in planta. b. CRF4 over-expression in low-N (0.5 mM N) conditions significantly reduces the rate of nitrate uptake in seedlings, as measured by $^{15}NO_3$ uptake assays (Tukey test, see Methods). c. Under low-N conditions (0.5 mM N) the high-affinity N-transporter, NRT2.1, is the major functional nitrate-uptake system. Conditional CRF4 over-expression represses NRT2.1 mRNA levels resulting in lower levels of nitrate uptake under low-N conditions. By contrast, under high-N (30 mM N) conditions, NRT1.1 is the major nitrate-uptake system and CRF4 over-expression does not affect nitrate-uptake rate. d. Sustained induction of CRF4 in plants grown under low-N conditions (0.5 mM N) results in significantly (Tukey test) lower shoot biomass. Again, this growth retardation is specific to low N is and is not observed in high-N conditions (30 mM).

Thus, these results show that conditional CRF4 overexpression represses expression of levels of mRNA for the high affinity nitrate transporter (NRT2.1) (FIG. 6c), and results in lower levels of nitrate-uptake at low-N (FIG. 6b). Moreover, long-term effects of CRF4 repression of NRT2.1 expression and nitrate-uptake, result in significant reductions in shoot biomass (p<1e-5) (FIG. 6d) and root primary root length and number of lateral roots (Supp. FIG. 6), in induced CRF4-OX (β-estradiol), specifically under low-N conditions (e.g. affected in high affinity nitrate-uptake). By contrast, the effect of CRF4-OX on N-uptake is not affected under high-N conditions, where N-uptake occurs primarily through low-affinity activity of NRT1.1, which is not repressed by CRF4-OX (FIG. 6c & d). These phenotypic results validate the important role of CRF4—potentially acting through SNZ and CDF1—plays in mediating plant responses to a N-signal and its effects on nitrate-uptake and N-use under N-limiting vs. -replete conditions.

Discussion

Figure 4:
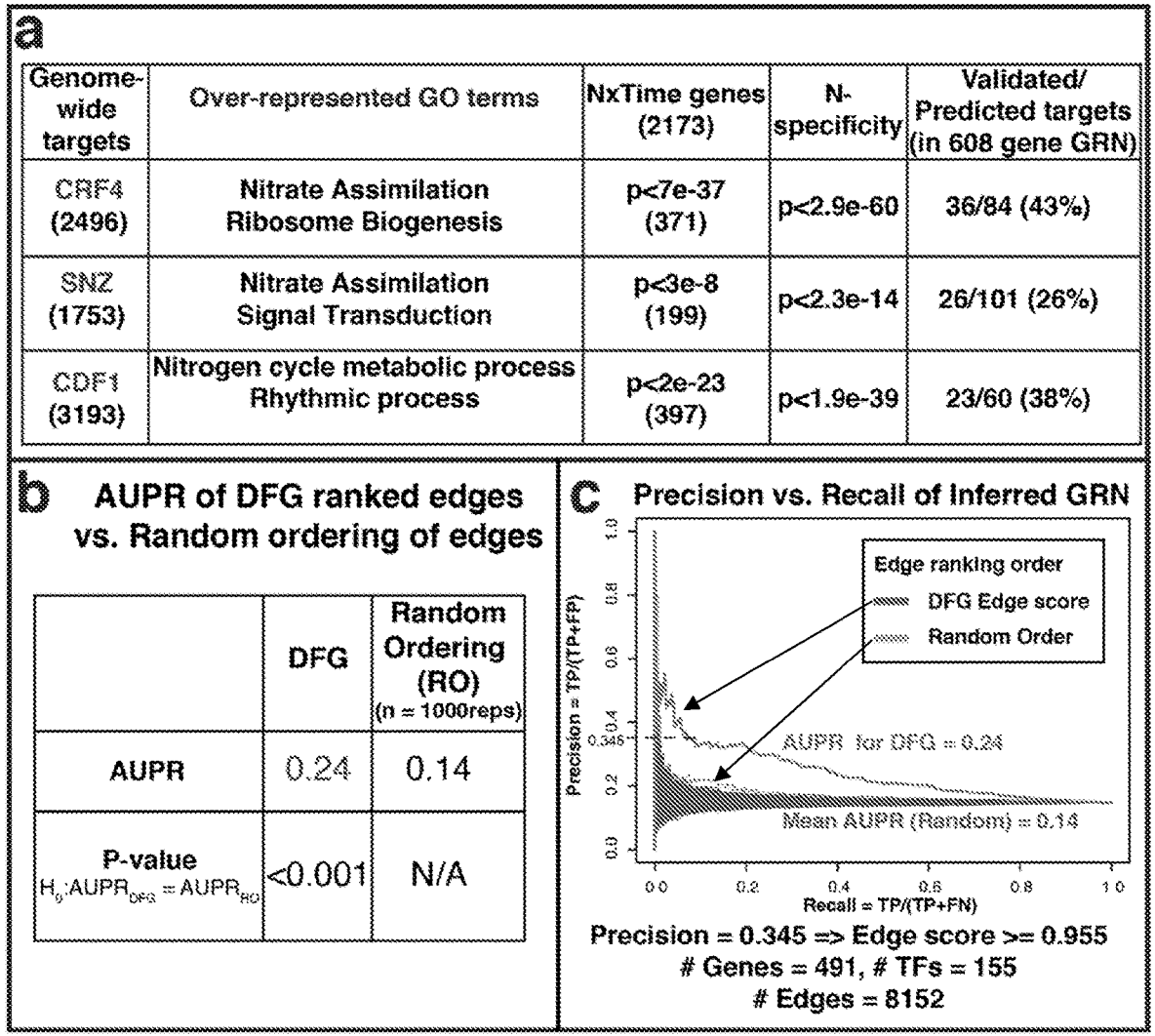
FIG. 4. Time-inferred GRN for dynamic N-response "pruned" with validated genome-wide TF target data. a. Genome-wide targets of CRF4, SNZ and CDF1 were validated by constitutive and/or transient over-expression in plants and/or plant cells. SNZ and CDF1 are validated TFs acting downstream of CRF4 in planta, based on CRF4 conditional overexpression. b. Genome-wide targets of CRF4, SNZ and CDF1 were compared to the ranked DFG edges to calculate Precision (True positives/(True+False positives)) and Recall (True positives/(True positive+False negative)). Precision-Recall (PR) curves show that the DFG ranking of edges scores is significantly better than random order (p<0.001) and the Area under PR curve (AUPR) is higher for DFG compared to random ordering (n=1000). c. From the AUPR curve, the highest precision (Precision=0.345, corresponding edge score=0.955) before the curve flattens was chosen as threshold to "prune" network predictions to include only high-confidence targets.

Nitrogen (N)—a key nutrient/signal—regulates dynamic plant processes, including circadian rhythm and root-foraging—but temporal insights into the underlying mechanisms are lacking. In this study, we used time to uncover a temporal gene regulatory network whose components are validated to mediate dynamic N-signaling and N-use in plants. We used time-series transcriptome data to uncover a temporal cascade of cis-elements underlying dynamic N-signaling, using a "just-in-time" analysis of N-response time-series transcriptome data (FIG. 2a). This time-series N-response dataset was also used to learn the response cascade and infer the gene regulatory network (GRN) of 172 transcription factors (TFs), and to calculate a TF "N-specificity" index. The inferred GRN was refined using experimental TF perturbation studies for three TFs (CRF4, CDF1 and SNZ) that the GRN identified as novel regulators of N-uptake/assimilation (FIGS. 4-5). Moreover, these GRN predictions were validated and also had significance to nitrogen use in planta. Specifically, conditional overexpression of the novel regulator CRF4 in planta, represses the high-affinity nitrate transporter (NRT2.1), reducing nitrate uptake and biomass specifically under low-N (FIG. 6). This high-confidence GRN now provides the temporal logic for >150 candidate TFs whose perturbations may serve to improve N-use efficiency in plants. Moreover, the time-based approach we present can be generally applied to uncover the temporal "transcriptional logic" for any biological response system.

Dynamic N-Signaling Alters the Global Transcriptional Profile and Affects Genes Involved in Primary and Secondary Metabolism and Master Regulators of Circadian Rhythm.

Our time-series studies of the genome-wide responses to N-signaling uncovered discrete waves of transcriptional responses in shoots and roots (FIG. 1). The initial transcriptional response in <30 minutes of N-supply, is enriched in genes involved in the N-uptake, and the generation of energy required for N-reduction/assimilation in shoots (FIG. 2b). Later phases involve changes in the transcriptional and translational machinery, methylation changes and circadian rhythm (FIG. 2b). For example, the N-signal transcriptional cascade results in the induction of TFs in the circadian clock including TOC1 and CDF1, and the repression of ZTL between 20-45 minutes after the N-signal. These findings confirm and extend previous studies about the role of N-signaling as an input that regulates the circadian clock in plants (Gutierrez et al., Proc Natl Acad Sci USA, 2008. 105(12): p. 4939-44). A novel discovery from our time-based study is the identification of a robust induction of the cellular transcriptional and translational machinery within 30-45 minutes after the initial N-signal (FIG. 2b, FIG. 14). Importantly, the GRN inferred from the N×Time-series dataset enabled us to predict and validate that CRF4—the earliest responding TF in the GRN—regulates multiple members of this transcriptional and translational machinery in response to N-supply.

A Time-Based Causal Regulatory Network Identifies Novel Regulators of the Dynamic N-Response and their Predicted Interactions.

A crucial aspect of our temporal N-signal profile and GRN, is that it now places known regulators of the N-signal (e.g. NLP7, HRS1, TGA1/4, LBD37/38/39 and NAC4) in the context of the time and order in which these TFs respond to an N-signal, and importantly, how they likely function in a regulatory cascade (FIG. 3b). In addition to these known TF regulators, our analysis identified a set of 15 novel TFs that are highly N-specific to the N-response network (FIG. 7), which we can now place in temporal context with the known N-response TFs (FIG. 3b). As proof-of-principle, we experimentally validated the regulatory role of a set of three novel TFs that respond between 5-45 minutes of N-treatment (CRF4, SNZ and CDF1) by way of TF perturbation studies in cells and in planta (FIG. 4-6). These and phenotypic studies of nitrogen use (FIGS. 5 & 6) validate the important role of CRF4—potentially acting through SNZ and CDF1—plays in mediating plant responses to a N-signal and its effects on nitrogen-uptake and -use under N-limiting vs. -replete conditions.

More broadly, our high-confidence GRN predicts interactions of 155 TFs and their ~600 targets within the N×Time gene set, and identifies the most influential TF hubs in the N-signaling response. For example, the "early response" TFs CRF4 and SNZ—chosen for functional validation herein—were ranked #28 and #18 on the most-connected TF list in the N-regulatory network. Many of the edges in our "pruned" high-confidence N-regulatory network, were supported by TF-target binding data (DAP-Seq) (FIG. 3b). Moreover, our GRN indicates the direction of regulation, which establishes in vivo context of these interactions in N-response. This refined GRN network contains many, yet to be explored, layers of intricate regulation that propagate the initial N-signal into the global transcriptional changes writ large (FIG. 1).

The temporal N-regulatory network described herein offers a rich resource for the plant community to identify and validate crucial TF hubs and TF-interactions in the N-response cascade. Importantly, the high confidence GRN and predicted FFLs will suggest which TF combinations to test in "stacking" experiments aimed to increase the Nitrogen Use Efficiency (NUE) in transgenic plants and crops. Additionally, the targets of these known and novel TF regulators can be gleaned from this dynamic N-regulatory network, thus revealing the potential mode-of-action for the TF combinatorial experiments.

Beyond generating the temporal "transcriptional logic" that will valuable for the important global goal of enhancing NUE, our study describes a general time-centric approach that uses fine-scale time-course data to fuel causal network inference to understand stimulus-driven regulatory networks. We also describe two analysis approaches—"just-in-time" analysis and N-specificity index, which are useful to uncover the regulatory structure and signal-specificity in other time-series transcriptome datasets for other signals in any system. When coupled with genome-wide TF-target binding data (e.g. ChIP-Seq, DAP-Seq) and other layers of genomic data (e.g., chromatin accessibility maps), the experimental/computational approach employed in our time-based study may provide a powerful way to discover the key molecular players, their hierarchy, FFLs and other emergent network properties in any complex transcriptional regulatory system.

Methods

Experimental Analyses

Plant Material and N-Treatments:

*Arabidopsis thaliana* cv. Columbia (Col-0) were obtained from Lehle Seeds (USA). Seeds were vapor sterilized, stratified for 48 h, and then sown on sterile Phytatrays (Sigma) containing modified MS media minus C and N (Sigma), supplemented with 0.5 g/l MES hydrate (Sigma-Aldrich), 1% sucrose and 1 mM $KNO_3$ and brought to pH 5.7. Seedlings were grown in this media in an Intellus environment controller (Percival Scientific, Perry, Iowa), under long-day (16 h light/8 h dark) conditions with light intensity of 120 μmol m's$^1$ at constant temperature of 22° C. for two weeks. Two hours after the start of the light-period, seedlings were treated with either 60 mM nitrogen (20 mM $KNO_3$+20 mM $NH_4NO_3$) or 20 mM KCl and harvested at time intervals 0, 5, 10, 15, 20, 30, 45, 60, 90, and 120 minutes. Roots and shoots from each Phytatray were harvested separately and immediately flash frozen in liquid nitrogen. Three independent Phytatrays were harvested at each time-point to provide three treatment replicate root and shoot samples for analysis.

Plant Growth and Phenotyping:

Wild-type Col-0 and the CRF4 overexpression (CRF4-OX) lines (CS2104638) (Coego et al., Plant J, 2014. 77(6): p. 944-53) were grown on agarose plates containing 1/2 strength MS media for 7 days. The CRF4 transgene expression is driven by a β-Estradiol inducible promoter (Coego et al., Plant J, 2014. 77(6): p. 944-53). Plants were transferred to plates representing a two-factor combination of a. 100413-Estradiol or DMSO (β-Estradiol solvent) and b. 30 mM or 0.5 mM Nitrogen, supplied as $NH_4NO_3$. Plants were allowed to grow on this media for 5 days after transfer. At the end of five days the plates were scanned with a flat-bed scanner to capture high-quality images of root architecture as described before (Ristovay et al., Sci Signal, 2016. 9(451): p. rs13). The roots and shoots from three replicate plates (n=6) were harvested in pre-weighed tin foil cups. The harvested tissue was dried by placing it in a drying oven at 65° C. for 72 hours. Individual foil cups were weighed again, using a Mettler Toledo XPR6U Microbalance, to determine the dry weight of roots and shoots. Root images were analyzed to measure: primary root length, number of lateral roots, and total lateral root length, using the segmented line measurement tool in ImageJ. For each of the measured phenotypes, we compared the mean phenotype measure of the CRF4-OX plants to the mean measure of the Col-0 plants using a ANOVA model (Two factors: Genotype & Treatment). We then used a TukeyHSD test to compare the group means of each group (Genotype×Treatment) and confirmed that the mean biomass and root length of the β-Estradiol induced CRF4-OX lines are significantly different ($p<0.01$) from the wild-type and un-induced (e.g. DMSO-treated) CRF4-OX lines. The biomass and root growth phenotypes were confirmed by repeating the experiment in 0.5 mM N (supplied as $NH_4NO_3$) plates with or without 10 μM β-Estradiol and a larger number of individual plants (n=12) were assayed under each condition. The shoot biomass, total lateral root length and the number of lateral roots were significantly lower (p-val<0.01) in the CRF4-OX plants compared to the Col-0 plants.

Root Nitrate Influx Studies.

Root $^{15}NO_3$— influx was assayed as described previously (Munos et al., Plant Cell, 2004. 16(9): p. 2433-47). Briefly, wild-type (Col-0), CRF4-OX and nrt2.1 plants were grown for seven days on vertical agar plates containing nutrient solution and 0.5 mM $NH_4NO_3$. Plants were transferred to fresh plates containing 10 μM B-estradiol (or DMSO as a control) to induce the TF expression. Twenty-four hours after transfer, the plants were washed with 0.1 mM $CaSO_4$ liquid solution in petri dishes for 1 min, then to a nutrient solution (pH 5.7) containing 0.5 mM $15NO_3$— (99% atom excess $^{15}N$) for 5 minutes, and finally washed in 0.1 mM $CaSO_4$ for 1 minute. Roots were then separated from shoots, and the organs were dried at 70° C. for at least 48 hours.

After determination of dry weight for individual plants, the dried root samples were analyzed for total nitrogen and atom % $^{15}$N using a Euro-EA EuroVector elemental analyzer coupled with an IsoPrime mass spectrometer (GV Instruments). The mean $^{15}NO_3$— influx rate of the CRF4-OX plants was compared to the mean $^{15}NO_3$— influx rate of Wild-type (WT) and nrt2.1 plants using a ANOVA model (Two factors: Genotype & Treatment). We then used a TukeyHSD test to compare the group means of each group (Genotype×Treatment) and confirmed that the mean $^{15}NO_3$— influx rate of the induced CRF4-OX lines is significantly different ($p<0.05$) from the wild-type (induced and un-induced) and the un-induced CRF4-OX lines. The $^{15}NO_3$— influx rate of the induced CRF4-OX line is not significantly different from the nrt2.1 (induced and un-induced) lines.

Plant Growth Conditions for CRF4-OX Genome-Wide Targets:

Wild-type Col-0 and CRF4-OX (Coego et al., Plant J, 2014. 77(6): p. 944-53) (Accession no: CS2104640) lines were grown on 1% agar plates with nitrate-free 1×MS basal salts (Caisson Labs) supplemented with 1 mM KNO3 (Sigma-Aldrich), 0.5 g/liter MES sodium salt (Sigma-Aldrich) for 7 days. Treatment plates were flooded with a 2 mL of 10 µM β-estradiol solution while control plates were treated with 2 mL DMSO (solvent). The solutions were spread evenly over the plate for one minute and the excess was poured off. After 24 hours, seedling roots and shoots were harvested separately and immediately flash frozen in liquid nitrogen. Samples were harvested randomly between three replicate control and treatment plates with 12 roots or shoots pooled per sample, and RNA extracted for RNA-seq analysis.

RNA Extraction and Library Preparation for RNA-Sequencing:

Approximately 100 mg of tissue was used to extract total RNA from pulverized, frozen roots and shoots with an RNeasy Mini Kit (Qiagen) with on-column DNase treatment. mRNA was purified using Dynabeads Oligo (dT)$_{25}$ and analyzed on an Agilent Bioanalyzer to determine purity and quantity. mRNA was fragmented to 200-250 bp fragments prior to cDNA synthesis. Reverse transcription was performed using SuperScript III (Invitrogen, 18080-044) with second-strand synthesis with dUTPs, followed by cleanup, end repair, and dA-tailing. Universal Y-shaped adapter ligation was performed to enable sample multiplexing. Library amplification and multiplexing were performed using dUTP excision and amplification followed by PCR enrichment using 2× Phusion HF Master Mix (NEB, M0531L). Size-selection was performed using gel extraction and purification (Qiagen Gel Extraction Kit). Final quantity was determined using the DNA Bioanalyzer Chip and KAPA Library Quant qPCR. The cDNA libraries were sequenced on the Illumina HiSeq 2500 v4 platform in paired end mode for 100 cycles.

Genome-Wide Targets Identified by Plant Cell-Based TARGET Assays:

The TARGET system (Bargmann et al., Mol Plant, 2013. 6(3): p. 978-80) was used to identify the genome-wide targets of N-signal regulators CRF4, SNZ and CDF1. The plants were grown in 1 mM N for 10 days prior to the experiment. The shoot protoplast preparation, transient transformation and cell-sorting were performed as described previously (Para et al., Proc Natl Acad Sci USA, 2014. 111(28): p. 10371-6). Protoplasts isolated from shoots were treated with 20 mM KNO3+20 mM NH4NO3 prior to TF induction by DEX. Cells over-expressing the candidate TF or empty vector were collected in triplicate and RNA-Seq libraries were prepared from their mRNA using the NEB-Next® Ultra™ RNA Library Prep Kit for Illumina®. The libraries were pooled and sequenced on the Illumina Next-Seq 500 platform for 75 cycles. The RNA-Seq reads were aligned to the TAIR10 genome assembly using bowtie2 (Langmead et al., Nat Methods, 2012. 9(4): p. 357-9) and gene expression estimated using the HTSeq package (Anders et al., Bioinformatics, 2015. 31(2): p. 166-9). Genes showing differential expression between the TF overexpression libraries and the empty vector libraries were identified using DESeq2 package at a significance level of FDR<0.05.

Bioinformatic Analyses

RNA-Sequencing Analysis and Identification of Time-Dependent N-Response Gene Expression:

RNA libraries were made from plants treated with N over time (see Plant N-treatment above). Raw reads were trimmed to remove low quality bases (q<10) and adapter contamination. Gene expression levels were determined by aligning reads to the *Arabidopsis thaliana* genome (TAIR10) using the TopHat (v2) package (Kim et al., Genome Biol, 2013. 14(4): p. R36.) and estimating read counts by the HTseq package (Anders et al., Bioinformatics, 2015. 31(2): p. 166-9). Gene expression counts across the libraries were normalized using a quantile normalization method as implemented in the EDASeq R package (Bullard et al., BMC Bioinformatics, 2010. 11: p. 94). Genes responding to nitrogen significantly (FDR adjusted p-val <0.05) over the time-series N-response data were identified by fitting a Cubic Spline Model (df=5) to the N-treatment and Control samples, using the lmFit function in the Limma R package (Ritchie et al., Nucleic Acids Res, 2015. 43(7): p. e47). The N-treatment and control spline models were contrasted using the eBayes function implemented in the Limma package (Ritchie et al., Nucleic Acids Res, 2015. 43(7): p. e47). The response curves of gene expression (FIG. 13b) were visualized using the ggplot2 package (Wickham, Use R! 2009, New York: Springer. viii, 212 p.) in R.

GRN Network Construction and Network "Pruning" Refinement:

A previously validated machine learning approach that implements Dynamic Factor Graphs (Krouk et al., Genome Biol, 2010. 11(12): p. R123; Mirowski et al., *Machine Learning and Knowledge Discovery in Databases: European Conference, ECML PKDD 2009, Bled, Slovenia, Sep. 7-11, 2009, Proceedings, Part II*, W. Buntine, et al., Editors. 2009, Springer Berlin Heidelberg: Berlin, Heidelberg. p. 128-143), was used to derive the TF-target interaction in response to N-treatment. Briefly, the dynamic behavior of the 172 TFs that respond to N-supply in shoots was used to model the behavior of the 2,172 genes responding to N-supply in shoots. We use the time-series transcriptome data to learn hyper-parameters of the Dynamic Factor Graphs (DFG) model using a leave-out time-point, and then inferred edges based on the constructed model. Briefly, DFG identifies the likely set of TFs driving target gene expression, by learning an f function that explains the target gene expression at each time-point, based on the expression of the TFs at previous time-points (Mirowski et al., *Machine Learning and Knowledge Discovery in Databases: European Conference, ECML PKDD 2009, Bled, Slovenia, Sep. 7-11, 2009, Proceedings, Part II*, W. Buntine, et al., Editors. 2009, Springer Berlin Heidelberg: Berlin, Heidelberg. p. 128-143). Since DFG attempts to establish causality of gene expression, it benefits greatly from closely spaced time-points, as used in our study. Hyper-parameter optimization is the process of choosing a set of hyper-parameters for a good generalization of a learning algorithm (Bishop, Information science and statistics. 2006, New York: Springer. xx, 738 p). Our dataset contains 10 time points. We train DFG on the first 9 time-points, and tune the hyper-parameters to minimize error on the last time point. Then we look at the final matrix we obtain using all 10 time points, where the matrix estimates the influence of each TF on every N-responsive gene. This matrix is constructed as a network with the coefficient of TF influence on a given gene assigned as the edge score for that network edge. The true, i.e., experimentally validated edges of 3 TFs (CRF4, SNZ, CDF1. See FIG. 4a) were then used to calculate and plot the network precision and recall (FIG. 4c). Briefly, the predicted edges in the DFG-inferred GRN are ranked by their score (i.e., the coefficient of influence of TF on its target gene). The network precision and recall are then computed by sliding down the ranked list and labeling each edge as validated (True positive) or not (False positive). After each step the Precision (True Positives/(True+False Positives)) and Recall (True Positives/(True Positives+False Negatives)) of the network is recalculated. From these precision and recall measures we determined the minimum edge score that meets a network precision of 0.345 (FIG. 4c). This edge score threshold corresponds to 0.95554 in the DFG network and was chosen to minimize false positives (i.e., higher precision) while recovering as many true positives as possible. Therefore, all predicted edges with an edge score >=0.95554 (FIG. 4c) were retained to generate the predicted TF-target network. This "pruned" DFG-inferred network represents a highly conservative estimate of the true influence of a TF and therefore has a low recall rate compared to the genome-wide targets of each of these TFs (FIG. 4a and FIG. 5). Experimental support for TF→Target interactions was obtained from independent TF-binding data (FIG. 3b). This TF-target DNA binding dataset included TF-target information for 35 N-responsive TFs with DFG predictions (FIG. 3b). For each TF with target predictions (DFG) and binding data (DAP-Seq), the two target sets were intersected to identify supported edges i.e., TF is predicted to regulate the target (by DFG) and TF is shown to bind to the target gene promoter (by DAP-Seq) (FIG. 3b).

"Just-in-Time" Analysis of Time-Series Transcriptome Data

The normalized expression level of the N-response genes in shoots (2,172 genes) and roots (2,681 genes) (FIG. 1 b) at each of the time-points assayed (0-120 min) was used to calculate the fold-change of expression between the N-treated samples and the controls (KCl). For "just-in-time" analysis, each gene was then assigned to the first time-bin at which the fold-change of expression is >=1.5. The promoters of all genes in each "just-in-time" gene set were then analyzed to identify over-representation of cis-regulatory element motif (FDR corrected e-val <0.05) using an online search tool (Elefinder (Li et al., Plant Physiol, 2011. 156(4): p. 2124-40)). Cis-regulatory motifs that are rare in the genome were filtered out to remove spurious associations by requiring that for each "just-in-time" bin every over-represented cis-motif must be present in at least 5 or more promoters in that gene set. The resulting matrix of over-represented cis-elements in genes at each "just-in-time" points was hierarchically clustered and visualized using MeV (Howe et al., Bioinformatics, 2011. 27(22): p. 3209-10.) (FIG. 2A). Separately, all genes in each "just-in-time" gene set were analyzed by the BioMaps function in VirtualPlant (Katari et al., Plant Physiol, 2010. 152(2): p. 500-15) to identify over-represented GO-terms in each bin (FIG. 2B).

Calculating the "Nitrogen-Specificity Index" for TFs in the GRN.

Of the 172 TFs that respond to N-signal in the shoot, DAP-Seq genome-wide binding data (O'Malley et al., Cell, 2016. 166(6): p. 1598) is available for 40 TFs. For each of these TFs, their genome-wide targets were retrieved from the Plant Cistrome Database (O'Malley et al., Cell, 2016. 166(6): p. 1598; Ecker, 2017; Available from: (neomorph.salk.edu/dap_web/pages/index.php). We next obtained the subset of each TF's target in the N-signal response genes, by intersecting the genome-wide targets of each TF with the N×Time signal response genes in shoots (2,172 genes) (FIG. 1b). For each TF, the proportion of its targets in the genome was calculated as $p_g = T_g/G_g$ where $T_g$ is the total number of TF targets in the genome and $G_g$ is the total number of genes in the genome. Again, for each TF, the proportion of its targets in the N-signal response gene set was calculated as $p_n = T_n/G_n$ where $T_n$ is the total number of TF targets in the N-signal response geneset, and $G_n$ is the total number of genes in the N-signal response geneset. The significance of each TF to the N-signal was then tested by a one-tailed t-test under the null hypothesis $p_n = p_g$. The TFs with a significantly higher $p_n$ than $p_g$ (p-val <0.01) were accepted as being specific to the N-signal (FIG. 7).

Genome-Wide Discovery of Network Motifs (FFLs):

The GRN N-response network inferred by DFG was visualized in Cytoscape (v2.8.3), and the sub-network connecting only TFs with DAP-Seq validated edges was selected using the node annotation selection tool. Within this network, regulatory feed forward loops (FFLs) were identified using the "Netmatch" network querying plugin.

Example 3

High Through-Put Validation of a TIME-Based Network of Transcription Factors Controlling the Nitrogen Response in Plants.

This example describes a high throughput method to rapidly validate the regulated targets of many transcription factor (TFs) using a transient assay in isolated plant cells. This modification of the TARGET method enables us to screen 8TFs/day or 16 TFs/week. We present the results for 23 TFs involved in the N-response pathway in plants, and identify their regulated targets in the genome. We show that these 23 TFs specifically target genes that respond to N-signals over time. Importantly, the method and analysis we describe herein enables one to identify TFs that jointly target common genes and network modules. This information can then be used to select pairs or sets of TFs for "stacking" experiments in planta. The working example is for N-response genes, but the method and analysis approach can be used to identify TFs that work together to regulate any pathway or process in plants. This method can greatly speed up validation testing of TFs to prioritize them for transgenic plant studies and for combinatorial stacking.

Results

Modifications to the TARGET System Enable Increased Throughput of Transcription Factor Screening.

In the original TARGET experimental design (Bargmann et al., (2013) Mol Plant 6, 978-980), we described a system for transient TF perturbation in isolated plant cells. In the original iteration of TARGET, a single vector containing a GR-TF fusion and RFP reporter was used to transfect protoplasts. Targets of that TF were then identified by comparing expression profiles from TF-induced cells (+Dex) to TF-uninduced cells (−Dex). To increase throughput of TARGET assay, two changes were made to the system (FIG. 19). First, an additional vector was constructed that contains a GFP reporter. When two populations are transfected separately, one with the original RFP containing vector, and the other with the new GFP containing vector, these cells can be pooled and treated with Dex and/or nitrogen together. The GFP and RFP expressing protoplast can then efficiently be sorted (using FACS—Fluorescent Activated Cell Sorting) into separate collection tubes. FACS sorting is one of the major time-limiting step in the TARGET system, and this new modification allows us to sort twice as many TF-expressing samples in nearly the same amount of time The second significant modification to the TARGET protocol (Bargmann et al., (2013). Mol Plant 6, 978-980), is that batches of protoplasts were transfected with different GR-TF constructs. To identify differential expression resulting from the induced nuclear translocation of the TF by Dex, on each day that an experiment is done, we also transfect and treat a population of cells with an Empty Vector (EV), a construct containing only the GR and no TF. This allows us to compare gene expression of each GR-TF construct pairwise to the EV control. Incorporating these two changes into the TARGET system allows us to increase the number of TFs analyzed from 1-2 TFs per week to 16 TFs per week.

Figure 20:
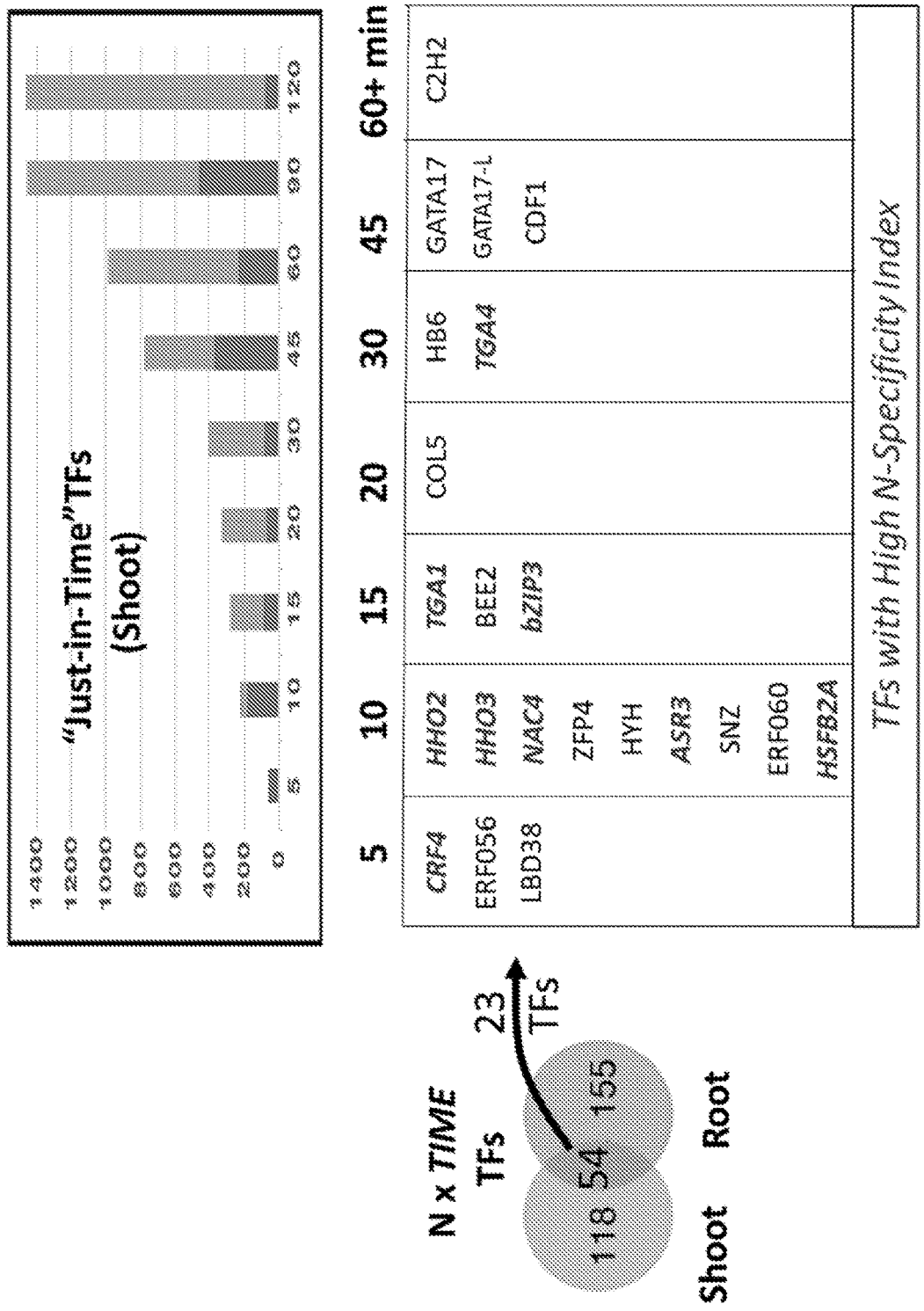
FIG. 20.

To validate this new high throughput TARGET approach, we chose 23 TFs for preliminary evaluation (FIG. 20). We focused on TFs that responded to nitrogen in both the shoot and root Nitrogen by Time network (Example 2). We also biased our selection of TFs towards those that respond early (5-10 min) and those with a high N-specificity index as calculated in Example 2.

Figure 21:
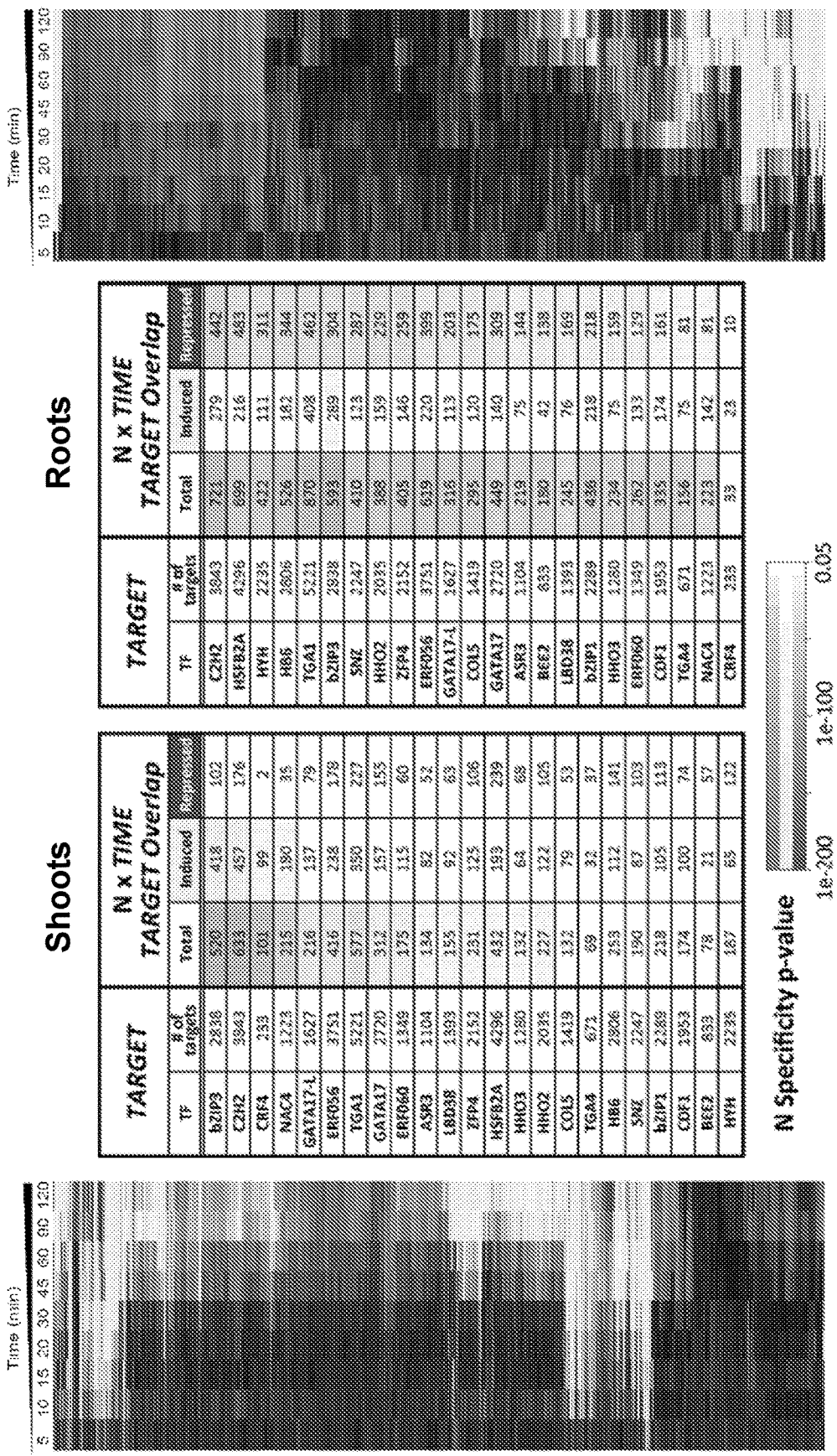
FIG. 21. Validated targets of 23 TFs significantly overlap with N×TIME data. The number of targets identified as being differentially expressed (FDR<0.05) for each TF ranges from 233 to 5221. We also determined the number of genes in the overlap between the TF-regulated targets and the nitrogen responsive genes in either shoots (heatmap on the far left) or roots (heatmap on the far right) from Example 2. This overlap is reported for the all of the targets of the TF and after separating them into the induced targets and the repressed targets. The N-specificity of each TF, for all targets, induced targets and repressed targets, was calculated as in Example 2, and the cells were shaded according to the p-value of this enrichment vs. their effect on the entire *Arabidopsis* genome.

For Each TF, a Set of Induced and/or Repressed Targets are Enriched in N×Time Responsive Genes Transcriptome responses for each of the 23 TFs tested were examined at 3 hours after induced nuclear entry of the GR-TF fusion by Dex. To obtain a list of differentially expressed genes, each set of TF samples were compared a set of similarly treated EV replicates done on the same day. The number of targets identified as differentially expressed between each TF and EV (FDR<0.05) ranged from a low of 231 gene targets (CRF4) to a high of 5,163 gene targets (TGA1), with the average number of TF-targets of around 1,800 (median 1764, mean 1884) (FIG. 3). No TF was found to affect gene expression in one direction, that is, for each TF there were a significant number of induced and repressed targets. The number of induced targets ranges between 26% (BEE2) and 77% (CRF4) with a median of 42% (mean 45%) (FIG. 21).

As these 23 TFs were primarily chosen on the criteria of being responsive to N in both shoots and roots in the N by Time experiment (Example 2), we examined whether the targets of each TF significantly overlapped with the either the shoot or root N-responsive genes from that experiment. To do so, we calculated the N-specificity of the TFs using the method described in Example 2, but in this case used all of the regulated TF targets from our TARGET assays to calculate the enrichment in the N-response (FIG. 21). We separated the N-response between shoots and roots, as the tissue context may effect these results. Also, in addition to looking at total regulated targets, we did the N-specificity calculations using only induced or repressed targets for each TF. When comparing TF-target data to shoots, 16 TFs have targets that are enriched (p-value <0.01) in N responsive genes in shoots. Interestingly, this enrichment is almost entirely driven by the induced set of genes (FIG. 21). For example, when the TF targets are separated into induced vs. repressed sets, only the repressed targets of HHO2 are still significantly enriched at the same cutoff, and the enrichment for the induced target genes for each nearly every TF is increased. This fits well with the observation that in shoots, a majority of N-responsive genes are induced by the N signal. In roots, when taking into account all of the targets of the TF, all the TFs tested have a significant enrichment for the N-response (p-value <0.01) (except for CRF4). This holds true for both induced and repressed targets of the 23 TFs. However, by contrast to the scenario in the shoots, in the roots the targets that are repressed by a TF show a higher enrichment in root N by Time responsive genes. Again, this fits the observation that there are slightly more N-repressed genes in the root data set (FIG. 21).

N-Related Processes are Enriched in the Individual and Common Targets of the 23 TFs After separating the list of genes regulated by each TF in the TARGET system into induced and repressed genes, GO-term analysis reveals a large number of biological processes that are targeted by these TFs. Of the enriched biological processes in the induced set of genes for each TF, 782 enriched biological process were found, the most significant GO-term is "translation". These genes are specific targets of the TFs CRF4, bZIP3, NAC4 and C2H2-1. As for enriched GO-terms in repressed targets, over 3000 GO-terms are found for the common targets of the 23 TFs, and the most enriched processes tend to be more general (e.g. response to stimulus and response to stress). However, more specific terms (e.g. response to metal ion, response to salt etc.) were also found. Additionally, 21 of the 23 TFs were found to be enriched in targets of one or more biological processes directly related to N (e.g. nitrogen compound metabolism, nitrogen compound biosynthesis, nitrate transport, and nitrate assimilation).

As many of the 23 TFs tested were found to share GO-terms, such as those related to N, and many targets seemed to be shared between TFs. To quantify this, we binned each target gene based on how many times it showed up as being differentially expressed in the TARGET experiments for the 23 TFs tested (FIG. 22). The largest group of target genes, 3620, is for those genes that are regulated by only one TF. As the number of TFs influencing target genes in the genome increases, the size of the group decreases, and no one target gene is regulated by all 23 TFs. While the number of unique targets for each TF is large, it is only slightly larger than the number of genes that are targeted by more than 5 of the 23 TFs (3342 genes). In fact, there are 1,047 genes that are targeted by at least 10 of the 23 TFs examined. GO-term analysis of this set of common genes targeted by 10 or more TFs reveals an enrichment (p-value <1e-4) of several interesting biological processes including N compound biosynthesis, amino acid metabolism, response to several hormones and root development (FIG. 22).

Combining TF-Regulation (TARGET) and TF-Binding (DAP-Seq) Reveals the Importance of Cis Context to TF Function To integrate our TF-regulation data from TARGET, with information about TF binding, we analyzed those TFs that also have DAP-Seq data available. Dap-Seq is an in vitro TF-DNA binding assay by which TF binding to a DNA target is analyzed by combining a TF protein expressed in vitro with naked genomic DNA isolated from plants. This in vitro system was used to identify potential genome-wide targets and binding motifs for 529 Arabidopsis TFs. 10 of the 23 TFs we tested in TARGET were present in the DAP-Seq data set. Out of the 10 TFs that were tested in both TARGET and by DAP-Seq, 8 showed a significant overlap for the intersection of the regulated genes from TARGET and the genes bound by the TF in the DAP-Seq experiment (FIG. 23). Only CRF4 and ASR3 did not significantly intersect between our TARGET and DAP-Seq datasets. Dividing the regulated targets between induced and repressed genes before overlapping with the DAP-Seq binding data demonstrates that DAP-binding is often significantly enriched for both types of regulation, but more strongly associated with either induction or repression by a TF.

To further analyze how TF-regulation as assayed by our TARGET system can be used to give context to TF-binding data, we analyzed the occurrence in our sets of TF-regulated genes for the cis-motif that was found to be most enriched within 200 bp of the top 600 TF-binding DNA peaks identified for each of these 10 TFs by DAP-Seq (O'Malley et al., Cell 165, 1280-1292) (FIG. 23). We used Elefinder to assess at the enrichment of the DAP-motif for each of the 10 TFs in common between the two datasets in the promoters of genes: A) Associated with an expanded set of DAP-peaks (the top 1500 peaks), B) The TF-induced genes from TARGET, and C) The TF-repressed genes from TARGET. As expected, the cis-motif for each TF was found to be significantly enriched (p-values between 3e-18 and 3.5e-203) in the promoters of genes that it binds in DAP-seq, even when more than twice as many peaks are considered. For the TF-regulated genes, only two TFs tested showed an enrichment of the motif in both the induced and repressed TARGET data, HB6 and CRF4 (FIG. 23). Of the remaining 8 TFs, three showed enrichment of the DAP-motif in only the repressed genes, and 5 only in the induced genes. This suggests that the DAP-motif is often associated with a particular role of the TF. In general, the p-values for the enrichment of the cis-motif in the TARGET data was less than in the DAP-data. Taken together, these data indicate that the TF-regulation data adds value to the DAP-seq data—as it provides the DIRECTION of regulation. Our results also suggest that caution must be used when using cis-element analysis from TF-DNA binding alone, especially when it is determined in vitro, in predicting TF targets.

Clustering of TFs into Functional Groups Using Weighted Gene Correlation Network Analysis.

Figure 24:
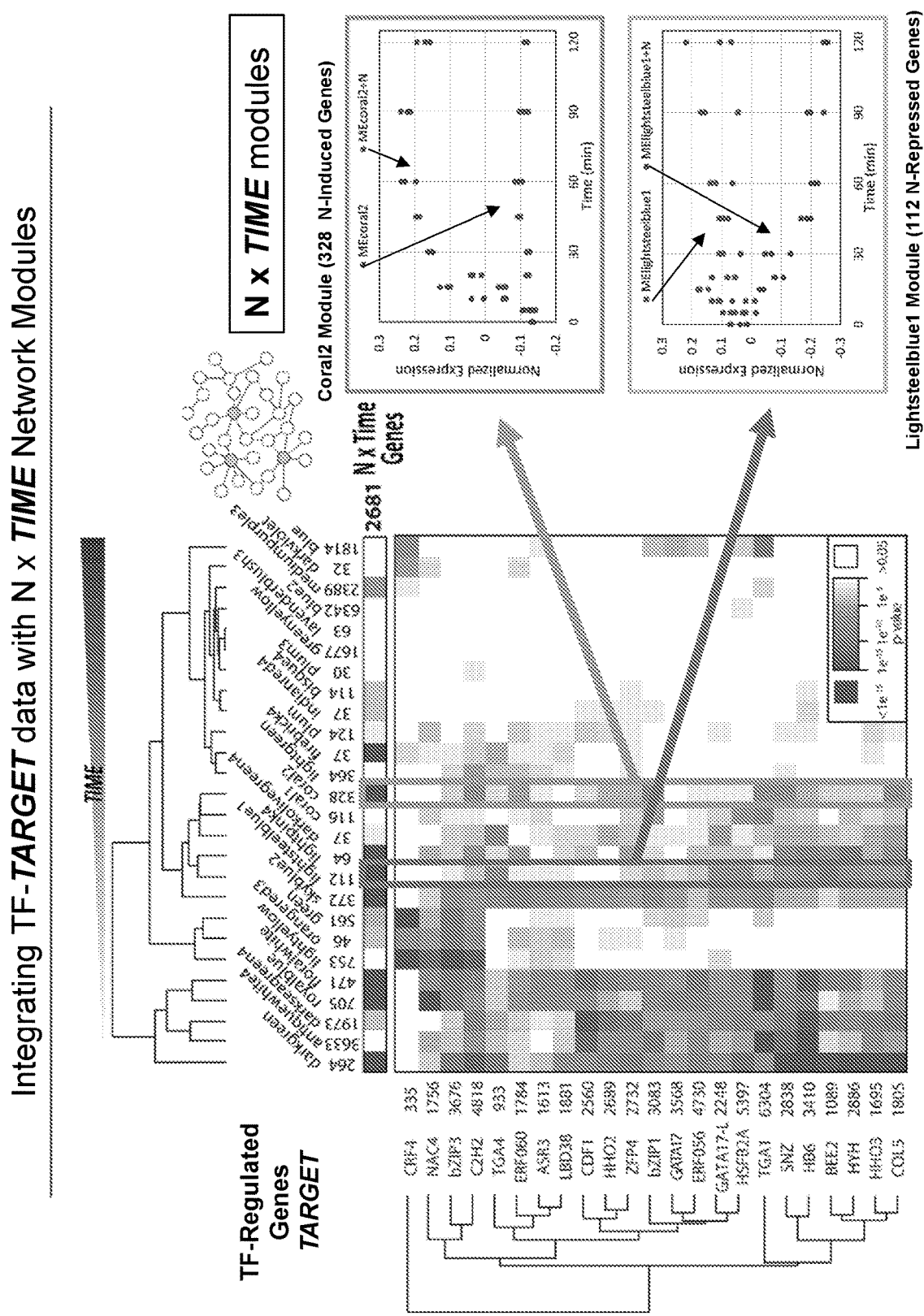
FIG. 24. WGCNA generated from the root Nitrogen by Time expression data groups all expressed genes into modules. Weighted Genome Correlation Network Analysis (WGCNA) was applied to the expression data from the 57 root N by Time samples from Example 2. The 22,458 expressed genes were put into modules 25 modules of varying size. The membership within a module is based on how that set of genes responds to N and the control treatment over time and can be represented by the module eigengene, displayed here for two modules, coral2 (328 N induced genes) and lightsteelblue1 (112 N repressed genes). The genes within each module were then intersected with the set of root Nitrogen responsive genes and p-value for the overlap was used to shade the heatmap.

We sought to relate the TF TARGET data back to the N×time transcriptome data from which the TFs were chosen (Example 2). To do so, we performed Weighted Gene Correlation Network Analysis (WGCNA, Langfelder et al., (2008) BMC Bioinformatics 9, 559) using the root transcriptomes from the N×time (Example 2). Briefly, WGCNA uses the expression of every expressed gene across a large number of samples, in this case 57 N-treatment samples (over time), to generate a correlation network. Importantly, this network is transformed with a power adjacency function in order to create a weighted, scale-free network, which is thought to better describe gene regulatory networks. This network is then used to identify modules, clusters of genes that are highly correlated, and these modules can be described by an eigengene, a theoretical gene that describes the behavior of the module across the samples. Our analysis of the root N×time data placed 22,458 expressed genes into 25 network modules, ranging in size from 32 to 6342 genes/module (FIG. 24). The genes in each module were intersected with the root N×Time responsive genes (2681) and the overlap was used to calculate an FDR-corrected significance. The results in FIG. 24 show that certain network modules are more (dark) or less (white) enriched in N-responsive genes. Looking at the eigengene for different modules, we see that in general, a module describes how that set of genes responds to N over time or the control treatment. For example, the Coral2 module contains genes that are induced by N over time compared to the control, while the Lightsteelblue1 module contains genes that are repressed over time compared to the control (FIG. 24).

Figure 25:
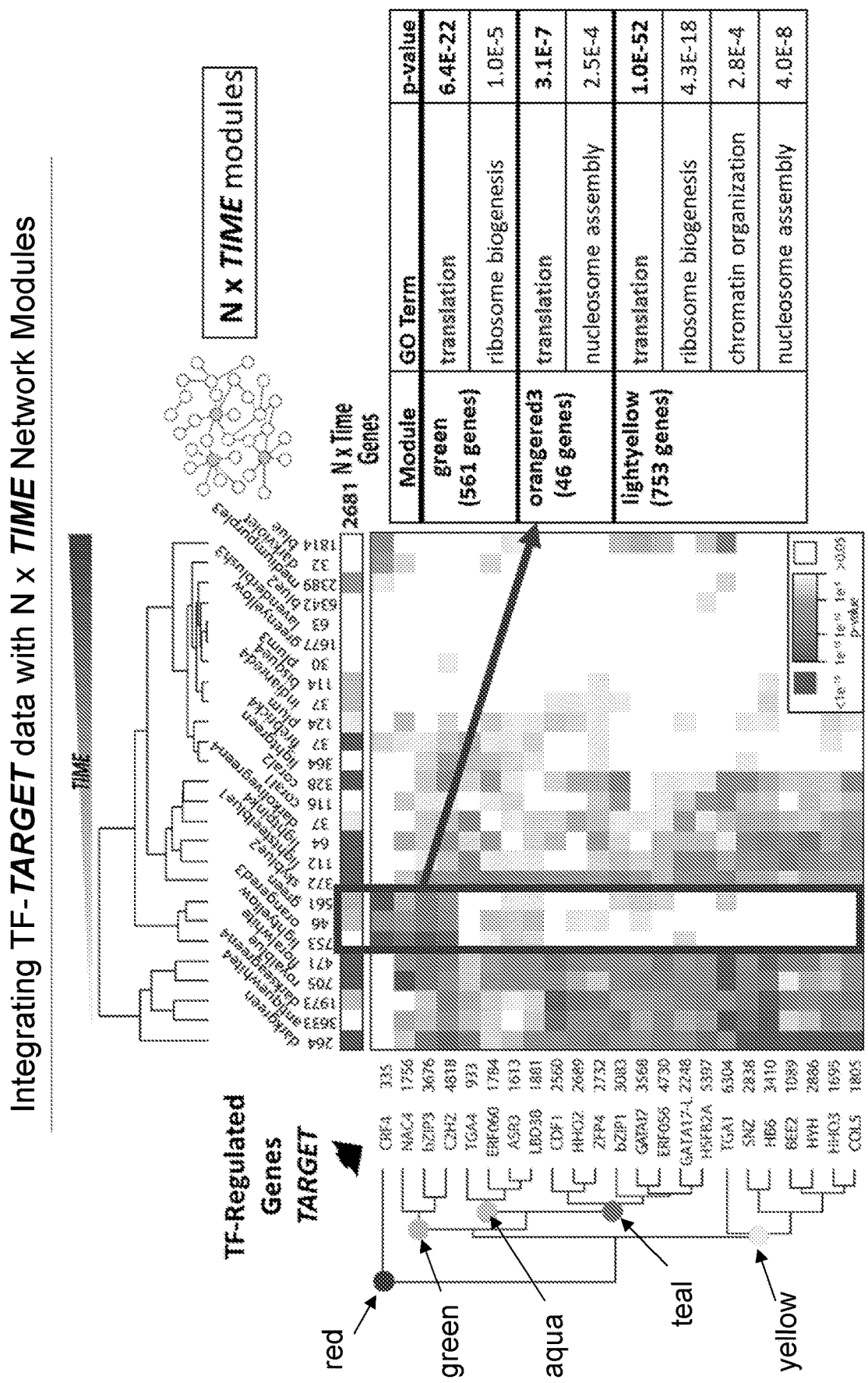
FIG. 25. Clustering of TFs based on the intersection of their regulated targets with the members of each module. The WGCNA modules were intersected with the regulated targets of each TF determined from the TARGET experiments and the p-value for the intersection was used to generate a heatmap. The TFs were also clustered based on these values and the resulting dendogram was used to group TFs into five clusters that regulate similar modules. GO-terms can also be analyzed for each module and used to define which set of TFs regulate certain processes. An example is shown, where the Green and Red clusters of TFs (CRF4, NAC4, C2H2, and bZIP3) are uniquely enriched in genes in that make up the lightyellow, orangered3 and green modules. These modules are enriched in several GO-terms, most significantly for genes associated with translation.

The N×time network modules created using WGCNA were then intersected with the TF-regulated targets for each of the 23 TFs tested in TARGET, and enrichment was similarly calculated. In general, the modules whose genes are most influenced by the 23 TFs are also those that are also responsive to N (FIG. 25). We use the enrichment of TF-regulated target genes in the different modules to cluster the TFs. This clustering informs us on which TFs regulate genes with similar responses, and which TFs may be working together to control a specific set of genes, or different genes that may be involved in the same process. Twenty-two of the 23 TFs were divided into four major TF clusters (Green, Aqua, Teal, Yellow), with CRF4 being alone at the root of the dendogram and assigned to its own Red cluster (FIG. 25). The CRF4 regulated targets are the only group of genes that do not show an enrichment the modules that are N-responsive. This is not unexpected as the overlap between CRF4 and the root response was small and not significant (FIG. 22). CRF4 targets are particularly enriched for genes in the lightyellow, orangered, and green modules from WGCNA N×time analysis. The targets of the TFs in the Green TF Cluster (comprising NAC4, bZIP3 and C2H2) are also enriched in the lightyellow, orangered and green WGCNA modules, but this set of TFs also effects many of the other N-responsive modules. The TFs in the Yellow TF Cluster (TGA1, SNZ, HB6, BEE2, HYH, HHO3, COL5) are all enriched for target genes in the darkgreen WGCNA module. The Aqua TF Cluster (TGA4, ERF060, ASR3, LBD38) has a somewhat lower enrichment across all the N-responsive modules, and the Teal TF Cluster (CDF1, HHO2, ZFP4, bZIP1, GATA17, ERF056, GATA17-L, HSFB2A) does not show any clear pattern of enrichment across the WGCNA modules.

By looking at GO-Enrichment of the genes within a module, we are able to generate some hypotheses about which TFs may work in concert to regulate specific biological processes. For example, the TFs in the Green TF Cluster (NAC4, bZIP3, C2H2)—along with CRF4—regulate the lightyellow, orangered and green modules from the WGCNA analysis. These three WGCNA N×time modules all share "translation" as a significantly enriched GO term (FIG. 25). Similarly, the darkgreen WGCNA module, which is regulated by the Yellow TF Cluster (TGA1, SNZ, HB6, BEE2, HYH, HHO3, COL5) is enriched in GO terms such as; "protein phosphorylation", "defense response" and "calcium ion transport". We are starting to address whether the TFs regulating the TFs in these modules effect the same or different genes within the WGCNA module. In the case of the TFs modules that regulate "translation" genes (e.g., CRF4, bZIP3, NAC4 and C2H2), all these TFs induce a set of 66 genes within those modules, and the enrichment for the "translation" GO term is even greater in this subset.

The Twenty Three N-Responsive TFs Form a Complex Nitrogen Regulatory Cascade.

Figure 26:
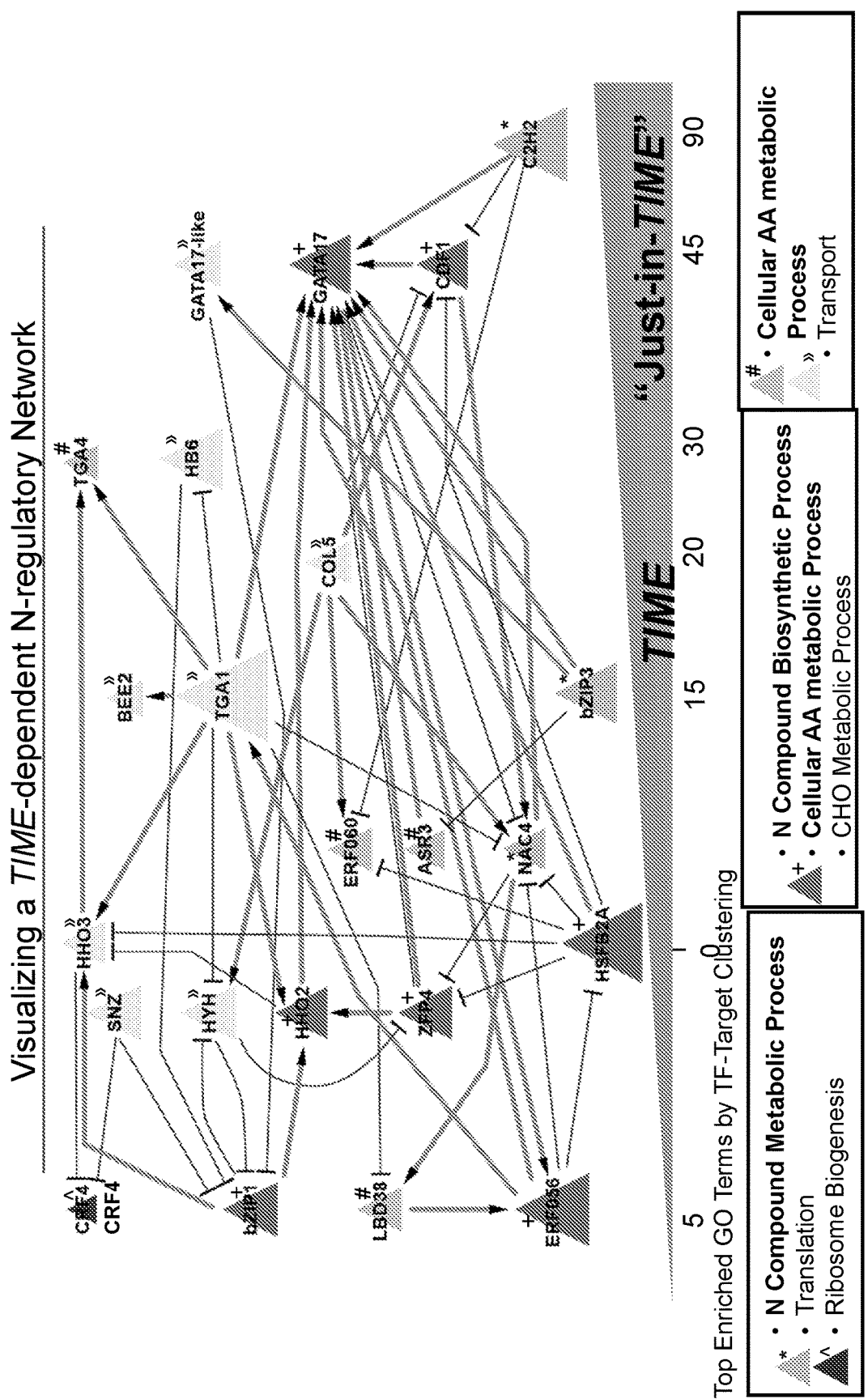
FIG. 26. A view of the nitrogen responsive TF interaction network built from the TARGET edges. A network view showing edges between TFs identified in the TARGET experiments, with the TFs arranged according to the time at which the respond (left to right) reveals feed-forward and feedback loops initiated by the N signal. Induced edges are shown as thick lines and repressed edges are shown in thin lines. The total number of genes that each TF regulates is proportional to the node size and the color of the nodes is based on the cluster to which they were assigned in WGCNA (FIG. 7). GO-terms enriched for genes that are in common between the set of TFs within each cluster are shown at the bottom.

By looking at edges between TF and target genes identified from the TARGET experiments that occur between the 23 TFs (FDR <0.1, |log 2FC|>0.5), we are able to obtain a complex network of TF-TF regulation (FIG. 26). As we know the time at which each of these TFs responds in the N by Time experiments in Example 2, we are able to place each in the context of time, creating a regulatory cascade that is initiated by N stimulus. From this network, we are able to identify the most influential TF (more out-edges) on the TF network, such as TGA1 and HSFB2A, as well as the more regulated TFs (more in-edges), such as GATA17. As we add additional TF TARGET experiments, we will add to these networks. This network shown in FIG. 26 also defines how these 23 TFs work in feed forward and feedback loops. The size of the triangle for each TF is proportional to its influence on the N-regulatory network.

While this disclosure provides various embodiments, routine modifications to the disclosure will be apparent to those skilled in the art, which modifications are intended to be within the scope of the disclosure.

What is claimed is:

1. A method for modulating Nitrogen (N) uptake, assimilation and/or usage in plant cell or a plant comprising under-expressing transcription factor CRF4, wherein the under expressing comprises editing a segment of a CRF4 gene, or comprises RNA interference (RNAi)-mediated targeting of mRNA encoding CRF4, the method further comprising overexpressing transcription factor SNZ and/or CDF1 such that the plant or plant cell has increased N assimilation.

2. The method of claim 1, wherein the TF or TFs are SNZ and/or CDF1, and the SNZ and/or CDF1 are over-expressed, wherein over-expression of SNZ and/or CDF1 results in increased N-uptake and/or assimilation.

3. The method of claim 1, wherein the plant is exposed to low N environment.

4. The method of claim 1, wherein underexpressing the CRF4 comprises disrupting a polynucleotide sequence that encodes or controls expression of the CRF4.

5. The method of claim 1, wherein the editing comprises Clustered Regularly Interspaced Short Palindromic Repeats (CRISPR) editing of the gene encoding the CRF4.

6. The method of claim 1, wherein the RNAi-mediated targeting comprises introducing into the plant cell a microRNA or an shRNA targeted to mRNA encoding the CRF4 gene, and wherein the mRNA is degraded.

7. The method of claim 1, wherein the plant is a species of woody, ornamental, decorative, crop, cereal, fruit, or vegetable plant.

8. The method of claim 7, wherein the plant is a species of a genus selected from the group consisting of: Acorus, *Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

* * * * *